(12) United States Patent
Godler

(10) Patent No.: US 10,138,521 B2
(45) Date of Patent: Nov. 27, 2018

(54) TREATMENT AND DIAGNOSIS OF EPIGENETIC DISORDERS AND CONDITIONS

(71) Applicant: Murdoch Childrens Research Institute, Parkville, Victoria (AU)

(72) Inventor: David Eugeny Godler, Ormond (AU)

(73) Assignee: Murdoch Childrens Research Institute, Parkville, Victoria (AU)

( * ) Notice: Subject to any disclaimer, the term of this patent is extended or adjusted under 35 U.S.C. 154(b) by 10 days.

(21) Appl. No.: 14/932,634

(22) Filed: Nov. 4, 2015

(65) Prior Publication Data
US 2016/0053326 A1 Feb. 25, 2016

Related U.S. Application Data

(62) Division of application No. 13/814,911, filed as application No. PCT/AU2011/001024 on Aug. 11, 2011, now abandoned.

(30) Foreign Application Priority Data

Aug. 11, 2010 (AU) .............................. 2010903595

(51) Int. Cl.
| | |
|---|---|
| C07H 21/04 | (2006.01) |
| C12Q 1/68 | (2018.01) |
| C12Q 1/6883 | (2018.01) |
| G06F 19/24 | (2011.01) |

(52) U.S. Cl.
CPC ............. *C12Q 1/6883* (2013.01); *C12Q 1/68* (2013.01); *G06F 19/24* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 6,143,504 | A | 11/2000 | Das et al. |
| 6,150,100 | A | 11/2000 | Rüschoff et al. |
| 2006/0024676 | A1 | 2/2006 | Uhlmann et al. |
| 2013/0017544 | A1 | 1/2013 | Eckhardt et al. |

FOREIGN PATENT DOCUMENTS

| | | |
|---|---|---|
| CN | 102021233 A | 4/2011 |
| WO | WO 92/20825 A1 | 11/1992 |
| WO | WO 02/034942 A2 | 5/2002 |
| WO | WO 2008/045136 A2 | 4/2008 |
| WO | WO 2009/045467 A1 | 4/2009 |
| WO | WO 2010/094061 A1 | 8/2010 |
| WO | WO 2012/019235 A1 | 2/2012 |

OTHER PUBLICATIONS

Godler et al. (Human Molecular Genetics, vol. 19, No. 8, pp. 1618-1632, Jan. 29, 2010) (Year: 2010).*
Hansen et al. (Human Molecular Genetics, vol. 1, No. 8, pp. 571-578, 1992) (Year: 1992).*
Fu et al. (Genbank Accession X61378, Jan. 1992). (Year: 1992).*
Cornish, K. et al. 2005 "The emerging fragile X premutation phenotype: Evidence from the domain of social cognition" *Brain and Cognition* 57: 53-60.
Franke, P. et al. 1998 "Genotype]phenotype relationship in female carriers of the premutation and full mutation of FMR-1" *Psychiatry Research* 80: 113-127.
Godler, D.E. et al. 2013 "Relationships between age and epigenotype of the FMR1 exon 1/intron 1 boundary are consistent with non-random X-chromosome inactivation in FM individuals, with the selection for the unmethylated state being most significant between birth and puberty" *Human Molecular Genetics* (in 9 pages).
Hagerman, R.J. et al. 2009 "Advances in the treatment of Fragile X Syndrome" *Pediatrics* 123: 378-390.
Hung, C.-C. et al., 2011 "Quantitative and Qualitative Analyses of the SNRPN Gene Using Real-Time PCR with Melting Curve Analysis." *Journal of Molecular Diagnostics*, 13(6); 609-613.
Inaba, Y. et al. 2012 "Fragile X-related element 2 methylation analysis may provide a suitable option for inclusion of fragile X syndrome and/or sex chromosome aneuploidy into newborn screening: a technical validation study" *Genetics in Medicine*, Advance online publication Oct. 11, 2012 (in 9 pages).
Malentacchi, et al. 2009 "Quantitative evaluation of DNA methylation by optimization of a differential-high resolution melt analysis protocol" *Nucleic Acids Research* 37(12).
Stoger, R. et al. 1997 "Epigenetic variation illustrated by DNA methylation patterns of the fragile-X gene FMR1" *Human Molecular Genetics* 6: 1791-1801.
Tassone, F. et al. 2011 "Differential usage of transcriptional start sites and polyadenylation sites in FMR1 premutation alleles" *Nucleic Acids Research* 39: (in 14 pages).
Tobler, A.R. et al. 2010 "Methylation Analysis Using Methylation-Sensitive HRM and DNA Sequencing" Applied Biosystems Application Note, Life Technologies Corpoation (in 6 pages).

(Continued)

*Primary Examiner* — Jeanine A Goldberg
(74) *Attorney, Agent, or Firm* — Knobbe, Martens, Olson & Bear, LLP

(57) ABSTRACT

The present disclosure relates generally to the field of epigenetics and in particular epigenetic profiles associated with a pathological condition. The present specification teaches screening of individuals and populations for epigenetic profiles associated with a pathological condition. The epigenetic profiles can be from an intron, an intron/exon boundary or a splicing region. Epigenetic profiles are disclosed from the following sites in the FMR locus: FREE3, intron 2 of FMR1, the genomic FREE2 region as a whole or specific FREE2 fragments including FREE2 (D) or FREE2 (E). Kits and diagnostic assays are also taught herein as are computer programs to monitor changes in epigenetic patterns and profiles. Further enabled herein is a method for screening for agents which can reduce or mask the adverse effects of epigenetic modification and the use of these agents in therapy and prophylaxis.

6 Claims, 18 Drawing Sheets

Specification includes a Sequence Listing.

(56) References Cited

OTHER PUBLICATIONS

Uhlmann 2002 "Evaluation of a potential epigenetic biomarker by quantitative methyl-single nucleotide polymorphism analysis" *Electrophoresis* 23: 4072-4079.

Wojdacz, T.K. et al. 2007 "Methylation-sensitive high resolution melting (MS-HRM): a new approach for sensitive and high-throughput assessment of methylation" *Nucleic Acids Research* 35(6): e41 (in 7 pages).

Wojdacz, T.K. et al. 2008 "Rapid Detection of Methylation Change at H19 in Human Imprinting Disorders Using Methylation-Sensitive High-Resolution Melting" *Human Mutation* 29(10); 1255-1260.

Wojdacz, T.K. et al. 2008 "Methylation-sensitive high-resolution melting" *Nature Protocols* 3(12): 1903-1908.

Zeschnigk, M. et al. 1997 "A single-tube PCR test for the diagnosis of Angelman and Prader-Willi Syndrome based on allelic methylation differences at the SNRPN locus" *Eur J Hum Genet* 5: 94-98.

Berry-Kravis, E., et al, 2007 "Fragile X-Associated Tremor/Ataxia Syndrome: Clinical Features, Genetics, and Testing Guidelines," *Movement Disorders*, 22; 2018-2030.

Coffee, et al 1999 "Acetylated histones are associated with MFR1 in normal but not fragile X-syndrome cells" Nature *Genetics* 22: 98-101.

Cornish, K., et al. 2006 "The Fragile X Continuum: New Advances and Perspectives," *Journal of Intellectual Disability Research*, 52: 469-482.

Dahl, C. et al. 2007 "A Homogeneous Assay for Analysis of FMRI Promoter Methylation in Patients with Fragile X Syndrome" Clinical Chemistry 53: 790-793.

Feng, et al. 2010 "Conservation and divergence of methylation patterning in plants and animals" *Proceedings of the National Academy of Sciences* 107:19, 8689-8694.

Genbank Accession No. NG_007529.1, dated Apr. 10, 2008.

Gheldof, N., et al. 2006 "The Active FMR1 Promoter is Associated with a Large Domain of Altered Chromatin Conformation with Embedded Local Histone Modifications," *Proceedings of the National Academy of Sciences*, 103: 12463-12468.

Godler, D.E., et al., 2011, "FMR1 Intron 1 Methylation Predicts FMRP Expression in Blood of Female Carriers of Expanded FMR1 Alleles," *Journal of Molecular Diagnostics*, 13: 528-536.

Godler, D.E., et al., 2010, "Methylation of Novel Markers of Fragile X Alleles is Inversely Correlated with FMRP Expression and FMR1 Activation Ratio," *Human Molecular Genetics*, 19: 1618-1632.

Hansen, et al 1992 "Methylation analysis of CGG sites in the CpG island of the human FMR1 gene" *Human Molecular Genetics* 1:8, 571-578.

Irizarry, R.A. et al. 2009 "The human colon cancer methylome shows similar hypo- and hypermethylation at conserved tissue-specific CpG island shores" *Nature Genetics* 41: 178-186.

Khalifa, M.M. et al. 1990 "Methylation Status of Genes Flanking the Fragile Site in Males with the Fragile-X Syndrome: A Test of the Imprinting Hypothesis" *American Journal of Human Genetics* 46: 744-753.

Kumari, D., et al., 2010, "The Distribution of Repressive Histone Modifications on Silenced FMR1 Alleles Provides Clues to the Mechanism of Gene Silencing in Fragile X Syndrome," *Human Molecular Genetics*, 19: 4634-4642.

Li, et al 2002 "MethPrime: designing primers for methylation PCRs" *Bioinformatics* 18:11, 1427-1431.

Michels, K. 2010 "The promises and challenges of epigenetic epidemiology" *Experimental Gerontology* 45: 297-301.

Oberlé, I. et al. 1991 "Instability of a 550-Base Pair DNA Segment and Abnormal Methylation in Fragile X Syndrome" *Science* 252: 1097-1102.

Oostra, B.A., et al. 2001 "Diagnostic Tests for Fragile X Syndrome," *Expert Review of Molecular Diagnostics*, 1: 226-232.

Panagopoulos, et al 1999 "A methylation PCR approach for detection of fragile X syndrome" *Human Mutation* 14: 71-79.

Pietrobono, R., et al., 2002, "Quantitative Analysis of DNA Demethylation and Transcriptional Reactivation of the FMR1 Gene in Fragile X Cells treated with 5-Azadeoxycytidine," *Nucleic Acids Research*, 30: 3278-3285.

Schwemmle, S., et al., 1997, "Characterization of FMR1 Promoter Elements by In Vivo-Footprinting Analysis," *Am. J. Hum. Genet.*, 60: 1354-1362.

Tassone, F., et al., 2003, "Expression of the FMR1 Gene," *Cytogenetic and Genome Research*, 100: 124-128.

Warren, S.T., 2007, "The Epigenetics of Fragile X Syndrome," *Cell Stem Cell*, 1: 488-489.

Weinhausel, A., et al., 2001, "Evaluation of the Fragile X (FRAXA) Syndrome with Methylation-Sensitive PCR," *Human Genetics*, 108: 450-458.

Wittenberger, et al. 2007 "The FMR1 premutation and reproduction" *Fertility and Sterility* 87:3, 456-465.

Zhou, Y., et al., 2006, "Simplified Molecular Diagnosis of Fragile X Syndrome by Fluorescent Methylation-Specific PCR and GeneScan Analysis," *Clinical Chemistry*, 52: 1492-1500.

Zhou, Y. et al. 2013 "Robust fragile X (CGG)$_n$ genotype classification using a methylation specific triple PCR assay" *J Med Gen* 41: e45.

* cited by examiner (B, continued)

(B, continued)

(B, continued)

(B, continued)

(B, continued)

(C, continued)

(D, continued)

SEQUENCE LISTING

```
<160> NUMBER OF SEQ ID NOS: 63

<210> SEQ ID NO 1
<211> LENGTH: 326
<212> TYPE: DNA
<213> ORGANISM: Homo sapiens

<400> SEQUENCE: 1
tttttcttac acaggcattg taaaggatgt tcatgaagat tcaataacag ttgcatttga      60
aaacaagtaa gtgtctcgtt atattatttt aatgatgagg ttctttaata ttttatgcta     120
attctattct tcattttta aaaattcaag tccagtttga gtgcttttca ggaatggatc      180
ttcatgttac tgactgagaa gtttctgaac aactcagtat taaactaatg gaatgactgt     240
ttctgctaat gtcctggagg tcccttattg tatggtattg atccttacgt cttaattccc     300
ttgaatgtga agaaagaaac cagaga                                          326

<210> SEQ ID NO 2
<211> LENGTH: 3556
<212> TYPE: DNA
<213> ORGANISM: Homo sapiens

<400> SEQUENCE: 2
agtaagtgtc tcgttatata attttaatga tgaggttctt taatatttta tgctaattct      60
attcttcatt ttttaaaaat tcaagtccag tttgagtgct tttcaggaat ggatcttcat     120
gttactgact gagaagtttc tgaacaactc agtattaaac taatggaatg actgtttctg     180
ctaatgtcct ggaggtccct tattgtatgg tattgatcct tacgtcttaa ttcccttgaa     240
tgtgaagaaa gaaaccagag agtcttgtgt attagtaact ggaagttcgc ataggagtat     300
ttgtaaattt taaaagata gtaatgaaaa gattcatggg tattgctaaa aagttgtatg     360
tgagttcttt aacattaaat ctaaaactga tggttttagt tgtctagtat attttatgga    420
aacagtcatg tttacctatt atctgatttt ttttaatgtt tcatatgttc agcaatagca    480
gtagctgatc ttttctgttc tcttttgcta gatgaagaaa taaaaacagt cataggccta    540
ggaatattaa ctgtatgaaa gcatcaatag tatagatgtt aacattttat tggagaacac    600
aagtctcttg actaaatgtt ttgaatgcta ataaaggcta ttttcagggt agctgttggt    660
aagattgtaa agtacatata aactccttag tcaaagtgta gatgtggcta tgatcttagg    720 atttactaa actctgatgg atggttaaca gttatcattt ttttggctct tatataccaa     780
gaaaattaat aatatatcaa aagcaggctg caaatctata gagacagaaa gtagattagt    840
```

```
gattgcttgt gctggggctg gtggggagaa catagctaaa gagtacagga ttttttgtgtg    900
tgtggcaatg aaaatgttgt aaaattgact ggtaattatt gcacataact gtaaaccttc    960
tataaaccat tgaattgtac atttaaattg atgaattata atgatatgtg gattatgtct   1020
gctaaaatgt agtatgtgac ccaggcatac tgagcaataa atacacacat cttgcttcta   1080
aagtttaaaa ccaggcctgt gtttcagtgt ctagaaaata tatttcataa ttgaacttag   1140
cagattcttt tggctagcaa caggacaaag tagtatcctt agatgcctga aacacgtgta   1200
gggggacaga gataaaagga ttaaaagcat ctaaccctat ttctggctct ggactaataa   1260
tcgcagacca aaatacaagt ttgaatagta gaataccttt ccctgaatac ataaagccaa   1320
aagttttagt atttgtctct tcgctgtttc atatatccat ggctatgcaa tagacaacag   1380
catcacacca acagaggaat ctttgataac ttggagggta tttttttctt acaattatac   1440
actttatcta cttacttaca tcactaggta aatgctgttt cccataaagg gagagttgtc   1500
tttatttgct actcttttag ttttttcctgt agtctataat ctaaagtgtt aagcaaacac   1560
tcatttcctc tatgcattta agaatttgtc tagtttatac attgatttat tagatcactt   1620
cttttttaatt ttcaatcaga tttctaccat aaacttaaaa ttatttcatc tttggacctt   1680
ccaattattt atctcctgta ccatatctgc atgaaagttt ctcttcaagc tctttgtcat   1740
cctgggagtt tgaaatagat cattgatttt cccttgtgtt catggagtat gtttgcaata   1800
caacactggg tttgagcaca tcaataggat ttaataggtc tccaccaaag taatctcttt   1860
gcccttcctt gtgtgtttcc ttttggttt tctgttagaa acaaaacgaa aacagtgttt   1920
tgtaaaacac cagattgtat ttacccttc tttcctttca atcaggaaga agctcctgtt   1980
actgatagca gattgtttta ggtgctttgt ttttaggtgc ttcctaaacc ttccataaag   2040
cataaaggtg ttttcatatt tcacattttt taataaggaa tttgaatttt tatctgtata   2100
cacttaaaat cattattttt tccttggaac cattgagtta tatattatta tatgctttaa   2160
aatcaaattt agcaatgaat gtataacatc tattaggtgt gtataataac tcagaggagg   2220
gttcagttaa tttaggcccct aatcagattt ccacaaattc tgacttaata tttgcccgct   2280
tatataacag ctcttcttta acaaaaacaa gtacttttct caatagaatt ttactaagaa   2340
agctctttag taaaacatcg acattataca tacaacatat ctcagtatct gctgatgaag   2400
aacaccaaaa agaacccaga tgtgactgct ccggaagttg aatcctcagt attttttgcaa   2460
agtttgtctt tcagtatttt atttgtgtgt gtgtgtgtgt gtgtgtgtgt gtgtgtctat   2520
atatatatat attttttttt ttttaaagac aggatctcac tctgtcacct aggctggagt   2580
gcagtggcat gatcatggct cactgtaacc ttgaactcct gagcttgagc tatcctccca   2640
cctcagcctc ccgagtagct gggactatag gcacatacca ctgcacctaa tttttttttt   2700
tttttaataa tttgttgtaa agatcaggtc ttaccttgtt gcccaggctg ctcttgaagt   2760
cctggcctga agcagtgctc ccacctcagc ctcccaaagc tctgggatta taggcttgag   2820
ccaccgcatc ctaatatttt atattttat ggatataaaa aataaatttgg tatctttcag   2880
agttgtttaa tatcatttta aatttaaaaa cataggcaac ttaaactcct ataggctgtc   2940
tccatcgggt ttctgtggtt taggagaccc caccatccca gtgcatgctg ataacgtcat   3000
actgatcagc atccagctac ccacagcaag aattgaccac ctcgtgggat ctaaaattta   3060
aaggggggaaa agtgagttgt gaattgctaa tgtgctgata gccccatttt gcttgggaat   3120
tagagggcag ttttttgtggt ccttggaatg tggttaaaat tcttctgcaa gtggaagcat   3180
atttatatta ctaacaatta ctggtactaa tattcaaata ttgaaggaaa tttctgttgt   3240
```

-continued

```
ggacttatgt ttaaagctct tagaagttga aattattgga aagaagactt gttttgaaaa      3300
tcataatgtt gctgtattgt gtttagagaa atattccaaa cgggagtagg ctgctgtgct      3360
gcatgcagac tttgctgaaa tgttactata ttgccgttat gtcccactca gcaaaaactg      3420
atgattttaa agcttttgct tcttgaaact agaaaaagag gggtcagcct taaccaaaag      3480
ttgatggcag agtggtcatt atttcagtta aacatgaaaa gcatgttaaa taattgtatg      3540
tttgcttatt tacagc                                                     3556

<210> SEQ ID NO 3
<211> LENGTH: 9703
<212> TYPE: DNA
<213> ORGANISM: Homo sapiens

<400> SEQUENCE: 3
gtacttggct ctagggcagg ccccatcttc gcccttcctt ccctcccttt tcttcttggt        60
gtcggcggga ggcaggcccg gggccctctt cccgagcacc gcgcctgggt gccagggcac       120
gctcggcggg atgttgttgg gagggaagga ctggacttgg ggcctgttgg aagcccctct       180
ccgactccga gaggccctag cgcctatcga aatgagagac cagcgaggag agggttctct       240
ttcggcgccg agcccgccg gggtgagctg gggatgggcg agggccggcg gcaggtacta       300
gagccgggcg ggaagggccg aaatcggcgc taagtgacgg cgatggctta ttccccctttt      360 cctaaacatc atctcccagc gggatccggg cctgtcgtgt gggtagttgt ggaggagcgg       420
ggggcgcttc agccgggccg cctcctgcag cgccaagagg gcttcaggtc tcctttggct       480
tctcttttcc ggtctagcat tgggacttcg gagagctcca ctgttctggg cgagggctgt       540
gaagaaagag tagtaagaag cggtagtcgg caccaaatca caatggcaac tgattttag       600 tggcttctct ttgtggattt cggaggagat tttagatcca aaagtttcag gaagaccca       660 acatggccca gcagtgcatt gaagaagttg atcatcgtga atattcgcgt cccccttttt      720
gttaaacggg gtaaattcag gaatgcacat gcttcagcgt ctaaaaccat tagcagcgct       780
gctacttaaa aattgtgtgt gtgtgtttaa gtttccaaag acctaaatat atgccatgaa       840
acttcaggta attaactgag agtatattat tactagggca tttttttttt aactgagcga       900
aaatattttt gtgcccctaa gaacttgacc acatttcctt tgaatttgtg gtgttgcagt       960
ggactgaatt gttgaggctt tatataggca ttcatgggtt tactgtgctt tttaaagtta      1020
caccattgca gatcaactaa caccttttcag ttttaaaagg aagatttaca aatttgatgt      1080
agcagtagtg cgtttgttgg tatgtaggtg ctgtataaat tcatctataa attctcattt      1140 cctttttgaat gtctataacc tctttcaata atatcccacc ttactacagt attttggcaa      1200
tagaaggtgc gtgtggaagg aaggctggaa aatagctatt agcagtgtcc aacacaattc      1260
ttaaatgtat tgtagaatgg cttgaatgtt tcagacagga cacgtttggc tataggaaaa      1320
taaacaattg actttattct gtgtttacca attttatgaa gacatttgga gatcagtata      1380
tttcataaat gagtaaagta tgtaaactgt tccatacttt gagcacaaag ataaagcctt      1440
ttgctgtaaa aggaggcaaa aggtaacccc gcgtttatgt tcttaacagt ctcatgaata      1500
tgaaattgtt tcagttgact ctgcagtcaa aattttaatt tcattgattt tattgatcca      1560
taatttcttc tggtgagttt gcgtagaatc gttcacggtc ctagattagt ggttttggtc      1620
actagatttc tggcactaat aactataata catatacata tatatgtgtg agtaacggct      1680
aatggttagg caagattttg attgacctgt gatataaact tagattggat gccactaaag      1740
```

```
tttgcttatc acagagggca agtagcacat tatggccttg aagtacttat tgttctcttc    1800
cagcaactta tgatttgctc cagtgatttt gcttgcacac tgactggaat ataagaaatg    1860
ccttctattt ttgctattaa ttccctcctt ttttgttttg ttttgtaacg aagttgttta    1920
acttgaaggt gaatgaagaa taggttggtt gccccttagt tccctgagga gaaatgttaa    1980
tacttgaaca agtgtgtgtc agacaaattg ctgttatgtt tatttaatta agtttgattt    2040
ctaagaaaat ctcaaatggt ctgcactgat ggaagaacag tttctgtaac aaaaaagctt    2100 gaaatttta tatgacttat aatactgctg tgagttttaa aagtaaagca aaagtaaact    2160
gagttgcttg tccagtggga tggacaggaa agatgtgaaa taaaaaccaa tgaaaaatga    2220
actgctgtgg agaagtgtta catttatgga aaaagaaata ggaaccttgt tcatcaaatt    2280
gatagaaaag cttttaaaac taaacaaatc aaacaacttg agtataatgg aattcagact    2340
ttgatttgcc taacataacc accatatttg caaggacagc tctctatctt ctggtgttta    2400
ttcttaaaaa cttaaaagtt agatttagcg atcaccagag ccactacttt tatgcttagg    2460
tatttgtttg acttagaaaa aattggtcac gtgtaccact ttatagtgcc ctgcaggtgt    2520
taagatatga aggcactttg acttacacct cataaaatct ttacaaagta ttttctaaat    2580
gaataatgat gaaataaagt ctttattcta ggtgcatctg ccccacataa tttgttttct    2640
ttggactaga agttttgatg tgttgagaat ggtaatgaat taactccatt ttaaatgtag    2700
aatgcgtatc actccaatat gaatgcccta atgaatccta agatttgtag gttttgtgta    2760
ctagtatgaa aattactaaa gatggaaaaa tcacatgttg gagacataag atacaaacct    2820
ttttgttttc tgaaaataca acctctgatt tctgattcct tgttgtaata tggtgtaatt    2880
atactagatt gtaattttgt tgttagatta tacttttta agttcagtgt ttgaggacag    2940
actttcattt ggttagtagt attatggcag ctagcagcta aatatgataa agtgtacaat    3000
caaaaggata ttttaatga agatattagt ggtctaacat gtcatttcag atacatagct    3060
gaaatgtagt aaaatcagtt ttactacaaa taaacttgca taaggtttat aaatttataa    3120
gtttataaat caacttgggt aaagtgtaaa taaacttgca ctcgtggttt ctctgaagtc    3180
tcctgagcta actttgcata aaggtgttat tctgtacttc gaggaagtga attattgggg    3240
tcaaccacat ttttttttcct tcctacagtc tgattgccct tttagttttt taggatcttt    3300
gtggctgcat catttttccc cttttgaact gtgcattttc taaccccata cttaaatatt    3360 ctcataaccct ccaaattatt aattagatgc aacattcagt ggtatattac tggagtttct    3420
gatttctgcc cactatagga atgtgcttcc tgagaagatt gggatcgtga ttataataat    3480
agttaacagg ggatgagtac tttctaggtg ccaggcactg ttctctctga tactttattt    3540
gatgtattgt tgttattccc attctttaaa tgatgcacag agaggttagg taagtgactt    3600
actaccaagt gtcagggcca ttaagggtca ggattctgaa ttcctgaaat gatgaaattt    3660
agcttgaaga aattggtttg atttcctgct tagttttcaa tttcatggtg gtctttgatt    3720
gtattttgtg ctataacact gccttagcat cctataacta tagttacagt gttatattac    3780
cattttttat tgttaataca aagccatcat gaataattc agtttatgtg ccagcttttt    3840
ttgttactaa ttcttgaacc ttggcgctgt acttcttcat gtggatgcct gttaaggaaa    3900
gataaagtta gaaatctttg accctgctag gaaatttgtc tttgttatat tgggagctca    3960
taaaactgaa gtattcaaaa gttagaatac atacacacaa gaaaaattag taactaattt    4020
aataatgttt tctttgcaca tgtctctgtt gtctttggt cagagtgaag ctaaatgtgt    4080
ttttcacata atttgtagcc tatatgaagt cctggacatg tggtatggtt ggaaggactg    4140
```

```
ttgatgaggt ttattgtctc tctttattct tttatgttgt tagtgtcccc atacaacggg    4200
gcggggggag tggggacaaa atgataactt gctttatata tgaagccttg ggtttgaatc    4260
atactgttat cacatttcct atgtccctat cctgtctcct gcaggttttc tttcttggtt    4320
ttcttttttg gttttctttc ttcctttctt cctttctttt cctttcttte ctttcttcct    4380 tttttctttc cttttctttt ttcctttctt tccttcattt ctctcctttg ctcctttagt    4440
ttgtttcttt gtttctttgg tttgtttctt tgtttctttg gtttgtttct ttgtttcttt    4500
agtttgtttc tttgtttctt tgtttctttc aacaggtctc actgtcgccc aggttggagt    4560
gcagtggtgg gatctcagct cactgcaacc tccacctctc gggttcaagc cagtctcatg    4620
cttcagcctt ccgggtagct gagattacag gcatgtgcca ccattcctgg ctattttttg    4680 cattttagt agagatgagg tttcgccatg ttggccaggc tgatctcaag ttatctgcct    4740
gcctcagccc tccaaagtgc tggaattaca ggcatgagac accgggtcca gcttccagca    4800
ggttttcttt aggagggata ttttacaatg ctgtaagttt ttcctaacga gaattatcat    4860
agcactacat gttctgtctt cagtaagtga tacaagctta ctgatgatgt tgtagttatg    4920
ttcattggtg gtcgggtgta cattgaaact ttaacacata atagcctctc ctgtgagcag    4980
tggttcctgt tggtaagata cttttactaag ggaaggaatg tgaggtgtcg ctggggagag    5040
tttacccaaa taaggatgga cttttctgtct ttgtttcatc agtcctggta atagaatgtt    5100
tgaatagata gctctaggca ttacatactt tcataaatat gattattgta attacctctt    5160
tggcccagtt gctagtaaat tagggacccc ttaatgattt atttcctgtt tattcaccct    5220
gatgaagaac ttgtatctct tttaaactgt actttatcgc ctttctcaaa ttccaagatt    5280
ctcatcacat ttttttttctt cccaaactct aaataacctt ttaatattaa gtatctttgt    5340
ggaaacattg ttttctttt ctatcccaat ttttaaagct tttttaaaaa aagagtgct    5400 tttgttggga tgtacatttt ccaaatgcaa aaacatttat gattctgtgt ctcttataaa    5460
atatgacact ctctactttt ctctcatttta tttagtgcca cctatgtgtg taatttcatt    5520
acccacagca gtcttaggag gctggtcgag ttccttattt gcagatgagg aatctgaggt    5580
ccagagatca cttcttggtg agagtctcac agctattaag tattagagcc aagatttga    5640 acgtaggtct gattcacagc aaaaccgtta accactaagt acactgactc cagtaagagc    5700
cctagtcctc acccaataca ctttaattcc cctgtgcatt cattcaaatt cattgaattt    5760
gctgcctttg gaaacctctc aggaacctcc tcaacctctc ttctctacag acatcagctt    5820
tgcctgatag gtagggatca tagcaaaaca cagttttcca aggtggtgat aggtggagtg    5880
atagtgctct ggagatggcc aaagaaggaa ggtatgagtg tatctgtggg tgggtgagtg    5940
gtggataagg ggaaggacag agccaaaagc gacggctatt ggaaaaacta tgatgagaaa    6000
caggaagatg gaaccttgtt ggaattagtg aaagaccttag aattcacag gaggtatttg    6060 tccttcacgc gagtgtagac caaacgtaac ctatgagttt cttttattcc acttattaaa    6120
gcagcaacca aaggtattat ataccttctg tattcactta aaatgactga tttttgaaaaa    6180 gtcatgcaaa catccatttta cagataagcc tcattaactc aaaggcagtg gccctgttgg    6240
gctctgatga ttactcaaac catttctgac actctgacac tacatccgga aatcatccgg    6300
aaatgcattc agagcctgca aaagcttttt ttttttttttt tttttttttt gaatagctac    6360
agcacttgca gatcttcctc ctttgagaga atatttgatt ttaggaaata agcaaatgta    6420
gataagtatg attcaactgg gcaataactt ttaggcaaag agaaaaaac aaaatatagc    6480
```

```
aatgtagtaa taaggctgat attatagtgc ttttatgatg agtctgaaaa cagtctccaa    6540
catttgtaaa tgttttaaat cgggtctgtc tactacagta gcccttaagc catatgtagc    6600
tattgagcac ttgacatgtt gcaagagtga attggagact gattttaatt ttatttaatt    6660
ttaatgtaag tagtcgcaca tgacccgtgg ctactatggt agatggcata gttttagaca    6720
agggcagtag tcttgggtag atacttgatt tacttagaac atttctttac ctagctgtaa    6780
caaggttcta atagctgatt aaaggacaac attttttagca tgtaatatac agtaaggaac    6840
taatgttaat tactgccaag atgtataaac attatgaaac cttaaacaag gatgaacaca    6900
gaagcagtgg cccttctttg taaataaggg gtcagttact tcctaatagg tgtcttagtt    6960
ttagttaata atctaatagc accccaaaa agcaaactgt taatttgtta ttagccatcc     7020
tgtaaagaca agggagaaat cggggccagg agagtcctct ttcccattct ccataatttt    7080
tacgacctat agaaataaga gcctaagagt gaccagttcc tgcaacctaa ctcaaaatta    7140
ggcctctctg ttgaagtaat agtgaggcaa acaatccctt gaagcactgg ggcatgcacc    7200
cttatgaaat ctaataattc taaaatatca ttggcagtat taagctagag ttctcaaaat    7260
atgctgtaga aaatattggt catttaaata tagctgagta aaaataagca agatcaaaat    7320
gataagaaaa tgttgatttc tcccctttg aaccagtaac taactataag ggtatatacc      7380
catgcttaac ttaaaaataa ttatttagcc accttgggta tagcacaaca tatggatgcc    7440
attatagtcc accttgatct tacaaggaag cttttctttta gcgtagcttt acttttattt    7500
aagcattatt gaagaagctt ggtatctctg tttaagttgc ttctgtatca gtgttttcca    7560
gggccctgtc tcagcttcca tagttttcct taagagcagc taattaatgc ttcactccat    7620
atgctttaat ttgatatttt gggaagtttc attttttaaa ataatctttt tatatcatag    7680
gcctttgaag acatatttgt ttacaaagac atctgcattg aaccatttgt ttttaaaaac    7740
atgtatcggg catgtcctat ataccagaaa ctatgccatt tactgaggac accgaagtta    7800
gagaatggtc ttaatccgaa ctagttattg tctcactatc caatatggat atcaaacatt    7860
cagcgtcatg aggatttact actgtgtttt ctcccaagag ttttataatt ttagctctta    7920
tatttaggtc tttgatgcat attcattgat tttttttgt atgcagtatg aggtaaaggt       7980
tgaaacgtat tctttttgca tgtgggtgtc cacttgtccc agcttcattt tttgaaaaca    8040
ctatactttc cccattgaat tgtcttggct tctttgttga caaaggattt attatttctg    8100
ccacaaccca gctgtttctc actgtctaaa cctttatgcc tgctgccccg taggcttagt    8160
ggaatgcctc tccatcctcc actctctttt gtttagctag tacttcctta tccttttaagg   8220
ggtcagtagg aacctcacct tcttcagtat gttttccttt gtcttatcaa cctaccacca    8280
tcacccacac atatcctttt tccctaaggc tgggatagga acctcttagg caatgatcta    8340
tttgataagt actcactgag ttcatactag acactctgca gtatatccgt aaatgaagta    8400
aaacctgaca ccaccctcag aaaacttact gttagtgaga aaatgggcta taataataga    8460
gtggggtaag tttattgtag ggataagcat aggatgctat gagaatgcag aggacaggaa    8520
tttaacctag acttctcagt tctcccgttg aagttgacat ctgaactgaa atctggaaga    8580
ccagtaagag atagctatgt aaaaagaggg gaaggacaat aggaaagaag gaatggagag    8640
aggcccagaa actacagagt atggcacaag tagtttagca ttgttgggtc acaaattcta    8700
aggatatgaa agataaagtt gaagaagtgg tggggctggg gaggacagct cctgtagagc    8760
cttttacagc gggagaagga gtttggctat ggtcctgcag gcaggagaa accactgaag     8820
gggagaaaca tacagaataa atttgagtaa gaagcttaaa tctccccaag ccctttaaa     8880
```

```
ataaattaag atataaagcc tttgggtttc tttatgcttt gtcctattct tctaattgtc    8940
caaaacaaaa caaaaacctt cctttctgt  acctattaaa aggttaattt tataaagtta    9000
cagacagcat gctgattaaa gaattcttga taattagcta ttttgtctgt ctttgtgtag    9060
attactaaca attgtgtcat cagatttaaa agatctaaac ctctggactt tatatatttt    9120
ttctacaagt actgtgagat tgagaactta attcaactct agtaactgga ctttttagtg    9180
ttgtttgcag catatgattg ttaaagaaag tttagtatat ttgtgtgtgc gtatatatat    9240
atatatagat agatagatag atttgaggtt atatttaatc attgactatt ggtattctaa    9300
gattttaagg agagaaaggt aggttacaat atatggctga tatatggttc tggaacaatt    9360
ttcttagttt tcagtaattc tacctaaaat gtacgtccag ctttgcactc actaccacat    9420
tgtaatttcc agtatacttg tctatttttc gagatgttga aatctgtgga gaatttttc     9480 tcatgtttag tgttttagct atgtttatct ctagggtata gcacatacaa ggtggcaata    9540
tagatgtgct taatgaataa aatgatcttc aaaaactgac cttcatttga agttctattt    9600
tattcataaa cacataaaac gtttggtatc actgtaaaat ttaactaaaa acaaaaacta    9660
tctttaagct cacaagttaa tttaacgttt tttcttacac agg                      9703

<210> SEQ ID NO 4
<211> LENGTH: 497
<212> TYPE: DNA
<213> ORGANISM: Homo sapiens

<400> SEQUENCE: 4
tgggcctgtt ggaagcccct ctccgactcc gagaggccct agcgcctatc gaaatgagag     60
accagcgagg agaggttctc tttcggcgcc gagtccccgc cggggtgagc tgggatgggc    120
gagggccggc ggcaggtact agagccgggc gggaagggcc gaaatcggcg ctaagtgacg    180
gcgatggctt attccccctt tcctaaacat catctcccag cgggatccgg gcctgtcgtg    240
tgggtagttg tggaggagcg ggggggcgctt cagccgggcc gcctcctgca gcgccaagag    300
ggcttcaggt ctccttttggc ttctctttttc cggtctagca ttgggacttc ggagagctcc    360
actgttctgg gcgagggctg tgaagaaaga gtagtaagaa gcggtagtcg gcaccaaatc    420
acaatggcaa ctgattttta gtggcttctc tttgtggatt tcggaggaga ttttagatcc    480
aaagtttcag gaagacc                                                   497

<210> SEQ ID NO 5
<211> LENGTH: 303
<212> TYPE: DNA
<213> ORGANISM: Homo sapiens

<400> SEQUENCE: 5
caagagggct tcaggtctcc tttggcttct cttttcctgg tctagcattg ggacttcgga     60
gagctccact gttctgggcg agggctgtga agaaagagta gtaagaagcg gtagtcggca    120
ccaaatcaca atggcaactg attttagta  gcttctcttt gtggatttca gagaagattt    180
tagatccaaa agtttcagaa agaccctaac atgcccagca gtgcattga  agaagttgat    240 catcgtgaat attcgcgtcc cccttttgt  taaacgggga aattcaggaa tgcacattgc    300
ttc                                                                  303

<210> SEQ ID NO 6
<211> LENGTH: 35
<212> TYPE: DNA
```

<213> ORGANISM: Homo sapiens

<400> SEQUENCE: 6
aggaagagag ggttttttg aaattttgg attta                           35

<210> SEQ ID NO 7
<211> LENGTH: 56
<212> TYPE: DNA
<213> ORGANISM: Homo sapiens

<400> SEQUENCE: 7
cagtaatacg actcactata gggagaaggc ttaaaaccta ttaaaaaccc ctctcc   56

<210> SEQ ID NO 8
<211> LENGTH: 35
<212> TYPE: DNA
<213> ORGANISM: Homo sapiens

<400> SEQUENCE: 8
aggaagagag taagagggtt ttaggttttt tttgg                         35

<210> SEQ ID NO 9
<211> LENGTH: 59
<212> TYPE: DNA
<213> ORGANISM: Homo sapiens

<400> SEQUENCE: 9
cagtaatacg actcactata gggagaaggc taaaacatat acattcctaa atttacccc  59

<210> SEQ ID NO 10
<211> LENGTH: 40
<212> TYPE: DNA
<213> ORGANISM: Homo sapiens

<400> SEQUENCE: 10
aggaagagag tttttttat ataggtattt gtaaaggatg                     40

<210> SEQ ID NO 11
<211> LENGTH: 59
<212> TYPE: DNA
<213> ORGANISM: Homo sapiens

<400> SEQUENCE: 11
cagtaatacg actcactata gggagaaggc ttctctaatt tctttcttca cattcaaaa  59

<210> SEQ ID NO 12
<211> LENGTH: 10
<212> TYPE: DNA
<213> ORGANISM: Homo sapiens

<400> SEQUENCE: 12
ggcgatggct                                                     10

<210> SEQ ID NO 13
<211> LENGTH: 10
<212> TYPE: DNA
<213> ORGANISM: Homo sapiens

<400> SEQUENCE: 13
tgaatattcg                                                     10

<210> SEQ ID NO 14
<211> LENGTH: 13

```
<212> TYPE: DNA
<213> ORGANISM: Homo sapiens

<400> SEQUENCE: 14
aagtttccaa aga                                                          13

<210> SEQ ID NO 15
<211> LENGTH: 10
<212> TYPE: DNA
<213> ORGANISM: Homo sapiens

<400> SEQUENCE: 15
tattattatt                                                              10

<210> SEQ ID NO 16
<211> LENGTH: 6
<212> TYPE: DNA
<213> ORGANISM: Homo sapiens

<400> SEQUENCE: 16 accaca                                                                   6

<210> SEQ ID NO 17
<211> LENGTH: 7
<212> TYPE: DNA
<213> ORGANISM: Homo sapiens

<400> SEQUENCE: 17 tgtggtg                                                                  7

<210> SEQ ID NO 18
<211> LENGTH: 7
<212> TYPE: DNA
<213> ORGANISM: Homo sapiens

<400> SEQUENCE: 18 tataaat                                                                  7

<210> SEQ ID NO 19
<211> LENGTH: 7
<212> TYPE: DNA
<213> ORGANISM: Homo sapiens

<400> SEQUENCE: 19 tataaat                                                                  7

<210> SEQ ID NO 20
<211> LENGTH: 8
<212> TYPE: DNA
<213> ORGANISM: Homo sapiens

<400> SEQUENCE: 20 aataatat                                                                 8

<210> SEQ ID NO 21
<211> LENGTH: 11
<212> TYPE: DNA
<213> ORGANISM: Homo sapiens

<400> SEQUENCE: 21
aaataaacaa t                                                            11

<210> SEQ ID NO 22
```

```
<211> LENGTH: 7
<212> TYPE: DNA
<213> ORGANISM: Homo sapiens

<400> SEQUENCE: 22 cataaat                                                                 7

<210> SEQ ID NO 23
<211> LENGTH: 7
<212> TYPE: DNA
<213> ORGANISM: Homo sapiens

<400> SEQUENCE: 23 tttgttt                                                                 7

<210> SEQ ID NO 24
<211> LENGTH: 7
<212> TYPE: DNA
<213> ORGANISM: Homo sapiens

<400> SEQUENCE: 24 tttgttt                                                                 7

<210> SEQ ID NO 25
<211> LENGTH: 7
<212> TYPE: DNA
<213> ORGANISM: Homo sapiens

<400> SEQUENCE: 25 ttgttta                                                                 7

<210> SEQ ID NO 26
<211> LENGTH: 16
<212> TYPE: DNA
<213> ORGANISM: Homo sapiens

<400> SEQUENCE: 26
tttatttaat taagtt                                                      16

<210> SEQ ID NO 27
<211> LENGTH: 7
<212> TYPE: DNA
<213> ORGANISM: Homo sapiens

<400> SEQUENCE: 27 aaacaaa                                                                 7

<210> SEQ ID NO 28
<211> LENGTH: 7
<212> TYPE: DNA
<213> ORGANISM: Homo sapiens

<400> SEQUENCE: 28 tataatt                                                                 7

<210> SEQ ID NO 29
<211> LENGTH: 12
<212> TYPE: DNA
<213> ORGANISM: Homo sapiens

<400> SEQUENCE: 29
tttatgctaa tt                                                          12
```

<210> SEQ ID NO 30
<211> LENGTH: 1520
<212> TYPE: DNA
<213> ORGANISM: Homo sapiens

<400> SEQUENCE: 30

```
taacatggcc cagcagtgca ttgaagaagt tgatcatcgt gaatattcgc gtcccccttt      60
ttgtaaacgg ggtaaattca ggaatgcaca tgcttcagcg tctaaaacca ttagcagcgc     120
tgctacttaa aaattgtgtg tgtgtgttta agtttccaaa gacctaaata tatgccatga     180
aacttcaggt aattaactga gagtatatta ttactagggc attttttttt taactgagcg     240
aaaatatttt tgtgccccta agaacttgac cacatttcct tgaattgtgg tgttgcagtg     300
gactgaattg ttgaggcttt atataggcat tcatgggttt actgtgcttt ttaaagttac     360
accattgcag atcaactaac acctttcagt tttaaaagga agatttacaa atttgatgta     420
gcagtagtgc gtttgttggt atgtaggtgc tgtataaatc atctataaat tctcatttcc     480
ttttgaatgt ctataacctc ttcaataata tcccaccttta ctacagtatt ttggcaatag    540
aaggtgcgtg tggaaggaag gctggaaaat agctattagc agtgtccaac acaattctta     600
aatgtattgt agaatggctt gaatgtttca gacaggacac gtttggctat aggaaaataa     660
acaattgact tattctgtgt ttaccaattt tatgaagaca tttggagatc agtatatttc     720
ataaatgagt aaagtatgta aactgttcca tactttgagc acaaagataa agccttttgc     780
tgtaaaagga ggcaaaaggt aaccccgcgt ttatgttctt aacagtctca tgaatatgaa     840
attgtttcag ttgactctca gtcaaaattt taatttcatt gatttttattg atccataatt    900 tcttctggtg agtttgcgta gaatcgttca cggtcctaga ttagtggttt tggtcactag     960
atttctggca ctaataacta taatacatat acatatatat gtgtgagtaa cggctaatgg    1020
ttaggcaaga tttgattgac ctgtgatata aacttagatt ggatgccact aaagtttgct    1080
tatcacagag ggcagtagca cattatggcc ttgaagtact tattgttctc ttccagcaac    1140
ttatgatttg ctccagtgat tttgcttgca cactgactgg aatataagaa atgccttcta    1200
tttttgctat taattccctc cttttttgtt ttgtttttgta acgaagttgt taacttgaa    1260 ggtgaatgaa gaataggttg gttgcccctt agttccctga ggagaatgtt aatacttgaa    1320
caagtgtgtg tcagacaaat tgctgttatg tttatttaat taagtttgat ttctaagaaa    1380
atctcaaatg gtctgcactg atggaagaac agttctgtta caaaaaaagc ttgaaatttt    1440
tatatgactt ataatactgc tgtgagtttt aaaagtaaag caaaagtaaa ctgagttgct    1500
tgtccagtgg gatggacagg                                                1520
```

<210> SEQ ID NO 31
<211> LENGTH: 237
<212> TYPE: DNA
<213> ORGANISM: Homo sapiens

<400> SEQUENCE: 31

```
tcgagatgtt gaaatctgtg gagaattttt ctcatgttta gtgtttagc tatgtttatc       60 tctagggtat agcacataca aggtggcaat atagatgtgc ttaatgaata aaatgatctt     120
caaaactgac cttcatttga gttctatttt attcataaac acataaaacg tttggtatca     180
ctgtaaaatt taactaaaaa caaaaactat ctttaagctc acaagttaat ttaacgt        237
```

<210> SEQ ID NO 32
<211> LENGTH: 30
<212> TYPE: DNA

<213> ORGANISM: Homo sapiens

<400> SEQUENCE: 32
gctcagctcc gtttcggttt cacttccggt                30

<210> SEQ ID NO 33
<211> LENGTH: 30
<212> TYPE: DNA
<213> ORGANISM: Homo sapiens

<400> SEQUENCE: 33
agccccgcac ttccaccacc agctcctcca                30

<210> SEQ ID NO 34
<211> LENGTH: 17
<212> TYPE: DNA
<213> ORGANISM: Homo sapiens

<400> SEQUENCE: 34
ccgcggaatc ccagaga                17

<210> SEQ ID NO 35
<211> LENGTH: 19
<212> TYPE: DNA
<213> ORGANISM: Homo sapiens

<400> SEQUENCE: 35
cagtggcgtg ggaaatcaa                19

<210> SEQ ID NO 36
<211> LENGTH: 17
<212> TYPE: DNA
<213> ORGANISM: Homo sapiens

<400> SEQUENCE: 36
tgggataacc ggatgca                17

<210> SEQ ID NO 37
<211> LENGTH: 20
<212> TYPE: DNA
<213> ORGANISM: Homo sapiens

<400> SEQUENCE: 37
acaccctgtg ccctttaagg                20

<210> SEQ ID NO 38
<211> LENGTH: 22
<212> TYPE: DNA
<213> ORGANISM: Homo sapiens

<400> SEQUENCE: 38
tcaaagctgg gtctgaggaa ag                22

<210> SEQ ID NO 39
<211> LENGTH: 17
<212> TYPE: DNA
<213> ORGANISM: Homo sapiens

<400> SEQUENCE: 39
tcgggatctc aaaatgt                17

<210> SEQ ID NO 40
<211> LENGTH: 21

```
<212> TYPE: DNA
<213> ORGANISM: Homo sapiens

<400> SEQUENCE: 40
ccccagaatg agaggatgtt g                                        21

<210> SEQ ID NO 41
<211> LENGTH: 21
<212> TYPE: DNA
<213> ORGANISM: Homo sapiens

<400> SEQUENCE: 41
gccctagatc caccgcttta a                                        21

<210> SEQ ID NO 42
<211> LENGTH: 14
<212> TYPE: DNA
<213> ORGANISM: Homo sapiens

<400> SEQUENCE: 42
tgctggtgga actc                                                14

<210> SEQ ID NO 43
<211> LENGTH: 27
<212> TYPE: DNA
<213> ORGANISM: artificial sequence
<220> FEATURE:
<223> OTHER INFORMATION: Forward primer FREE2 (D)

<400> SEQUENCE: 43 aaaagttttta ggaagatttt aatatgg                                 27

<210> SEQ ID NO 44
<211> LENGTH: 27
<212> TYPE: DNA
<213> ORGANISM: artificial sequence
<220> FEATURE:
<223> OTHER INFORMATION: Reverse primer FREE2 (D)

<400> SEQUENCE: 44
aaaaaacaca ataaacccat aaatacc                                  27

<210> SEQ ID NO 45
<211> LENGTH: 27
<212> TYPE: DNA
<213> ORGANISM: artificial sequence
<220> FEATURE:
<223> OTHER INFORMATION: Forward primer FREE2 (E)

<400> SEQUENCE: 45
gaatggtttg aatgttttag ataggat                                  27

<210> SEQ ID NO 46
<211> LENGTH: 26
<212> TYPE: DNA
<213> ORGANISM: artificial sequence
<220> FEATURE:
<223> OTHER INFORMATION: Reverse primer FREE2 (E)

<400> SEQUENCE: 46
accaaaaatc taataaccaa aaccac                                   26

<210> SEQ ID NO 47
<211> LENGTH: 327
<212> TYPE: DNA
```

```
<213> ORGANISM: artificial sequence
<220> FEATURE:
<223> OTHER INFORMATION: FREE3

<400> SEQUENCE: 47
tttttcttac acaggcattt gtaaaggatg ttcatgaaga ttcaataaca gttgcatttg      60
aaaacaagta agtgtctcgt tatataattt taatgatgag gttctttaat attttatgct    120
aattctattc ttcattttt aaaaattcaa gtccagtttg agtgcttttc aggaatggat     180
cttcatgtta ctgactgaga agtttctgaa caactcagta ttaaactaat ggaatgactg    240
tttctgctaa tgtcctggag gtcccttatt gtatggtatt gatccttacg tcttaattcc    300
cttgaatgtg aagaaagaaa ccagaga                                         327

<210> SEQ ID NO 48
<211> LENGTH: 374
<212> TYPE: DNA
<213> ORGANISM: artificial sequence
<220> FEATURE:
<223> OTHER INFORMATION: FREE2 (D)

<400> SEQUENCE: 48
aaaagtttca ggaagaccct aacatggccc agcagtgcat tgaagaagtt gatcatcgtg      60
aatattcgcg tccccctttt tgttaaacgg ggtaaattca ggaatgcaca tgcttcagcg    120
tctaaaacca ttagcagcgc tgctacttaa aaattgtgtg tgtgtgttta agtttccaaa    180
gacctaaata tatgccatga aacttcaggt aattaactga gagtatatta ttactagggc    240 atttttttt taactgagcg aaaatatttt tgtgcccta agaacttgac cacatttcct     300
ttgaatttgt ggtgttgcag tggactgaat tgttgaggct ttatataggc attcatgggt    360
ttactgtgct tttt                                                       374

<210> SEQ ID NO 49
<211> LENGTH: 360
<212> TYPE: DNA
<213> ORGANISM: artificial sequence
<220> FEATURE:
<223> OTHER INFORMATION: FREE2 (E)

<400> SEQUENCE: 49
gaatggcttg aatgtttcag acaggacacg tttggctata ggaaaataaa caattgactt      60
tattctgtgt ttaccaattt tatgaagaca tttggagatc agtatatttc ataaatgagt    120
aaagtatgta aactgttcca tactttgagc acaaagataa agccttttgc tgtaaaagga    180
ggcaaaaggt aaccccgcgt ttatgttctt aacagtctca tgaatatgaa attgtttcag    240
ttgactctgc agtcaaaatt ttaatttcat tgattttatt gatccataat ttcttctggt    300
gagtttgcgt agaatcgttc acggtcctag attagtggtt ttggtcacta gatttctggc    360

<210> SEQ ID NO 50
<211> LENGTH: 30
<212> TYPE: DNA
<213> ORGANISM: artificial sequence
<220> FEATURE:
<223> OTHER INFORMATION: Forward primer FREE3

<400> SEQUENCE: 50
ttttttttat ataggtattt gtaaaggatg                                       30

<210> SEQ ID NO 51
<211> LENGTH: 28
```

```
<212> TYPE: DNA
<213> ORGANISM: artificial sequence
<220> FEATURE:
<223> OTHER INFORMATION: Forward primer FREE3

<400> SEQUENCE: 51
tctctaattt ctttcttcac attcaaaa                                    28

<210> SEQ ID NO 52
<211> LENGTH: 10
<212> TYPE: DNA
<213> ORGANISM: artificial sequence
<220> FEATURE:
<223> OTHER INFORMATION: Tag forward primer FREE2 (D)

<400> SEQUENCE: 52
aggaagagag                                                        10

<210> SEQ ID NO 53
<211> LENGTH: 31
<212> TYPE: DNA
<213> ORGANISM: artificial sequence
<220> FEATURE:
<223> OTHER INFORMATION: Tag reverse primer FREE2 (D)

<400> SEQUENCE: 53
cagtaatacg actcactata gggagaaggc t                                31

<210> SEQ ID NO 54
<211> LENGTH: 10
<212> TYPE: DNA
<213> ORGANISM: artificial sequence
<220> FEATURE:
<223> OTHER INFORMATION: Tag forward primer FREE2 (E)

<400> SEQUENCE: 54
aggaagagag                                                        10

<210> SEQ ID NO 55
<211> LENGTH: 31
<212> TYPE: DNA
<213> ORGANISM: artificial sequence
<220> FEATURE:
<223> OTHER INFORMATION: Tag reverse primer FREE2 (E)

<400> SEQUENCE: 55
cagtaatacg actcactata gggagaaggc t                                31

<210> SEQ ID NO 56
<211> LENGTH: 10
<212> TYPE: DNA
<213> ORGANISM: artificial sequence
<220> FEATURE:
<223> OTHER INFORMATION: Tag forward primer FREE3

<400> SEQUENCE: 56
aggaagagag                                                        10

<210> SEQ ID NO 57
<211> LENGTH: 31
<212> TYPE: DNA
<213> ORGANISM: artificial sequence
<220> FEATURE:
<223> OTHER INFORMATION: Tag reverse primer FREE3

<400> SEQUENCE: 57
```
cagtaatacg actcactata gggagaaggc t                                31

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58
aggaagagag aaaagtttta ggaagatttt aatatgg                          37

<210> SEQ ID NO 59
<211> LENGTH: 58
<212> TYPE: DNA
<213> ORGANISM: Artificial Sequence
<220> FEATURE:
<223> OTHER INFORMATION: Primer

<400> SEQUENCE: 59
cagtaatacg actcactata gggagaaggc taaaaaacac aataaaccca taaatacc   58

<210> SEQ ID NO 60
<211> LENGTH: 37
<212> TYPE: DNA
<213> ORGANISM: Artificial Sequence
<220> FEATURE:
<223> OTHER INFORMATION: Primer

<400> SEQUENCE: 60
aggaagagag gaatggtttg aatgttttag ataggat                          37

<210> SEQ ID NO 61
<211> LENGTH: 57
<212> TYPE: DNA
<213> ORGANISM: Artificial Sequence
<220> FEATURE:
<223> OTHER INFORMATION: Primer

<400> SEQUENCE: 61
cagtaatacg actcactata gggagaaggc taccaaaaat ctaataacca aaaccac    57

<210> SEQ ID NO 62
<211> LENGTH: 40
<212> TYPE: DNA
<213> ORGANISM: Artificial Sequence
<220> FEATURE:
<223> OTHER INFORMATION: Primer

<400> SEQUENCE: 62
aggaagagag ttttttttat ataggtattt gtaaaggatg                       40

<210> SEQ ID NO 63
<211> LENGTH: 59
<212> TYPE: DNA
<213> ORGANISM: Artificial Sequence
<220> FEATURE:
<223> OTHER INFORMATION: Primer

<400> SEQUENCE: 63
cagtaatacg actcactata gggagaaggc ttctctaatt tctttcttca cattcaaaa  59

TREATMENT AND DIAGNOSIS OF EPIGENETIC DISORDERS AND CONDITIONS

FILING DATA

This application is a divisional of application Ser. No. 13/814,911, filed Feb. 7, 2013, which is the U.S. national phase of International Application No. PCT/AU2011/001024, filed Aug. 11, 2011, which claims priority from Australian Provisional Patent Application No. 2010903595, filed on Aug. 11, 2010, entitled "Treatment and diagnosis of epigenetic disorders and conditions," all of which, are expressly incorporated herein by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 28314004_1.TXT, the date of creation of the ASCII text file is Jun. 5, 2018, and the size of the ASCII text file is 31.8 KB.

FIELD

The present disclosure relates generally to the field of epigenetics and in particular epigenetic profiles associated with a pathological condition. The present specification teaches screening of individuals and populations for epigenetic profiles associated with a pathological condition. Kits and diagnostic assays are also taught herein as are computer programs to monitor changes in epigenetic patterns and profiles. Further enabled herein is a method for screening for agents which can reduce or mask the adverse effects of epigenetic modification and the use of these agents in therapy and prophylaxis.

BACKGROUND

Bibliographic details of the publications referred to in this specification are also collected at the end of the description.

Reference to any prior art in this specification is not, and should not be taken as, an acknowledgment or any form of suggestion that this prior art forms part of the common general knowledge in any country.

It is apparent that DNA methylation and other epigenetic modifications play a role in the regulation of gene expression in higher organisms. The importance of epigenetic modification has been highlighted by its involvement in several human diseases. Methylation, for example, of cytosine at the 5' position is the only known methylation modification of genomic DNA. In particular, methylation of CpG islands within regulatory regions of the genome appears to be highly tissue specific. Methylation of cytosines distal to the islands is also important. These regions are called "shores" or "island shores" (Irizarry et al., Nature Genetics 41(2):178-186, 2009). Epigenetic modifications include histone modification, changes in acetylation, methylation, obiquitylation, phosphorylation, sumoylation, activation or deactivation, chromatin altered transcription factor levels and the like.

Another genetic condition which can affect gene expression arises from expansion or increase in the number of repeats in a specific tandem repeat array. Such nucleotide expansion can result in repeat expansion disease conditions. A critical threshold of repeat expansion determines the level of pathologicity (Orr and Zoghbi, Ann Rev Neurosci 30:575-621, 2007). Many diseases arise from expansion of a repeat located in an open reading frame resulting in a protein with a long polyQ$^2$ tract that is toxic to neurons (Orr and Zoghbi, 2007 supra). Other expansion disease conditions such as Fragile X syndrome (FXS), Fragile XE mental retardation (FRAXE), Fragile X-associated primary ovarian insufficiency (FXPOI), Fragile type, folic acid type, rare 12 (FRA12A), mental retardation (MR), Friedrich's ataxia (FRDA) and myotonic dystrophy (DM), arise from altered transcription of the repeats which are not translated.

A particular type of expansion disorder is referred to as a trinucleotide repeat disorder (also known as trinucleotide repeat expansion disorder, triplet repeat expansion disorder and codon reiteration disorder) and results from trinucleotide repeats in certain genetic loci. An example occurs in the Fragile X Mental Retardation genetic locus ("FMR genetic locus").

The FMR genetic locus includes the FMR1 gene which is composed of 17 exons, spanning 38 Kb, and encodes Fragile X Mental Retardation Protein (FMRP), essential for normal neurodevelopment (Verkerk et al., Cell 65(5):905-914, 1991; Terracciano et al., Am J Med Genet C Semin Med Genet 137C(1):32-37, 2005). A CGG repeat segment is located within the 5' untranslated region (UTR) of the gene. Its normal range is <40 repeats. When expanded, these repeats have been implicated in a number of pathologies, including the Fragile X syndrome (FXS), Fragile X-associated Tremor Ataxia Syndrome (FXTAS) and Fragile X-associated primary ovarian insufficiency (FXPOI; formerly referred to as Premature Ovarian Failure [POF]). FXS is neurodevelopmental in nature with a frequency of 1/1400 males and 1/8000 females, associated with a Fragile site at the Xq27.3 locus (Jin and Warren, Hum. Mol. Genet 9(6): 901-908, 2000).

This syndrome is caused by a CGG expansion to "full mutation" (FM) which comprises >200 repeats, leading to a gross deficit of FMRP and subsequent synaptic abnormalities (Pieretti et al., Cell 66(4):817-822, 1991; Irwin et al., Cereb Cortex 10(10):1038-1044, 2000). The FXS clinical phenotype ranges from learning disabilities to severe mental retardation and can be accompanied by a variety of physical and behavioral characteristics. FXTAS is prevalent in ~30% of premutation individuals (PM), comprising 55 to 199 repeats (Nolin et al., Am J Hum Genet 72(2):454-464, 2003) and is a progressive neurodegenerative late-onset disorder with a frequency of 1/3000 males in the general population (Jacquemont et al., Am J Ment Retard 109(2):154-164, 2004), manifesting as tremor, imbalance and distinct MRI and histological changes (Hagerman et al., Neurology 57(1): 127-130, 2001; Jacquemont et al., J Med Genet 42(2):e14, 2005; Loesch et al., Clin Genet 67(5):412-417, 2005). It is often associated with 'toxicity' of elevated FMR1 mRNA, which has been linked to the intranuclear inclusions and cell death observed during neurodegeneration (Jin et al., Neuron 39(5):739-747, 2003).

FXTAS can occur in females carrying PM, but with much lower frequency as can be expected from X-linked inheritance. The intermediate or Gray Zone (GZ) alleles comprising 41 to 54 repeats (Bodega et al., Hum Reprod 21(4):952-957, 2006) are the most common form of the expansion, 1 in 30 males and 1 in 15 females. As with PM alleles, increased levels of FMR1 mRNA have been reported in the GZ individuals, proportional to the size of CGG expansion (Kenneson et al., Hum Mol Genet 10(14):14491454, 2001; Mitchell et al., Clin Genet 67(1):38-46, 2005; Loesch et al., J Med Genet 44(3):200-204, 2007). Female carriers of both PM and GZ allelic types have an increased risk of developing POF (Allingham-Hawkins et al., *Am J Med Genet* 83(4):322-325, 1999; Sullivan et al., *Hum Reprod* 20(2): 402-412, 2005) which has incidence of approximately 1% in the general population, and often unknown etiology (Coulam, *Fertil Steril* 38(6):645-655, 1982).

Expansion related abnormalities in FMR1 are involved in pathologies with a wide spectrum of patho-mechanisms all pointing to involvement of multiple factors at the Xq27.3 locus in addition to FMR1. A number of antisense transcripts have been described embedded within the FMR1 sequence, ASFMR1 (Ladd et al., *Hum Mol Genet* 16(24):3174-3187, 2007) and FMR4 (Khalil et al., *PLoS ONE* 3(1):e1486, 2008). The ASFMR1 and FMR4 transcripts have been suggested to share the bi-directional promoter with FMR1, which is heavily regulated by the state of the surrounding chromatin environment (Pietrobono et al., *Nucleic Acids Res* 30(14):3278-3285, 2002; Chiurazzi et al., *Hum Mol Genet* 7(1):109113, 1998).

Transcription of ASFMR1 is also regulated by another promoter located in the exon 2 of FMR1, with the resulting transcript spanning the CGG repeat in the antisense direction (Ladd et al., 2007, supra), and an open reading frame (ORF) with the CGG encoding a polyproline peptide (Ladd et al., 2007, supra). FMR4, however, is a long non-coding RNA, involved in regulation of apoptosis (Khalil et al., 2008, supra).

The length of the CGG repeat has been reported to effect transcription of all three genes FMR1, FMR4 and ASFMR1 (Ladd et al., 2007, supra; Khalil et al., 2008, supra). However, although it is well documented that FMR1 transcription is promoter methylation dependent, linked to the CGG expansion size, the relationship between FMR4 and ASFMR1 transcription and methylation remains elusive.

One of the current problems is in the diagnosis of subjects with FM in the FMR genetic locus. Diagnostic assays targeting only the CGG expansion have hitherto been inconclusive. Therefore, currently Southern DNA analysis, which is expensive and time consuming, is used as a gold standard assay for diagnosis in many laboratories.

Despite the availability of a range of methylation and nucleotide expansion assays (see, for example, Rein et al., *Nucleic Acids Res.* 26:2255, 1998 in relation to methylation assays), selection of regions to amplify and screen is an important aspect of determining an epigenetic profile characteristic of a disease condition. There is a need to identify crucial regions which are associated with epigenetic change linked to a pathological condition to assay and/or therapeutically target.

SUMMARY

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

Nucleotide and amino acid sequences are referred to by a sequence identifier number (SEQ IN NO:). The SEQ ID NOs: correspond numerically to the sequence identifiers <400>1 (SEQ ID NO:1), <400>2 (SEQ ID NO:2), etc. A summary of sequence identifiers is given in Table 1.

Aspects enabled herein are predicated in part on the determination of an association between epigenetic modification of intronic regions including intron/exon boundaries and splicing regions within a genetic locus and a pathological condition including a trinucleotide expansion disorder. In an embodiment, the epigenetic modification occurs in:

(i) two or more of (a) an intron; (b) an intron/exon boundary; and/or (c) a splicing region; and/or (ii) approximately one seventh or greater of an intron including an intron/exon boundary and/or a splicing region; within a genetic locus.

In an embodiment, the epigenetic modification occurs within a genetic locus which leads to a condition including a pathoneurological condition such as a pathoneurodevelopmental and pathoneurodegenerative condition as well as a non-neurological condition. Conditions and disorders including trinucleotide expansion disorders associated with a change in the epigenetic profile from that observed in healthy controls associated with a change in epigenetic profile in intronic regions including intron/exon boundary regions, include Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome. Reference to a "control" means relative to a healthy subject which means a subject with a normal size of expansion repeats and/or who is phenotypically normal meaning that the subject does not have symptoms of, for example, a trinucleotide expansion disorder and/or is the epigenetic (e.g. methylation) profile observed in healthy control subjects.

It is proposed herein that epigenetic changes in an intron, intron/exon boundary and/or splicing region within a particular genetic locus are associated with the development, progression and severity of a range of pathological conditions including trinucleotide expansions disorders such as but not limited to those listed above. In relation to the FMR genetic locus, the epigenetic modification may occur in:

(i) two or more of (a) an intron; (b) an intron/exon boundary; and/or (c) a splicing region; and/or (ii) approximately one seventh or greater of an intron including an intron/exon boundary and/or a splicing region; within the genetic locus. These regions also include promoter regions. Epigenetic changes may occur on either strand of double stranded genomic DNA including either strand of a promoter or other regulatory region and either strand may be targeted for epigenetic analysis. The ASFMR1 promoter is an example. The location of this promoter can be seen in FIGS. 6A and 6C and has a transcription start site in FREE3 of intron 2. Hence, another aspect of the present disclosure provides a method for identifying FXS or a related condition in a human subject, the method comprising screening for a change relative to a control in the extent of epigenetic modification in the FMR genetic locus at a location selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions; and (ii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

wherein a change in extent of epigenetic modification relative to a control is indicative of the presence or severity of the pathological condition or a propensity to develop same.

In an embodiment, a method is provided for identifying a trinucleotide expansion disorder in a mammalian subject including a human, the method comprising screening for a change relative to a healthy control in the extent of epigenetic modification within (i) two or more of (a) an intron; (b) an intron/exon boundary; and/or (c) a splicing region; and/or (ii) approximately one seventh or greater of an intron including an intron/exon boundary and/or a splicing region of the FMR genetic locus; wherein a change in extent of epigenetic modification relative to the control is indicative of the presence or severity of the trinucleotide expansion disorder or a propensity to develop same wherein the intron, intron/exon boundary and/or splicing region is selected from the list consisting of:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions; and (iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions.

By "epigenetic modification" is meant changes in extent, level and/or profile or epigenetic modification including changes in methylation including hypermethylation and hypomethylation, histone modification, acetylation, obiquitylation, phosphorylation and/or sumoylation, as well as changes in chromatin altered transcription factor levels and the like leading to activation or deactivation of genetic locus expression. The epigenetic modification extends to an increase or decrease in epigenetic change relative to a normal control. It also extends to either strand of these target regions which includes either strand of a promoter region. In an embodiment, epigenetic modification includes the methylation state of CpG and CpNpG sites within an intron of a genetic locus. In an embodiment, the genetic locus is the FMR genetic locus which includes FMR1, FMR4 and ASFMR1 genes. In an embodiment, the epigenetic modification occurs in the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 region alone or in combination with the FREE1 region (D) region or FREE2 (D)/(E) boundary.

These regions include either strand of a double stranded genomic sequence and includes either strand of the promoter region such as the ASFMR1 promoter with a transcription initiation site in FREE3 of intron 2.

Furthermore, the epigenetic profile of the FMR genetic locus is also informative as to the spectrum of disease conditions associated with the genetic locus, such as whether the subject is normal or has a PM, GZ or FM pathology and/or whether the epigenetic change and/or CGG expansion is heterozygous or homozygous at the FMR allele. Reference to "FREE2" include FREE2 (A), FREE2 (B), FREE2 (C), FREE2 (D) and FREE2 (E) including any exon/intron boundaries therein such as the FREE2(D)/ FREE2 (E) boundary. The boundary regions include a promoter region. A "promoter region" includes either or both nucleic acid strands within double stranded genomic DNA.

Accordingly, an aspect enabled herein is a method for identifying an epigenetic profile in the genome of a cell indicative of a pathological condition, the method comprising screening for a change relative to a control in the extent of epigenetic modification within (i) two or more of (a) an intron; (b) an intron/exon boundary; and/or (c) a splicing region; and/or (ii) approximately one seventh or greater of an intron including an intron/exon boundary and/or a splicing region of a genetic locus wherein the extent of epigenetic change relative to a control is indicative of the presence or severity of the pathological condition or a propensity to develop same.

In an embodiment, the epigenetic profile is determined within a genetic locus, the epigenetic profile of which, is associated with a pathological condition including a trinucleotide disorder associated with a change in epigenetic profile from that observed in healthy controls selected from Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome.

In an embodiment, the epigenetic change is within the FMR genetic locus and is associated with one or more of FXS, FXTAS, FXPOI, autism, mental retardation, a modified X-chromosome and/or cognitive impairment.

In relation to the latter aspect, the method comprises screening for a change relative to the control in the extent of epigenetic modification within the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including FREE2 (D) or FREE2(D)/(E) boundary. These regions may be assessed on either strand of double stranded genomic DNA and include either strand of a promoter region. An example of a promoter region is the ASFMR1 promoter with an initiation site in FREE3 of intron 2 (see FIG. 6).

The extent of epigenetic change is indicative of the presence of severity of the pathological condition or a propensity to developing same. As indicated above, a "pathological condition" includes a trinucleotide expansion disorder.

A further aspect taught herein is a method for identifying an epigenetic profile in the genome of a cell indicative of a pathological condition associated with the FMR genetic locus, the method comprising extracting genomic DNA from the cell and subjecting the DNA to an amplification reaction using primers selective for (i) two or more of (a) an intron; (b) an intron/exon boundary; and/or (c) a splicing region; and/or (ii) approximately one seventh or greater of an intron including an intron/exon boundary and/or a splicing region, within the FMR genetic locus including the FMR1 gene, subjecting the amplified DNA to an epigenetic assay to determine the extent of epigenetic modification of the DNA wherein a change in the extent of epigenetic modification is indicative of the presence or severity of the pathological condition or propensity to develop same. The region within the FMR genetic locus is selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

A similar method applies to epigenetic changes in other genetic loci. Reference to the "FMR genetic locus" includes the FMR1, FMR4 and ASFMR1 genes and corresponds to Xq27.3 as well as promoter regions associated with these sites. The term "FMR locus" means the "FMR genetic locus". In an embodiment, an aspect taught herein determines that the intronic region downstream of intron 1 comprises Fragile X-related Epigenetic Element 3 as defined by SEQ ID NO:1 or a homolog thereof or a portion or fragment thereof defined by having at least 80% nucleotide sequence identity to SEQ ID NO:1 or which hybridizes to SEQ ID NO:1 or its complementary form under medium stringency conditions; or is intron 2 as defined by SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions. The nucleotide sequence of intron 1 of the FMR1 gene is set forth in SEQ ID NO:3. The genomic nucleotide sequence of FREE2 region alone or in combination with the FREE1 region (D), FREE2 (E) and FREE3 are set forth in SEQ ID NOs:48, 49 and 47, respectively, and the present disclosure extends to homologs thereof having at least 80% identity to SEQ ID NO:48 or 49 or 47 or which hybridizes to SEQ ID NO:48 or 49 or 47 or a complement thereof under medium stringency conditions. The present disclosure further contemplates amplifying all or part of an expansion mutation and/or and detecting extent of epigenetic change therein in combination with an epigenetic change (i) two or more of (a) an intron; (b) an intron/exon boundary; and/or (c) a splicing region; and/or (ii) approximately one seventh or greater of an intron including an intron/exon boundary and/or a splicing region of the FMR genetic locus including the FMR1 gene. The extent of epigenetic change in two or more of an intron, an intron/exon boundary and/or a splicing region or in one seventh or greater of an intron within the FMR genetic locus may be determined alone or in combination with extent of $(CGG)_n$ expansion and/or any other epigenetic change therein. The determination of epigenetic change may also be conducted in combination with an assay as contemplated by International Patent Application No. PCT/AU2010/000169 filed on 17 Feb. 2010, the contents of which are incorporated herein by reference in their entirety. In an embodiment, the epigenetic modification is a change in extent of methylation which includes hypermethylation and hypomethylation and profile of methylation.

Another aspect of the present disclosure contemplates a method for identifying a pathological condition in a mammalian subject including a human, the method comprising screening for a change relative to a control in the extent of change in methylation or other epigenetic modification within a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

wherein a change in epigenetic modification relative to a control is indicative of the presence or severity of the pathological condition or a propensity to develop same. In an embodiment, the pathological condition is a trinucleotide expansion disorder.

As indicated above, the region within the FMR genetic locus assayed for epigenetic change is selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

Hence, in relation to detecting epigenetic changes in (i) two or more of (a) an intron; (b) an intron/exon boundary; and/or (c) a splicing region; and/or (ii) approximately one seventh or greater of an intron including an intron/exon boundary and/or a splicing region or FREE3 within intron 2, the present disclosure enables the diagnosis monitoring or analyzing of a spectrum of neurodegenerative or neurodevelopmental pathologies such as Fragile X-related conditions including FXS, FXTAS, FXPOI, autism, mental retardation, a modified X-chromosome and cognitive impairment. Certain tri-nucleotide disorders are also included.

A "modified" X-chromosome includes an inactivated X-chromosome or an X-chromosome having a skewed X-inactivation, or inversion, insertion, deletion, duplication or is a hybrid.

The epigenetic profile is determined in the genome of a cell of a subject. Any cell may be tested such as a cell from a post-natal or pre-natal human or embryo. More particularly, the cell is a cultured or uncultured chorionic villi sample (CVS) cell, a lymphoblast cell, a blood cell, a buccal cell, epithelial cells, fibroblast cells, an amniocyte or an EBV transformed lymphoblast cell line.

In a particular embodiment of the present disclosure, the epigenetic modification is methylation of CpG and/or CpNpG sites. Methylation is determined by a range of assays including bisulfite MALDI-TOF methylation assay. In an alternative embodiment, methylation is determined by use of methylation sensitive PCR, methylation specific melting curve analysis (MS-MCA) or high resolution melting (MS-HRM); quantification of methylation by MALDI-TOF MS; methylation specific MLPA; methylated-DNA precipitation and methylation-sensitive restriction enzymes (COMPARE-MS); single molecule (SMRT) sequencing; or methylation sensitive oligonucleotide microarray; or antibodies. Other methods include NEXT generation (GEN) and DEEP sequencing or pyrosequencing. However, any assay of methylation status may be employed. Regardless of the method, either strand of genomic double stranded DNA may be assessed for its epigenetic profile.

Further taught herein is a method for screening for an agent which modulates epigenetic change of (i) two or more of (a) an intron; (b) an intron/exon boundary; and/or (c) a splicing region; and/or (ii) approximately one seventh or greater of an intron including an intron/exon boundary and/or a splicing region within a genetic locus, the method comprising screening for a change relative to a control in the extent of epigenetic modification within the intron 1n the presence or absence of an agent to be tested, wherein an agent is selected if it induces a change in the epigenetic modification.

In an embodiment, the epigenetic modification is associated with a polyglutamine (polyQ) disease such as Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome. The "association" is based on a change in epigenetic profile from that of healthy controls.

In an embodiment, the agent modulates genetic change in the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

In an embodiment, a method is also provided for screening for an agent which modulates epigenetic modification of an FMR genetic locus in a mammalian cell including a human cell, the method comprising screening for a change relative to a healthy control in the extent of epigenetic change in (i) two or more of (a) an intron; (b) an intron/exon boundary; and/or (c) a splicing region; and/or (ii) approximately one seventh or greater of an intron including an intron/exon boundary and/or a splicing region of the FMR genetic locus; wherein the intron, intron/exon boundary and/or splicing region is selected from the list consisting of:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions; and (iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

in the presence or absence of an agent to be tested wherein the agent is selected if it induces a change in extent of epigenetic modification. Such an agent is useful in treating a trinulceotide expansion disorder or other pathological conditions.

A method is also provided for screening for an agent which modulates epigenetic change of an FMR genetic locus in a mammalian cell including a human cell, the method comprising screening for a change relative to a control in the extent of epigenetic modification within a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

in the presence or absence of an agent to be tested wherein the agent is selected if (i) it induces a change in extent of epigenetic modification and/or (ii) causes an improvement in disease phenotype based on the type and degree of epigenetic modification. A change in extent of methylation includes hypermethylation, hypomethylation and a change in the profile of methylation.

As indicated above, in an embodiment, the epigenetic modification is methylation. De-methylation as well as pro-methylation agents are contemplated herein.

Further enabled herein is a method for monitoring the treatment of a disease condition including trinucleotide expansion disorders associated with a change in epigenetic profile from that observed in healthy controls such as Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome, the method comprising screening for a change relative to the control in the extent of epigenetic modification within a genetic locus wherein the epigenetic profile of the genetic locus is associated with the disease or condition, wherein the extent of epigenetic change is indicative of the presence or severity of the pathological condition, wherein the treatment modulates the extent of epigenetic change of (i) two or more of (a) an intron; (b) an intron/exon boundary; and/or (c) a splicing region; and/or (ii) approximately one seventh or greater of an intron including an intron/exon boundary and/or a splicing region within the genetic locus, the method comprising monitoring for a change relative to a control in a pre- and post-treatment sample in the extent of epigenetic modification within the intron, wherein a change in extent of epigenetic modification after or during treatment is indicative of effective treatment.

In an embodiment, the genetic locus is the FMR genetic locus and the disease or condition is FXS or a related condition such as FXTAS, FXPOI, autims, mental retardation, a modified X-chromosome or cognitive impairment.

By "monitoring" in this context includes diagnosis of disease, monitoring progress of the disease before or after treatment, prognosis of the disease development or remission as well as the pharmacoresponsiveness or pharmacosensitivity of a subject or agent.

The present disclosure also teaches the use of an epigenetic profile within (i) two or more of (a) an intron; (b) an intron/exon boundary; and/or (c) a splicing region; and/or (ii) approximately one seventh or greater of an intron including an intron/exon boundary and/or a splicing region of a genetic locus in a cell in the manufacture of an assay to identify an epigenetic profile of gene associated with a pathological condition. In an embodiment, the genetic locus is the FMR genetic locus and epigenetic change is monitored within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

An embodiment herein is directed to the use of an epigenetic profile within the FMR genetic locus in a mammalian cell including a human cell, the epigenetic profile including methylation of CpG and/or CpNpG sites located in a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

in the manufacture of an assay to identify an epigenetic profile of an FMR locus-associated pathological condition.

The assay taught herein may also be used alone or in combination with assays to detect extent of a nucleotide expansion such as a $(CGG)_n$ expansion, such as using PCR and Southern blot assays. This is useful in determining homozygosity, heterozygosity and mosaicism of a disease or condition. The assay of the present disclosure is also useful in population studies such as epidemiological studies as well as studies based on ethnic populations. Accordingly, another aspect enabled herein provides a method of identifying epigenetic profile in populations of subjects indicative of a pathological condition associated with epigenetic modifications or changes in an intron, intron/exon boundary and/or splicing region, the method comprising screening for a change, relative to a control in a statistically significant number of subjects, in the extent of epigenetic change within (i) two or more of (a) an intron; (b) an intron/exon boundary; and/or (c) a splicing region; and/or (ii) approximately one seventh or greater of an intron including an intron/exon boundary and/or a splicing region of a genetic locus, the epigenetic change including extent of methylation of CpG and/or CpNpG sites located within the intron, intron/exon boundary and/or splicing region wherein a change in extent of epigenetic modification is indicative of the presence or severity of the pathological condition or a propensity to develop same.

In an embodiment, the epigenetic modification is determined in the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

Contemplated herein is a method of identifying a methylation or other epigenetic profile in a population of subjects indicative of a pathological condition associated with the FMR locus, the method comprising screening for a change, relative to a control, in a statistically significant number of subjects in the extent of epigenetic modification including extent of change in methylation of CpG and/or CpNpG sites within a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

wherein a change in extent of epigenetic modification is indicative of the presence of the pathological condition or a propensity to develop same in the population.

In accordance with this method the assay may comprise the further step of determining the extent of a nucleotide expansion such as a (CGG)n expansion such as by PCR and/or Southern blot analysis. The regions investigated for epigenetic change within the FMR genetic locus include:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

Aspects herein extend to the use of the epigenetic profile of an intron within a genetic locus to determine the status, prognosis or disease development or recovery and/or treatment options including responsiveness of the subject to pharmacological agents and/or behavioral intervention strategies.

Computer programs to monitor changes in epigenetic modification or profile over time that may assist in making decisions regarding treatment options including responsiveness of the subject to pharmacological agents and/or behavioral intervention strategies, are also enabled herein.

Accordingly, another aspect provides a method of allowing a user to determine the status, prognosis and/or treatment response of a subject with respect to an FMR locus-associated pathology, the method including:

(a) receiving data in the form of extent of methylation or other epigenetic modification at a site within (i) two or more of (a) an intron; (b) an intron/exon boundary; and/or (c) a splicing region; and/or (ii) approximately one seventh or greater of an intron including an intron/exon boundary and/or a splicing region of a genetic locus associated with the pathology, wherein the extent of methylation or other epigenetic modification provides a correlation to the presence, state, classification or progression of the pathology;

(b) transferring the data from the user via a communications network;

(c) processing the subject data via multivariate or univariate analysis to provide a disease value;

(d) determining the status of the subject in accordance with the results of the disease value in comparison with predetermined values; and (e) transferring an indication of the status of the subject to the user via the communications network.

In an embodiment, the genetic locus is the FMR genetic locus. The epigenetic profile is determined within the FMR genetic locus from a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

In an embodiment, a method is provided of allowing a user to determine the status, prognosis and/or treatment response of a subject with respect to an FMR locus-associated pathology, the method including:

(a) receiving data in the form of extent of methylation or other epigenetic modification at a site selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

wherein the extent of methylation or other epigenetic modification provides a correlation to the presence, state, classification or progression of the pathology;

(b) transferring the data from the user via a communications network;

(c) processing the subject data via multivariate or univariate analysis to provide a disease index value;

(d) determining the status of the subject in accordance with the results of the disease index value in comparison with predetermined values; and (e) transferring an indication of the status of the subject to the user via the communications network.

A further embodiment enabled herein is a kit comprising primers which amplify regions of the FMR genetic locus, comprising CpG and/or CpNpG sites located within a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

in the manufacture of a diagnostic kit or device to detect epigenetic modification of the FMR locus-associated with a pathological condition.

In an embodiment, the epigenetic modification relates to extent of, or change in, methylation at CpG and/or CpNpG sits within the selected regions of the FMR genetic locus, defined as FREE3, intron 2 and an intron, intron/exon boundary and/or splicing region downstream of intron 2 of the FMR gene. In an embodiment, the epigenetic modification occurs in the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

In an embodiment, the primers useful in practicing the subject assay are selected from the list consisting of SEQ ID NOs:6 through 11. Those sequences include tag sequences. The present disclosure extends to the primer only portions of SEQ ID NOs:6 through 11.

TABLE 1

Summary of sequence identifiers

| SEQUENCE ID NO: | DESCRIPTION |
|---|---|
| 1 | Nucleotide sequence of FREE3 within the FMR1 gene |
| 2 | Nucleotide sequence of intron 2 of the FMR1 gene |
| 3 | Nucleotide sequence of intron 1 of FMR1 gene |
| 4 | Nucleotide sequence of FREE2 (B) |
| 5 | Nucleotide sequence of FREE2 (C) |
| 6 | Forward primer and tag sequence for FREE2 (B) |
| 7 | Reverse primer and tag sequecne for FREE2 (B) |
| 8 | FREE 2 (C) forward primer and tag |
| 9 | FREE2 (C) reverse primer and tag |
| 10 | FREE3 forward primer and tag |

TABLE 1-continued

Summary of sequence identifiers

| SEQUENCE ID NO: | DESCRIPTION |
|---|---|
| 11 | FREE3 reverse primer and tag |
| 12 | Nucleotide sequecne of regulatory motif GATA-1 |
| 13 | Nucleotide sequence of regulatory motif HSF2 |
| 14 | Nucleotide sequence of regulatory motif C/EBP |
| 15 | Nucleotide sequence of regulatory motif CdxA |
| 16 | Nucleotide sequence of regulatory motif AML-1a |
| 17 | Nucleotide sequence of regulatory motif AML-1a |
| 18 | Nucleotide sequence of regulatory motif CdxA |
| 19 | Nucleotide sequence of regulatory motif CdxA |
| 20 | Nucleotide sequence of regulatory motif CdxA |
| 21 | Nucleotide sequence of regulatory motif HFH-1/HFH-2 |
| 22 | Nucleotide sequence of regulatory motif Cdx2 |
| 23 | Nucleotide sequence of regulatory motif SRY |
| 24 | Nucleotide sequence of regulatory motif SRY |
| 25 | Nucleotide sequence of regulatory motif SRY |
| 26 | Nucleotide sequence of regulatory motif S8 |
| 27 | Nucleotide sequence of regulatory motif SRY |
| 28 | Nucleotide sequence of regulatory motif CdxA |
| 29 | Nucleotide sequence of regulatory motif Oct-1 |
| 30 | Nucleotide sequence of intron1 downstream of FREE2 (C) |
| 31 | Nucleotide sequence of exon2 upstream of FREE3 |
| 32 | Nucleotide sequence of CGG amplification primer (r) |
| 33 | Nucleotide sequence of CGG amplification primer (f) |
| 34 | ASFMR1 (−1) forward primer |
| 35 | ASFMR1 (−1) reverse primer |
| 36 | ASFMR1 (−1) probe |
| 37 | ASFMR1 (−2) forward primer |
| 38 | ASFMR1 (−2) reverse primer |
| 39 | ASFMR1 (−2) probe |
| 40 | ASFMR1 (−3) forward primer |
| 41 | ASFMR1 (−3) reverse primer |
| 42 | ASFMR1 (−3) probe |
| 43 | Forward primer FREE2 (D) |
| 44 | Reverse primer FREE2 (D) |
| 45 | Forward primer FREE2 (E) |
| 46 | Reverse primer FREE2 (E) |
| 47 | Genomic target sequence FREE3 |
| 48 | Genomic target sequence FREE2 (D) |
| 49 | Genomic target sequence FREE2 (E) |
| 50 | Forward primer FREE3 |
| 51 | Forward primer FREE3 |
| 52 | Tag forward primer FREE2 (D) |
| 53 | Tag reverse primer FREE2 (D) |
| 54 | Tag forward primer FREE2 (E) |
| 55 | Tag reverse primer FREE2 (E) |
| 56 | Tag forward primer FREE3 |
| 57 | Tag reverse primer FREE3 |

A list of abbreviations used herein is provided in Table 2.

TABLE 2

Abbreviations

| ABBREVIATION | DESCRIPTION |
|---|---|
| Ab | Antibody |
| ASFMR1 | Antisense Fragile X mental retardation 1 gene |
| $(CGG)_n$ | CGG repeat element located within 5' untranslated region of the FMR1 gene |
| CpG | Cytosine and guanine separated by a phosphate (C-phosphate-G), which links the two nucleosides together in DNA |
| CpNpG | Cytosine and guanine separated by a nucleotide (N) where N is any nucleotide but guanine. The cytosine and N nucleotide are phosphorylated. |
| CVS | Cultured or uncultured Chorionic Villi Sample |
| DM | Mytotonic dystrophy |
| DNA | Deoxyribonuceic acid |
| DRPLA | dentatorubropallid oluysiantrophy |
| FIQ | Full scale IQ |
| FM | Full Mutation |
| FMR | Fragile X mental retardation genetic locus comprising of FMR1 and FMR4 genes |

TABLE 2-continued

Abbreviations

| ABBREVIATION | DESCRIPTION |
| --- | --- |
| FMR1 | Fragile X mental retardation 1 gene |
| FMRP | Fragile X mental retardation protein |
| FRA12A | Fragile type, folic acid type, rare 12 |
| FRAXE | Fragile X E mental retardation |
| FRDA | Friedrich's ataxia |
| FREE | Fragile X related Epigenetic Element (e.g. FREE2 and FREE3) |
| FREE2 (D)/(E) boundary | Boundary of FREE2 (D) and FREE2 (E) |
| FXPOI | Fragile X-associated primary ovarian insufficiency |
| FXS | Fragile X Syndrome |
| FXTAS | Fragile X-associated Tremor Ataxia Syndrome |
| GZ | Gray Zone |
| HD | Hungtington's disease |
| HRM | Heat Resolution Melt |
| MR | Mental retardation |
| ORF | Open Reading Frame |
| PCR | Polymerase Chain Reaction |
| PM | Premutation |
| POF | Premature Ovarian Failure |
| PolyQ | Polyglutamine |
| SBMA | spinobullar muscular atrophy (Kennedy disease) |
| SCA1 | spinocerebellar ataxia Type 1 |
| SCA17 | spinocerebellar ataxia Type 17 |
| SCA2 | spinocerebellar ataxia Type 2 |
| SCA3 | spinocerebellar ataxia Type 3 |
| SCA6 | spinocerebellar ataxia Type 6 |
| SCA7 | spinocerebellar ataxia Type 7 |
| SCA8 | spinocerebellar ataxia Type 8 |

BRIEF DESCRIPTION OF THE FIGURES

Some figures contain color representations or entities. Color photographs are available from the Patentee upon request or from an appropriate Patent Office. A fee may be imposed if obtained from a Patent Office.

DETAILED DESCRIPTION

Figure 1:
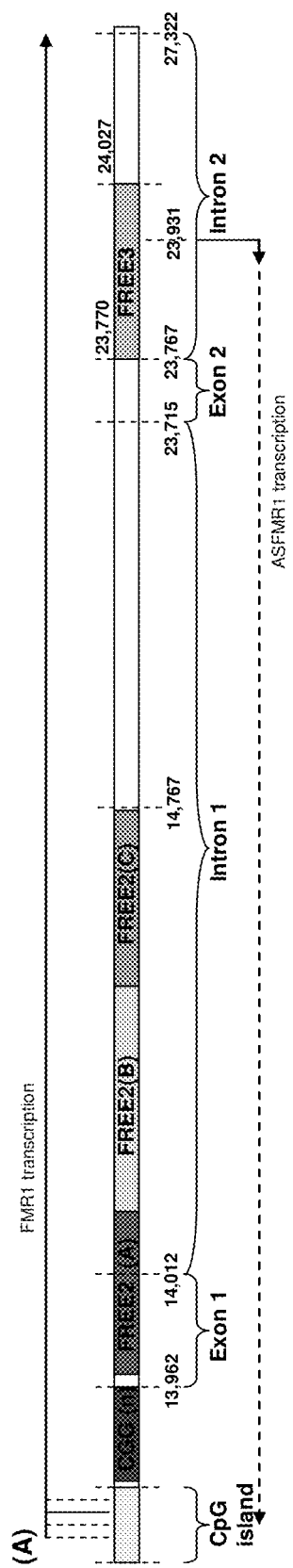
FIG. 1. (A) is a representation of the intron and exon regions 5' of the FMR1 CGG expansion (sequence numbering from GenBank L29074 L38501). (A) is a diagrammatic representation of the organization of the FMR genetic locus in relation to FMR1 and ASFMR1 transcription start sites, FMR1 promoter, the Fragile X-related epigenetic elements (FREE), FMR1 gene has 17 exons, and encodes FMRP. A CGG repeat is located within the 5' (UTR) of the FMR1 gene. ASFMR1 spans the CGG expansion in the antisense direction and is also regulated by another promoter located in the exon 2 of FMR1. The FREE2 located downstream of the CGG expansion. The FREE3 region is located within intron 2 of FMR1 downstream of the second ASFMR1 promoter. (B) Primers utilized for MALDI-TOF methylation analysis targeted 4 regions at the Xq27.3 locus designated as FREE2(A) [described as amplicon 5 in Godler et al., *Hum Mol Genet* 10(8):1618-1632. [Epub 2010]; Godler et al., *J. Mol Diagn.* 2011 [Epub ahead of print] PMID:21723415; HMG); FREE2(B); FREE2(C) and FREE3 (color coded). Individual CPG sites within each region are numbered accordingly. Prominent transcription factor binding sites and methylation sensitive restriction enzyme recognition sites are indicated in capital font, and are listed/identified in Table 1. << Indicates ASFMR1 transcription start site.
Figure 1:
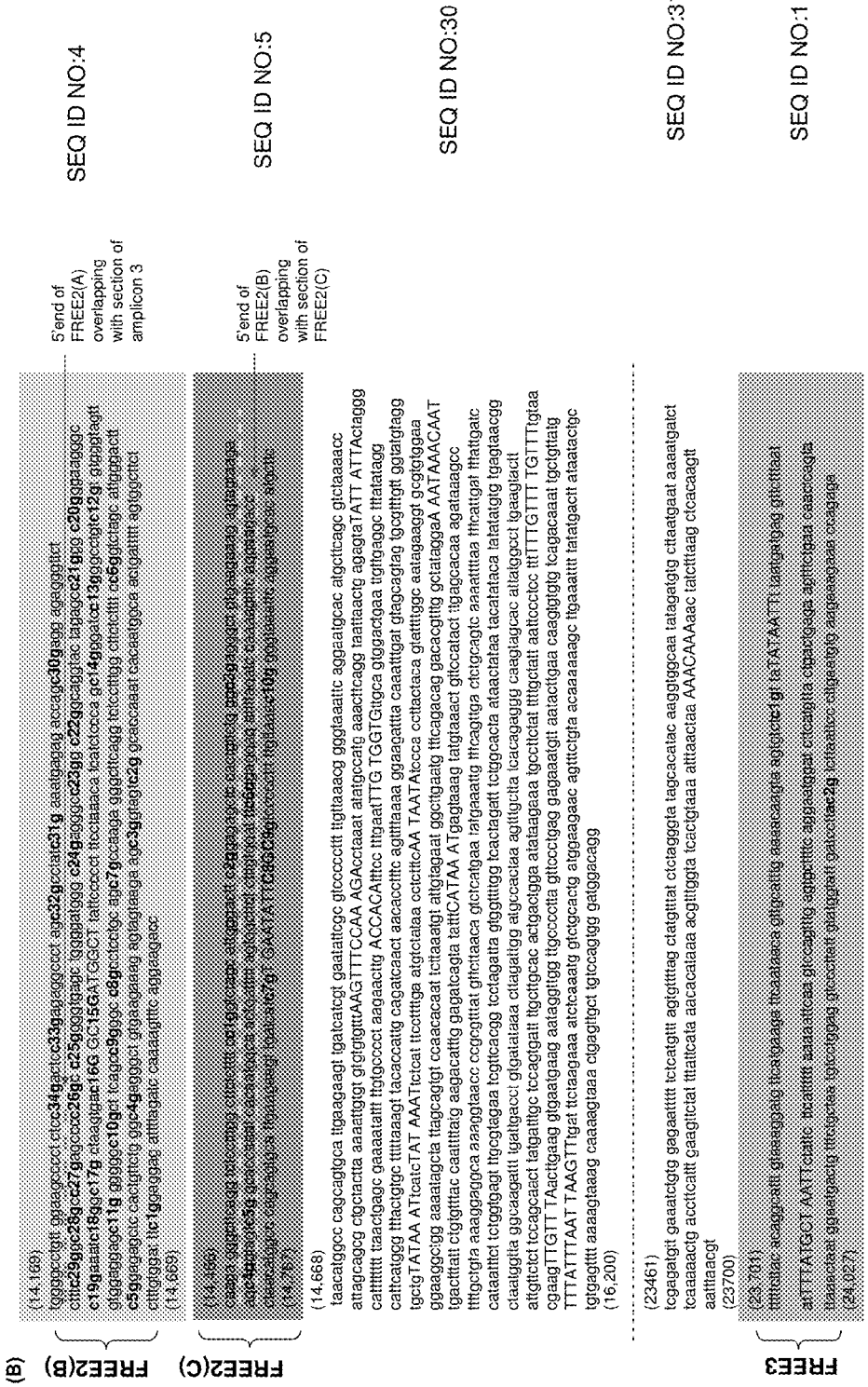

Taught herein is to a method for identifying an epigenetic profile of an intron, intron/exon boundary and/or splicing region within a genetic locus associated with or indicative, instructive or informative of a pathological condition. The epigenetic modification occurs in:

(i) two or more of (a) an intron; (b) an intron/exon boundary; and/or (c) a splicing region; and/or (ii) approximately one seventh or greater of an intron including an intron/exon boundary and/or a splicing region; within a genetic locus. In an embodiment, the pathological condition is a trinucleotide expansion disorder such as in association with a change in epigenetic profile from that of a healthy control subject.

By "epigenetic profile" includes epigenetic modifications such as methylation including hypermethylation and hypomethylation, RNA/DNA interactions, expression profiles of non-coding RNA, histone modification, changes in acetylation, obiquitylation, phosphorylation and sumoylation, as well as chromatin altered transcription factor levels and the like leading to activation or deactivation of genetic locus expression. Particularly, the extent of methylation, RNA/DNA interaction and non-coding RNA expression are determined as well as any changes therein. In an aspect, the epigenetic modification is an elevation in methylation, a decrease in methylation or an alteration in distribution of methylation sites. The epigenetic profile may be determined on either strand of genomic double stranded DNA or an amplified fragment thereof. Hence, primers may be generated to amplify either strand of a genomic DNA target.

The pathological condition may be a neurological or non-neurological condition. Insofar as the condition is neurological, it may be described as a neuropathological condition or a pathoneurological condition which encompasses neurodegenerative and neurodevelopmental disorders. Non-neurological pathologies are also contemplated herein as well as any nucleotide expansion disease or condition. Reference to a pathological conditions includes a trinucleotide expansion disorder. Reference to a "control" means relative to a healthy subject which means a subject with a normal size of expansion repeats and/or who is phenotypically normal meaning that the subject does not have symptoms of, for example, a trinucleotide expansion disorder and/or is the epigenetic profile observed in healthy control subjects.

In an embodiment, the pathological disease or condition including trinucleotides expansion disorders associated with a change in the epigenetic profile from that observed in healthy controls associated with the intronic epigenetic change is Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome. The present disclosure also identifies nucleotide expansion diseases and conditions. In an embodiment, the genetic locus is the FMR genetic locus and the pathology is FXS or related condition such as FXTAS, FXPOI, autism, mental retardation, a modified X-chromosome or cognitive impairment.

A method is enabled for identifying an epigenetic profile in a genome of a cell indicative of a pathological condition selected from Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome, the method comprising screening for a change relative to the control in the extent of epigenetic modification in a genetic locus within (i) two or more of (a) an intron; (b) an intron/exon boundary; and/or (c) a splicing region; and/or (ii) approximately one seventh or greater of an intron including an intron/exon boundary and/or a splicing region of a genetic locus associated with the pathological condition wherein the extent of epigenetic change is indicative of the presence or severity of the pathological condition or a propensity to develop same. In an embodiment, the genetic locus is the FMR locus and the region assayed for epigenetic change is selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

In an embodiment, a method is provided for identifying an epigenetic profile in a genome of a cell indicative of FXS or related condition the method comprising screening for a change relative to the control in the extent of epigenetic modification in the FMR genetic locus within (i) two or more of (a) an intron; (b) an intron/exon boundary; and/or (c) a splicing region; and/or (ii) approximately one seventh or greater of an intron including an intron/exon boundary and/or a splicing region of a genetic locus associated with the pathological condition wherein the extent of epigenetic change is indicative of the presence or severity of the pathological condition or a propensity to develop same. A related condition includes FXTAS, FXPOI, autism, mental retardation, a modified X-chromosome and cognitive impairment.

In relation to this aspect, an "intron", "intron/exon boundary" and "splicing region", are regarded as an intron, intron/exon boundary and splicing region within a genetic locus or a gene within a genome. The intron, intron/exon boundary and splicing region may also encode a regulatory RNA species. Either strand of a double stranded genomic DNA or an amplified fragment or region thereof may be assayed for its epigenetic profile.

Figure 4:
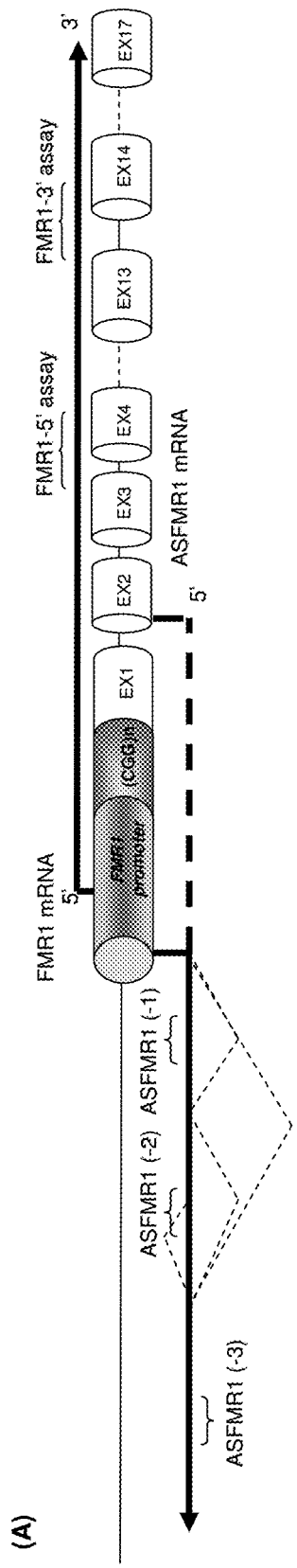
FIG. 4. (A) is a diagrammatic representation of the intron and exon regions at the Xq27.3 locus (sequence numbering from GenBank L29074 L38501), locations of FMR1 and ASFMR1 transcription start sites and alternative splicing events. The locations of target sequences for FMR1 and ASFMR1 real-time PCR assays used are also indicated: ASFMR1 (−1) real-time assay: detects unspliced and splice variant C (positioned −282 to −343 from FMR1 transcription start site), ASFMR1 (−2) real-time assay: detects unspliced only (positioned −588 to −663 from FMR1 transcription start site), ASFMR1 real-time assay: detects all (positioned −1299 to −1360 from FMR1 transcription start site). (B) is a graphical representation of standard curve and amplification real-time PCR plots showing that in the FXS cell lines with fully methylated FMR1 promoter and silenced FMR1 and FMRP, ASFMR1 is expressed. RNA was extracted from 3 FXS cell lines whose methylation profiles are presented in FIG. 2; Sample 849 was taken from the male 490 CGG repeat line; Sample 862 was taken from the male 530 CGG repeat line; Sample 865 was taken from the female 563 and 47 CGG repeat line. Each RNA sample was split in two, with one half subjected to RNase A treatment prior to ASFMR1 (−3) relative standard curve analysis. The ASFMR1 (−3) real-time PCR analysis was performed in quadruplicate reactions. The difference in Ct values between RNase A treated and untreated samples represents the level of ASFMR1 expression. (C) and (D) are graphical representations of standard curve and amplification real-time PCR plots indicating that in the FXS cell lines, ASFMR1RNA forms RNA:DNA complexes. FXS RNA samples were treated with TURBO DNase (C) and RQ1 DNase (D) respectively. These DNase treatments caused complete loss of real-time-PCR signal for the ASFMR1(−3) assay. Because DNase can only degrade RNA molecules if they form complexes with DNA, loss of ASFMR1 after DNase treatment suggests that ASFMR1RNA forms RNA:DNA complexes in FxS samples with fully methylated FMR1 promoter and silenced FMR1 expression.
Figure 4:
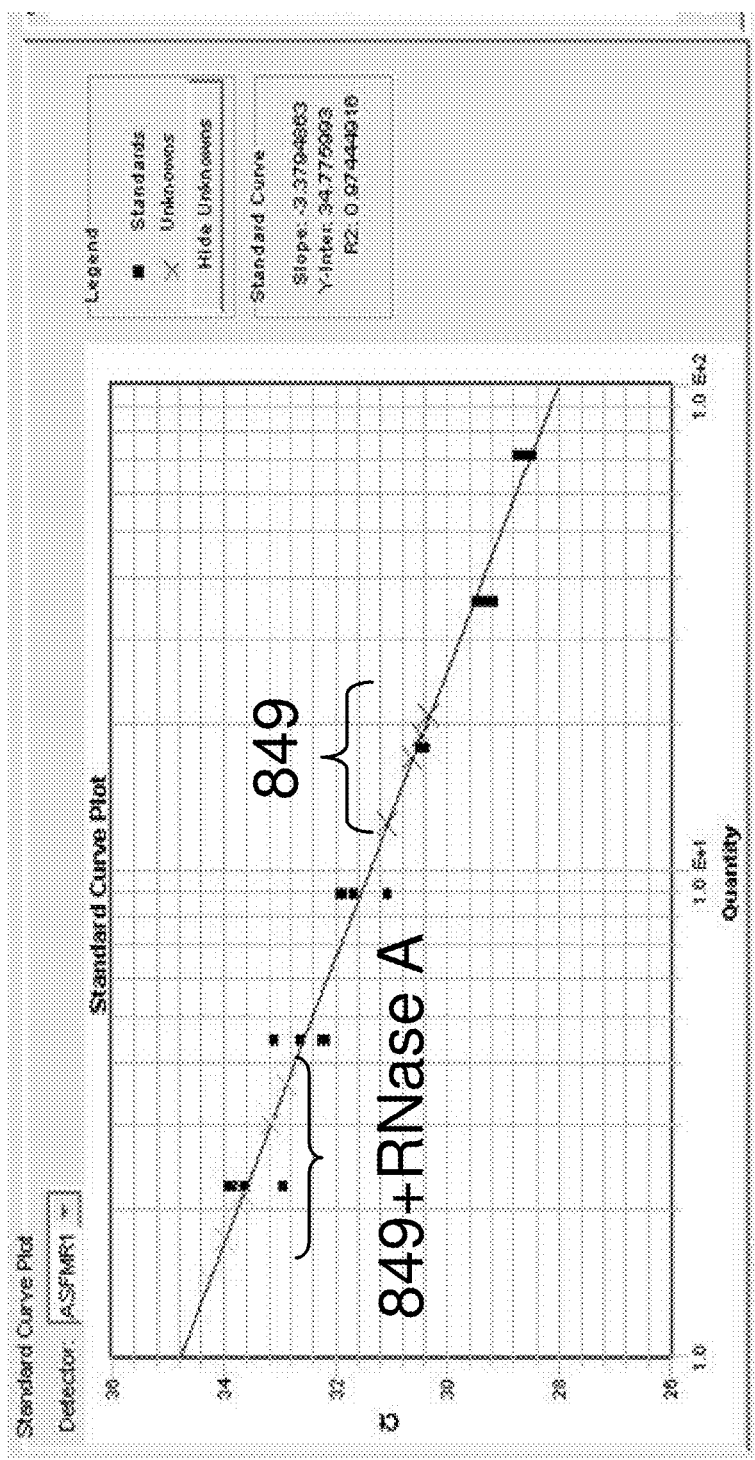
Figure 4:
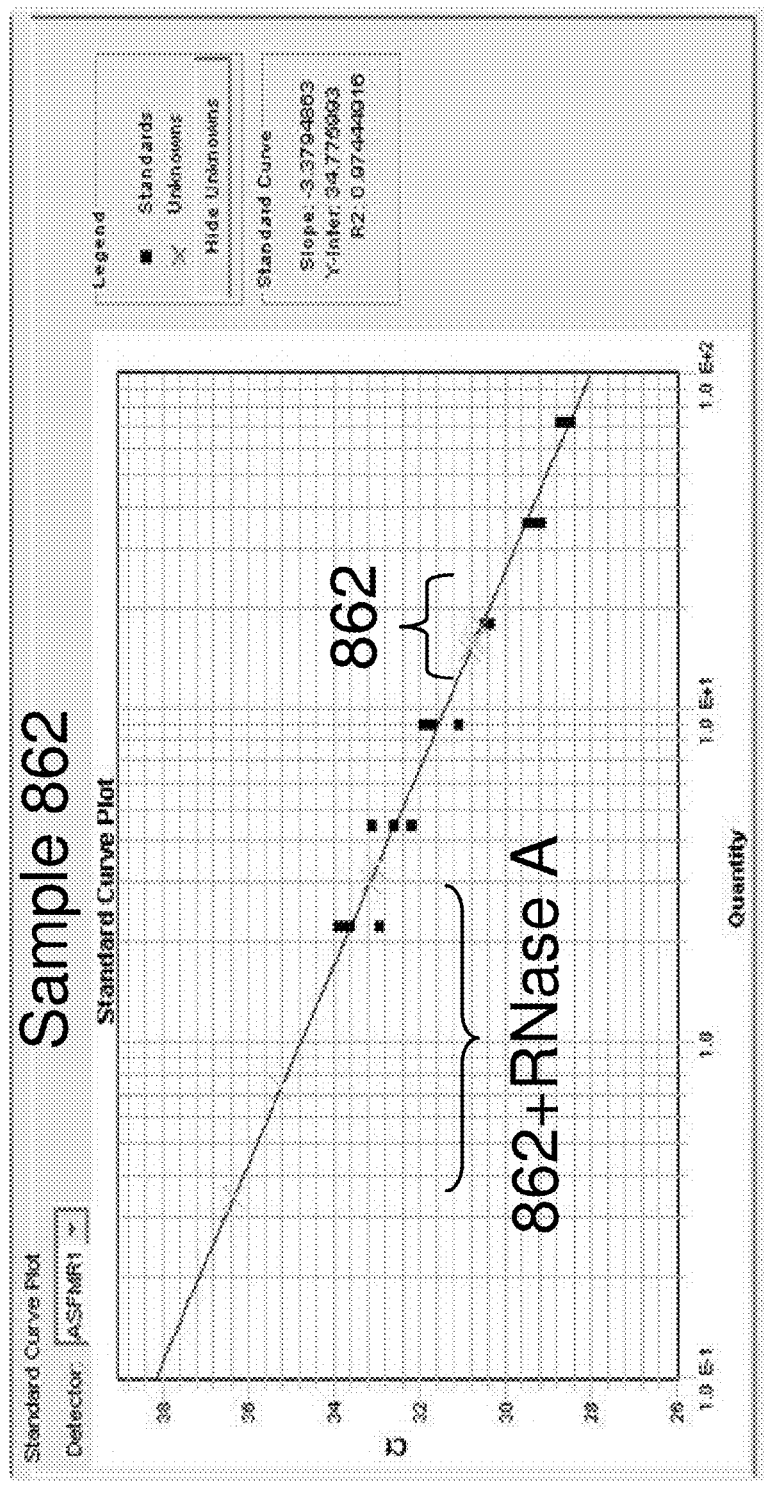
Figure 4:
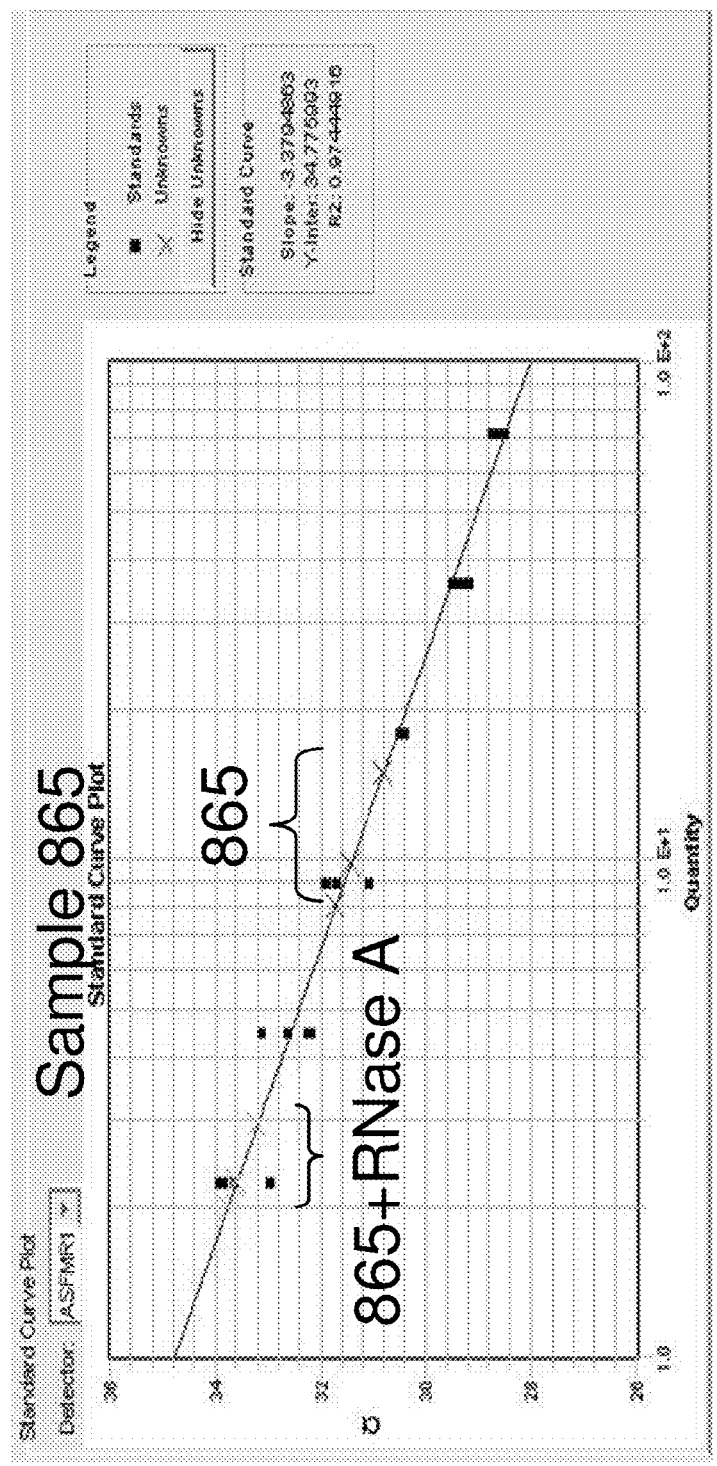
Figure 4:
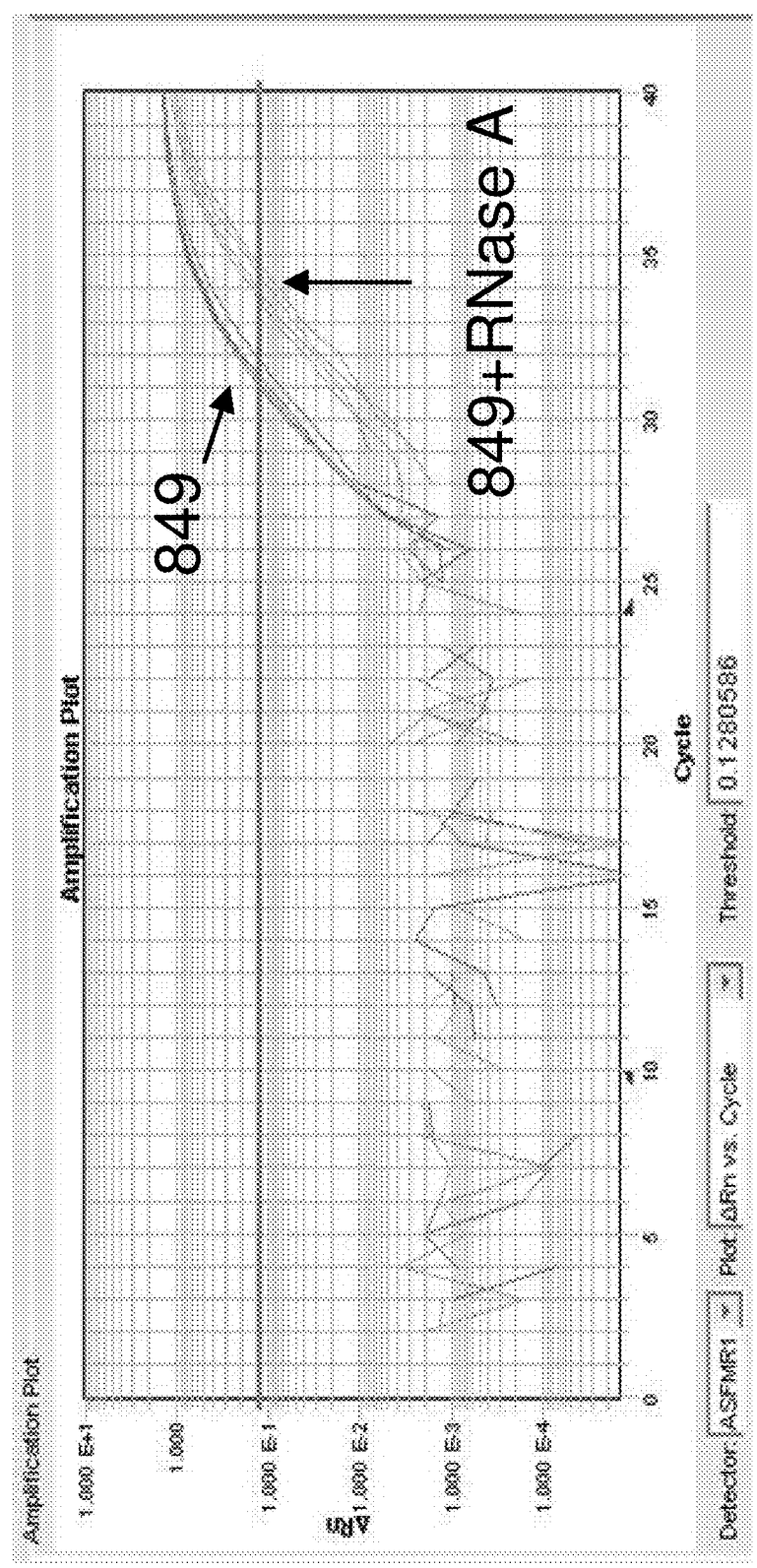
Figure 4:
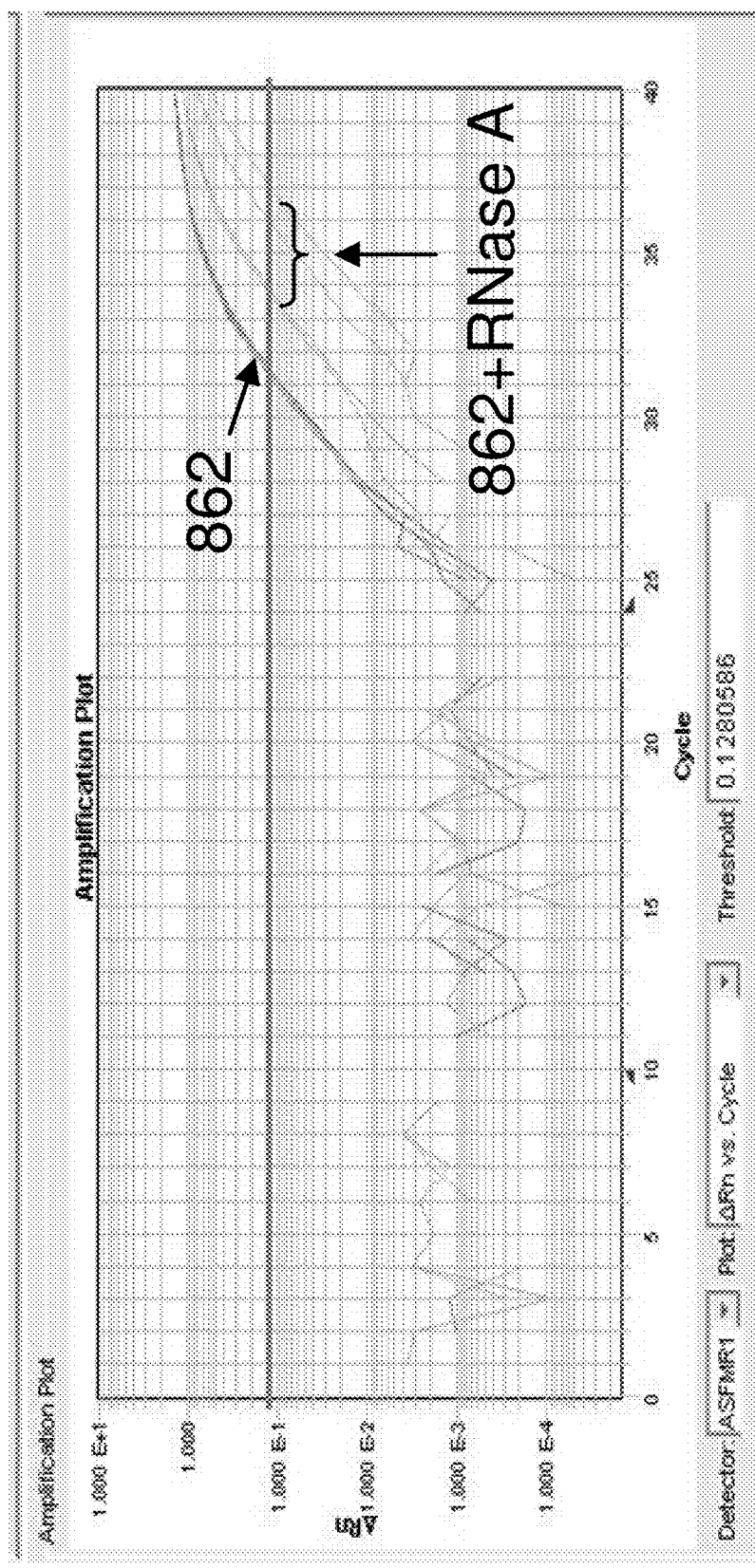
Figure 4:
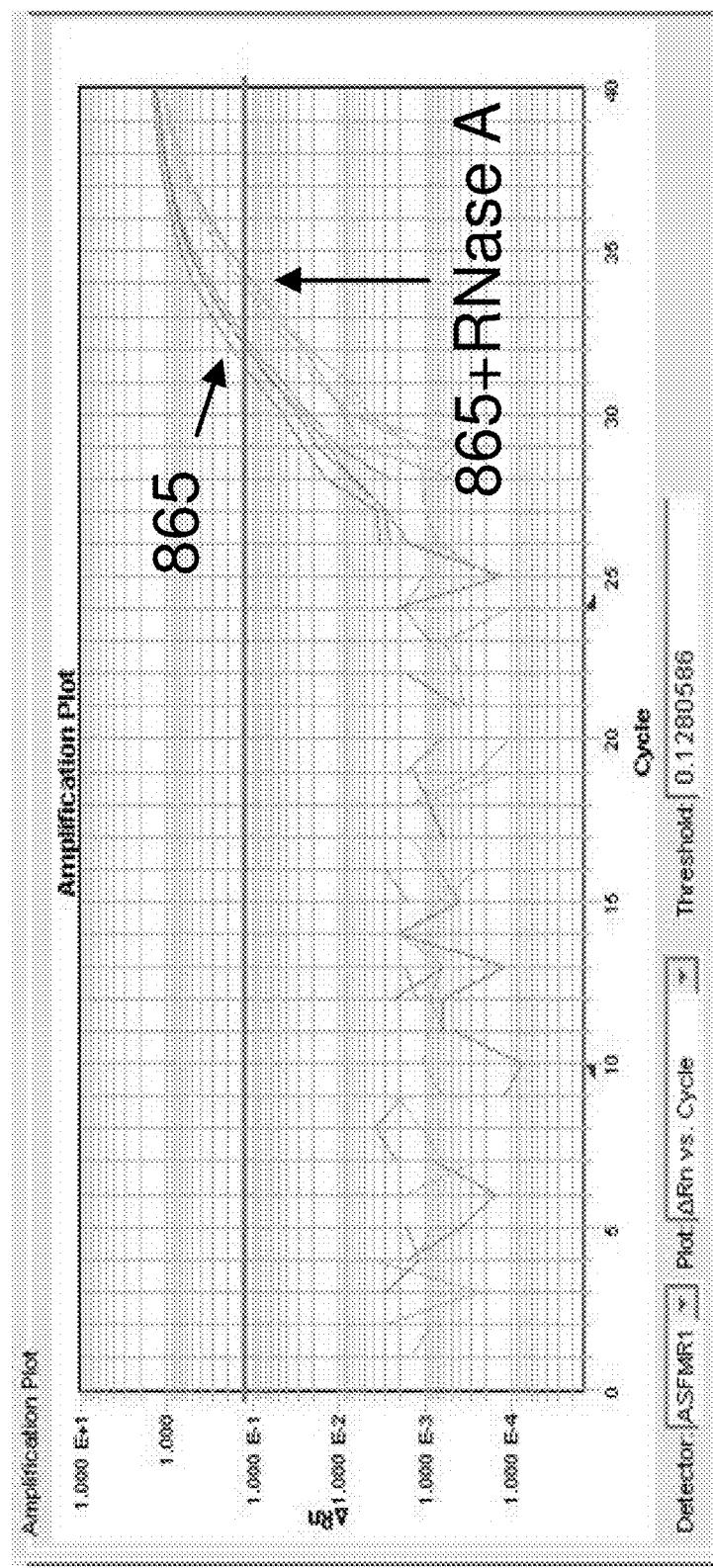
Figure 4:
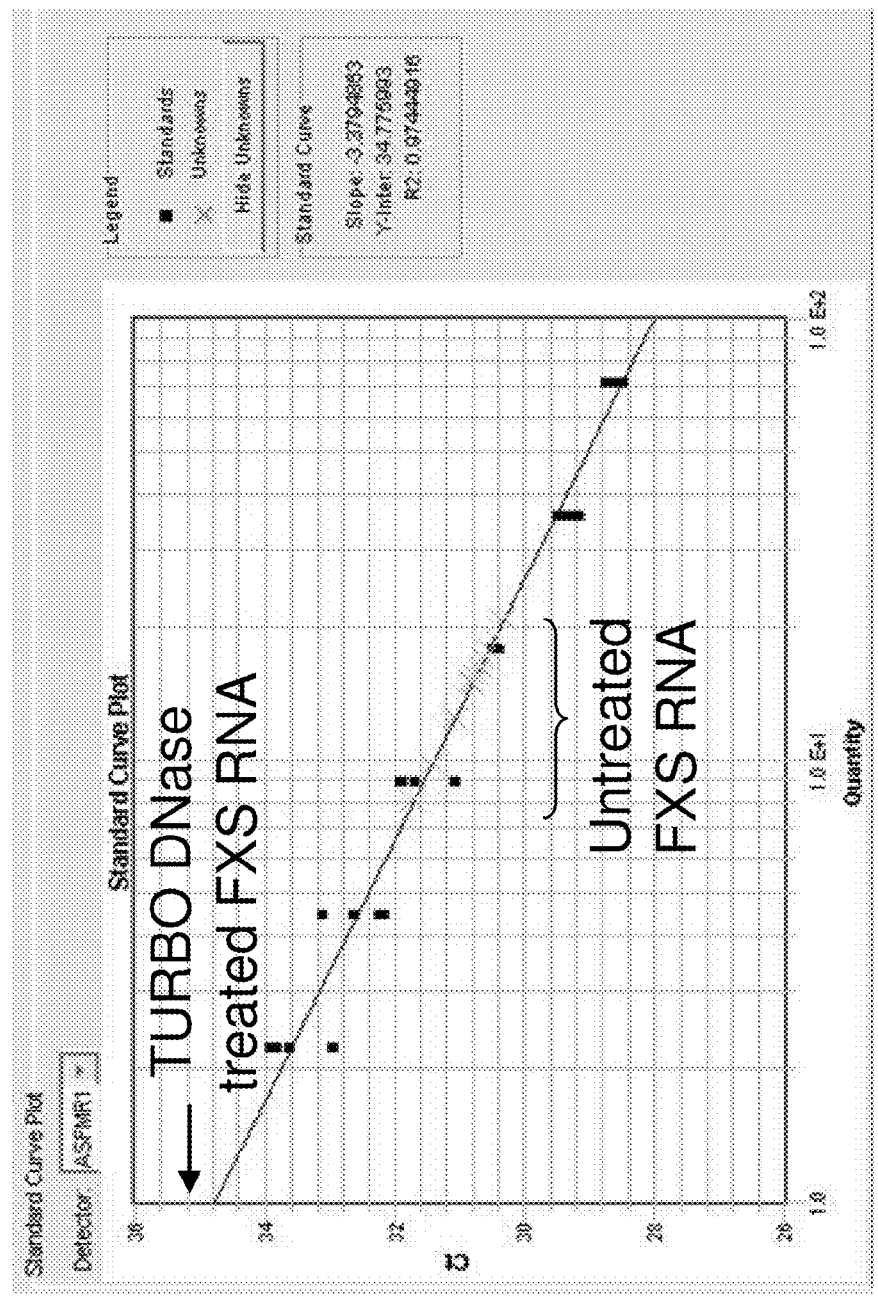
Figure 4:
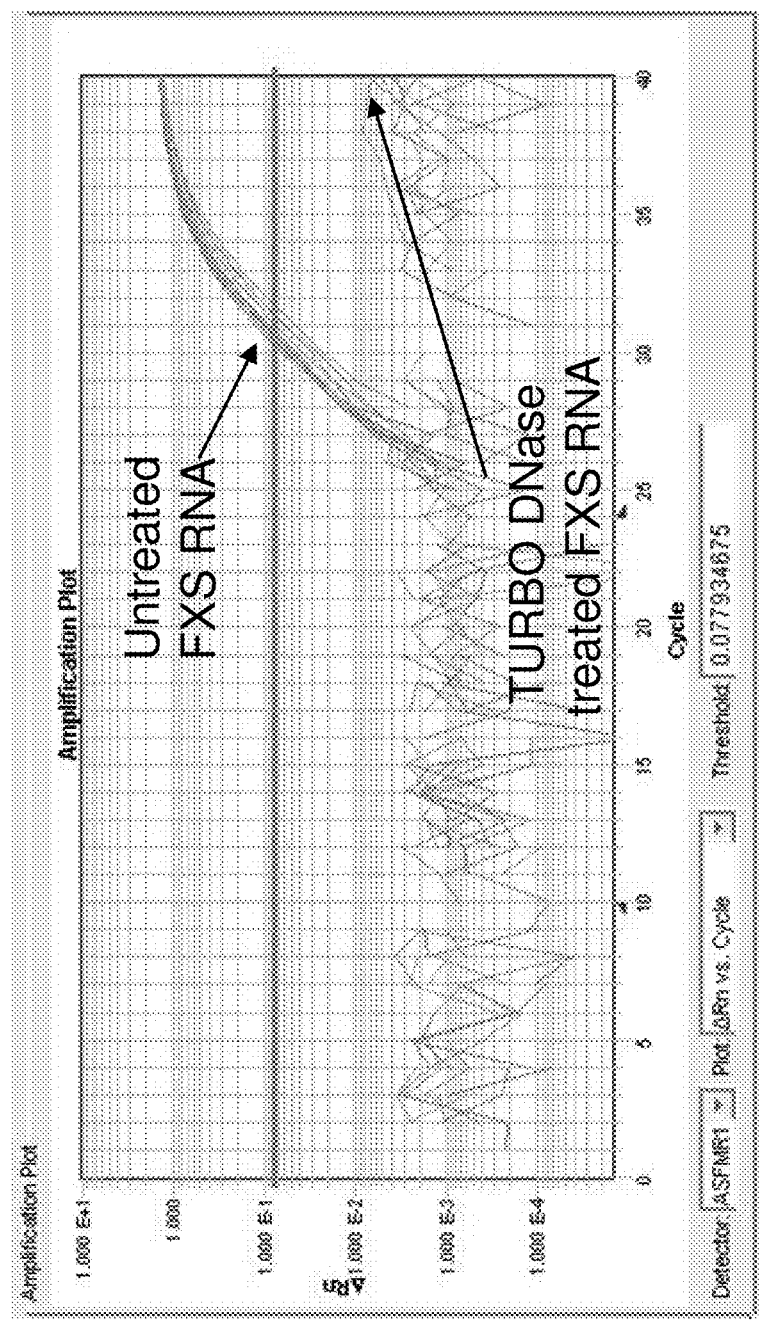
Figure 4:
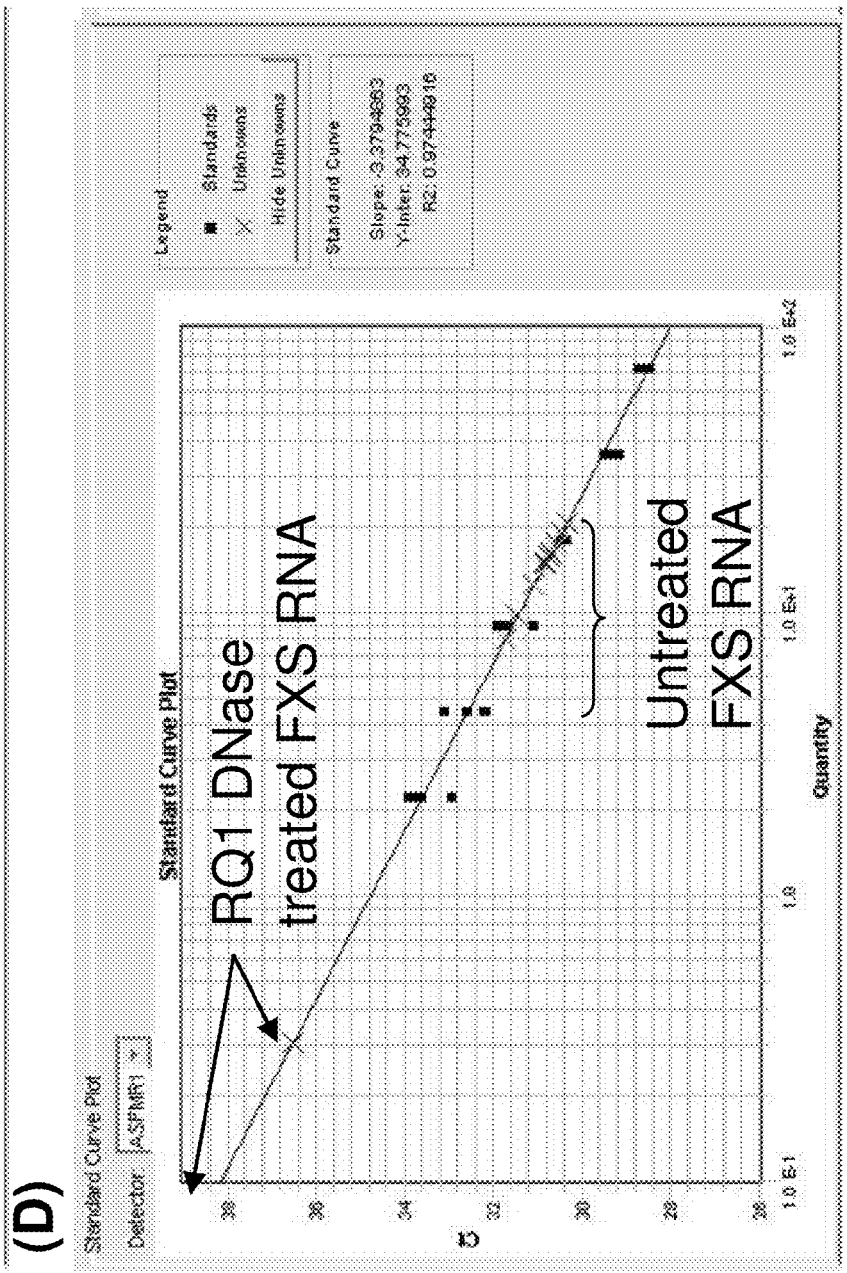
Figure 4:
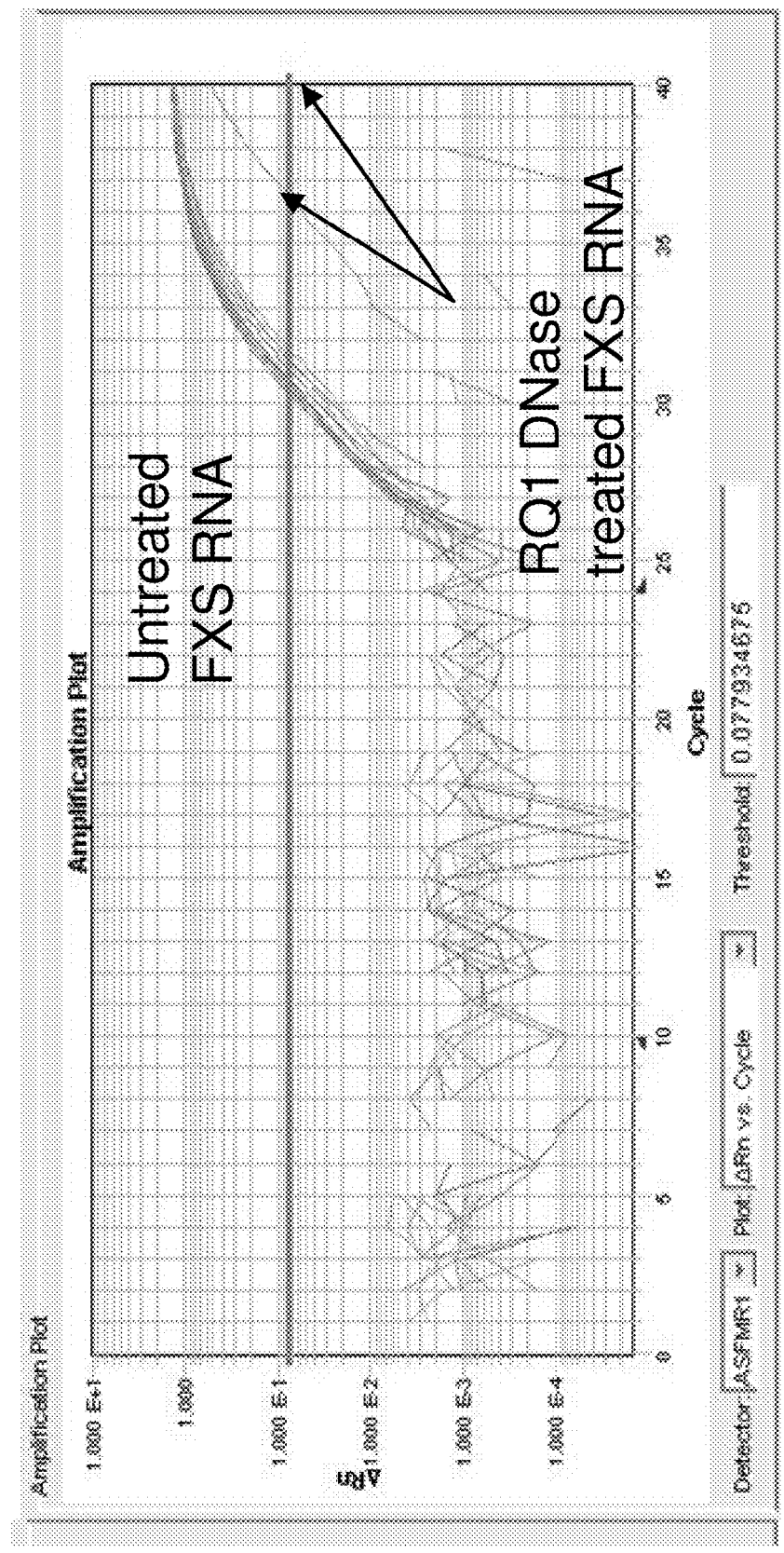
Figure 6:
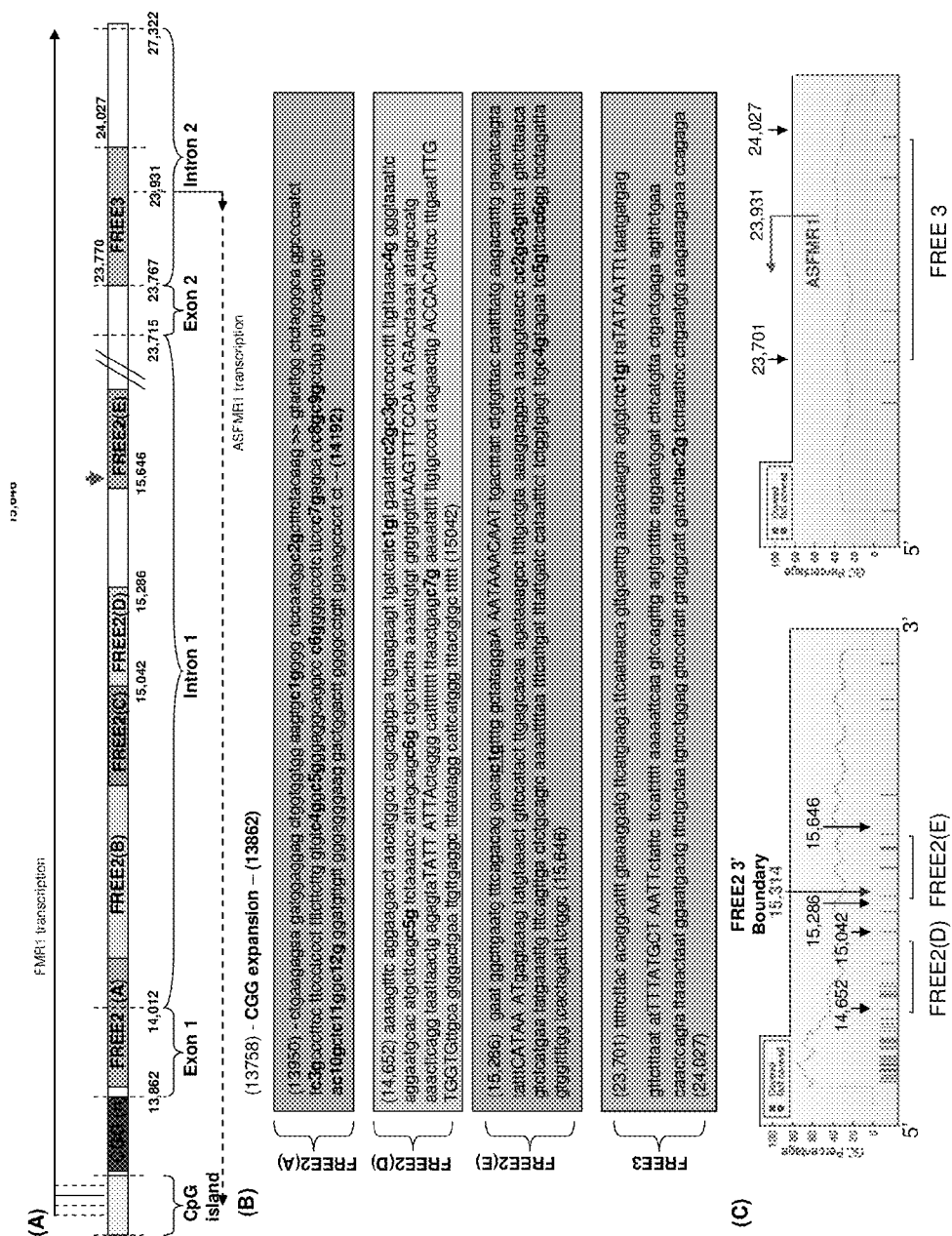
FIG. 6. (A) is a representation of the intron and exon regions 5' of the FMR1 CGG expansion (sequence numbering from GenBank L29074 L38501) in relation to FMR1 and ASFMR1 transcription start sites, FMR1 promoter, the Fragile X-related epigenetic elements 2 and 3 (FREE). A CGG repeat is located within the 5' (UTR) of the FMR1 gene. ASFMR1 spans the CGG expansion in the antisense direction and is also regulated by another promoter located in the exon 2 of FMR1. The FREE2 located downstream of the CGG expansion. The FREE3 region is located within intron 2 of FMR1 and spans the potential second ASFMR1 promoter of transcription in the antisense direction. (B) Primers utilized for MALDI-TOF methylation analysis targeted 5 regions at the Xq27.3 locus designated as FREE2(A) (described as amplicon 5 in Godler et al., *Hum Mol Genet*, 2010; [Epub ahead of print] doi:10.1093/hmg/ddq 1037); FREE2(D); FREE2(E), and FREE3 (color coded). Individual CPG sites within each region are numbered accordingly. Prominent transcription factor binding sites and methylation sensitive restriction enzyme recognition sites are indicated in capital font, and are listed/identified in Tables 3 and 4. << Indicates ASFMR1 transcription start site. The red arrow indicates the FREE2 3' Boundary located at CpG1 of FREE2(E) which is underlined in the sequence. (C) is a representation of the CG dinucleotide density in the regions proximal to the FREE2 3' Boundary. The CpG sites that have been analysed for methylation status are represented in Blue on the X axis, while sites not covered by our assays are represented in red. The coordinates of the FREE2(D) and FREE2(E) assays on the GenBank L29074 L38501 are also indicated.

In an embodiment, the pathological condition is associated with an epigenetic profile of the FMR genetic locus. For the purposes of the present disclosure, the "FMR genetic locus" includes the FMR1, FMR4 and ASFMR1 genes as well as promoter and regulatory regions and introns and exons and intron/exon boundaries. In particular, the FMR genetic locus comprises a promoter region, a $(CGG)_n$ region proximal to the promoter and exonic and intronic regions of the FMR1, FMR4 and ASFMR1 genes as depicted in FIGS. 1A and 4A and 6A. The promoter is generally referred to as the "FMR1 promoter" or "ASFMR1 promoter" for the promoter with an initiation site in FREE3 of intron 2 (see FIG. 6). The FMR locus includes introns, intron/exon boundaries and splicing regions wherein it is proposed herein that epigenetic changes occur within (i) two or more of (a) an intron; (b) an intron/exon boundary; and/or (c) a splicing regions; and/or (ii) approximately one seventh or greater of an intron including an intron/exon boundary and/or a splicing region of the FMR genetic locus including the FMR1 gene or a part thereof such as FREE3 or FREE2 region alone or in combination with the FREE1 region (D) or FREE2 (E) which are indicative or diagnostic of a pathological condition or its severity involving the FMR1, FMR4 and/or ASFMR1 genes. FREE3, FREE2 (D) and FREE2 (E) are is further defined below. As indicated above, when determining an epigenetic profile either or both strands of the double stranded genomic DNA or an amplified product therefrom may be assayed. This also applies to a promoter region or other regulatory region.

In an embodiment, the epigenetic profile is determined within a genetic locus which enables the determination of an epigenetic profile in a genome of a cell indicative of a pathological condition and in particular a trinucleotide expansion disorder selected from Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome. Epigenetic changes in intronic, intronic/exonic boundaries and promoter or other regulatory regions in certain genetic loci are instructive to the development of these conditions.

In an embodiment, the genetic locus is the FMR genetic locus and the method comprises screening for a change relative to the control in the extent of epigenetic modification within the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

The extent of epigenetic change is indicative of the presence of severity of the pathological condition or a propensity to developing same. Disease conditions contemplated herein associated with the FMR genetic locus include the trinucleotide expansion disorder FXS and related conditions such as FXTAS, FXPOI, autism, mental retardation, a modified X-chromosome and cognitive impairment. In an embodiment, the present disclosure teaches a method for identifying FXS or a related condition in a human subject, the method comprising screening for a change relative to a control in the extent of epigenetic modification in the FMR genetic locus at a location selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions; and (ii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

wherein a change in extent of epigenetic modification relative to a control is indicative of the presence or severity of the pathological condition or a propensity to develop same.

In an embodiment a method is provided for identifying a trinucleotide expansion disorder in a mammalian subject including a human, the method comprising screening for a change relative to a healthy control in the extent of epigenetic modification within (i) two or more of (a) an intron; (b) an intron/exon boundary; and/or (c) a splicing region; and/or (ii) approximately one seventh or greater of an intron including an intron/exon boundary and/or a splicing region of the FMR genetic locus; wherein a change in extent of epigenetic modification relative to the control is indicative of the presence or severity of the trinucleotide expansion disorder or a propensity to develop same wherein the intron, intron/exon boundary and/or splicing region is selected from the list consisting of:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions; and (iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions.

The present disclosure teaches the manufacture of an assay to identify an epigenetic profile of an FMR genetic locus-associated pathological condition. Reference to an FMR genetic locus-associated pathological condition includes a trinucleotide expansion disorder associated with a change in epigenetic profile from that observed in a healthy subject.

The FMR genetic locus is depicted in part in FIGS. 1A, 4A and 6A. Reference to the "FMR genetic locus" includes the FMR1, FMR4 and ASFMR1 genes and corresponds to Xq27.3. The term "FMR locus" means the "FMR genetic locus". In an embodiment, an aspect taught herein determines that the intronic region downstream of intron 1 comprises Fragile X-related Epigenetic Element 3 as defined by SEQ ID NO:1 or a homolog thereof or a portion or fragment thereof defined by having at least 80% nucleotide sequence identity to SEQ ID NO:1 or which hybridizes to SEQ ID NO:1 or its complementary form under medium stringency conditions; or is intron 2 as defined by SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions. The nucleotide sequence of intron 1 of the FMR1 gene is set forth in SEQ ID NO:3. The nucleotide sequence of genomic FREE2 (D), FREE2 (E) and FREE3 are set forth in SEQ ID NOs:48, 49 and 47, respectively and the present disclosure extends to homology thereof having at least 80% identity to SEQ ID NO:48 or 49 or 47 or which hybridizes to SEQ ID NO:48 or 49 or 47 or a complement thereof under medium stringency conditions. The present disclosure extends to both strands and hence, for example, reference to a particular SEQ ID NO: includes the corresponding complementary sequence.

The present disclosure further contemplates amplifying all or part of an expansion mutation and/or and detecting extent of epigenetic change therein in combination with an epigenetic change (i) two or more of (a) an intron; (b) an intron/exon boundary; and/or (c) a splicing region; and/or (ii) approximately one seventh or greater of an intron including an intron/exon boundary and/or a splicing region of the FMR genetic locus including the FMR1 gene. The extent of epigenetic change in two or more of an intron, an intron/exon boundary and/or a splicing region or in one seventh or greater of an intron within the FMR genetic locus may be determined alone or in combination with extent of $(CGG)_n$ expansion and/or any other epigenetic change therein. The determination of epigenetic change may also be conducted in combination with an assay as contemplated by International Patent Application No. PCT/AU2010/000169 filed on 17 Feb. 2010, the contents of which are incorporated herein by reference in their entirety. In an embodiment, the epigenetic modification is a change in extent of methylation which includes hypermethylation and hypomethylation and profile of methylation. Without limiting the present disclosure to any one theory or mode of action, epigenetic changes in these introns may affect the ability of the introns, intron/exon boundaries and/or splicing regions to transcribe regulatory RNAs which in turn have an effect on bidirectional transcription capability.

Hence, an aspect taught herein is a method for identifying a pathological condition in a mammalian subject including a human, the method comprising screening for a change relative to a control in the extent of epigenetic modification within a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

wherein a change in extent of genetic modification relative to a control is indicative of the presence or severity of the pathological condition or a propensity to develop same.

The present disclosure teaches a method for identifying in a genome of a mammalian cell including a human cell, a pathological condition associated with methylation and other epigenetic change within the FMR locus, the method comprising extracting genomic DNA from the cell and subjecting the DNA to an amplification reaction using primers selective of a region of the FMR genetic locus comprising CpG and/or CpNpG sites, the CpG and CpNpG sites located in a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

and subjecting the amplified DNA to a methylation or other epigenetic assay to determine the extent of epigenetic modification of the DNA wherein a change in extent of epigenetic modification relative to a control is indicative of the presence or severity of the pathological condition or propensity to develop same. In an embodiment, the above assay is useful in detecting FXS or a related condition. Examples of related conditions include FXTAS, FXPOI, autism, mental retardation, a modified X-chromosome and cognitive impairment.

In an embodiment, the epigenetic modification is methylation of CpG and/or CpNpG sites and the assay identifies the extent of methylation change in either strand of double stranded genomic DNA or an amplified fragment thereof including either strand of a promoter region. This change may be an elevation or increase in methylation or a decrease in methylation relative to a control. Alternatively, the epigenetic modification is extent of change in RNA/DNA interaction and/or change in profile of expression of expression of non-coding RNA. Yet in another embodiment, the epigenetic profile is a change in histone modification, changes in acetylation, obiquitylation, phosphorylation, sumoylation, activation or deactivation, chromatin altered transcription factor levels and the like.

In accordance with the present disclosure, a method is provided wherein the extent of methylation or other epigenetic modification provides a quantitative or semi-quantitative or qualitative indication of extent of change in epigenetic profile in (i) two or more of (a) an intron; (b) an intron/exon boundary; and/or (c) a splicing region; and/or (ii) approximately one seventh or greater of an intron including an intron/exon boundary and/or a splicing region within the FMR genetic locus including the FMR1 gene, ASFMR1 gene and promoter gene (including an FMR1 promoter and an ASFMR1 promoter) and as such the level of epigenetic modification defines the severity of the pathological condition alone or in combination with the extent of $(CGG)_n$ expansion. The number of repeats indicate whether a subject is a healthy control or has a Gray Zone (GZ) pathology, premutation (PM) pathology or full mutation (FM) pathology. The method disclosed herein may also be used in conjunction with other assays such as Southern blot or PCR to measure $(CGG)_n$ expansion. Examples of pathology conditions associated with inronic epigenetic changes include the polyQ and non-polyQ conditions listed above.

The present disclosure, however, is not limited to the FMR genetic locus and pathological conditions only associated therewith. Rather, the present disclosure extends to any epigenetic modification in any genetic locus selected from (i) two or more of (a) an intron; (b) an intron/exon boundary; and/or (c) a splicing region; and/or (ii) approximately one seventh greater of an intron including an intron/exon boundary and/or splicing region and which epigenetic change is associated with a pathological condition.

By "approximately one seventh or greater" means from about 14% or greater or nucleotides capable of epigenetic change or modification have undergone a change. This includes 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 67, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% of the nucleotides.

The regions within the FMR genetic locus identified above include a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

As taught herein a "pathological condition" or "disease condition" includes an abnormal condition including a neurodevelopmental condition or a neurodegenerative condition or a non-neurological condition as defined by objective or subjective manifestations of disease. In an embodiment, it is a trinucleotide expansion disorder. A particular condition is FXS or a related condition such as FXTAS, FXPOI, autism, mental retardation, a modified X-chromosome and cognitive impairment. The assay herein described is useful for diagnosing nucleotide expansion diseases or conditions. The assay enabled herein includes a genetic determination to be made to complement other symptom-based diagnoses such as based on behavioral studies or may be made in its own right. The assay may be part of a suit of diagnostic or prognostic genetic assays of embryos, pre- and post-natal subjects. The terms "method", "assay", "system", "test", "determination", "prognostic", "diagnostic", "report" and the like may all be used to describe the methylation assay of selected regions of the FMR genetic locus or other genetic locus. The epigenetic assay such as a methylation assay determines the epigenetic profile or extent of epigenetic change compared to a control which suggests or indicates or is instructive of a disease or condition associated with epigenetic modification of an intron within a genetic locus. The present assay is also useful in population studies such as epidemiological studies including studies of ethnic populations.

Accordingly, the present disclosure further provides a method of identifying a methylation or other epigenetic profile in populations of subjects indicative of a pathological condition, the method comprising screening for a change relative to a control in a statistically significant number of subjects the extent of epigenetic modification in (i) two or more of (a) an intron; (b) an intron/exon boundary; and/or (c) a splicing region; and/or (ii) approximately one seventh or greater of an intron including an intron/exon boundary and/or a splicing region within a genetic locus wherein a change in extent of epigenetic modification is indicative of the presence or severity of the pathological condition or a propensity to develop same.

In an embodiment, the genetic locus is the FMR genetic locus and the region screened for epigenetic change is selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

The present disclosure teaches a method of identifying a methylation or other epigenetic profile in a population of subjects indicative of a pathological condition associated with the FMR locus, the method comprising screening for a change, relative to a control, in a statistically significant number of subjects in the extent of epigenetic modification including extent of change in methylation of CpG and/or CpNpG sites within a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

wherein a change in extent of epigenetic modification is indicative of the presence of the pathological condition or a propensity to develop same in the population. In an embodiment, the pathological condition is FXS or a related condition such as FXTAS, FXPOI, autism, mental retardation, a modified X-chromosome and cognitive impairment.

In accordance with this method, a further step may be conducted of determining the extent of $(CGG)_n$ expansion such as by PCR and/or Southern blot analysis of bisulfite converted and/or non converted DNA. Furthermore, this assay may be conducted with one or more assays contemplated and described in International Patent Application NO. PCT/AU2010/000169 filed on 17 Feb. 2010, the contents of which are incorporated by reference in their entirety.

In an embodiment, the extent of methylation or change in extent of methylation is detected and associated with the pathology condition such as but not limited to an expansion disease or condition.

An epigenetic map and in particular a methylation map of introns, intron/exon boundaries and/or splicing regions within the FMR locus has thus been constructed in accordance with the present disclosure using standard techniques such as high throughput mass spectrometry in the genome of various cells. Any cell type cell may be assayed. These cells include cultured or uncultured Chorionic Villi Sample (CVS) cells, lymphoblasts, blood cells, buccal cells, epithelial cells, fibroblast cells, an amniocyte and EBV transformed lymphoblast cell lines from male and female subjects with either no symptoms or from a spectrum of a pathological condition such as Fragile X mental retardation symptoms. In an embodiment a Fragile X-related Epigenetic Element 3 (FREE3) has been identified within intron 2 of the FMR1 gene. It is proposed that this region [FREE3] or other regions of intron 2 or other introns or parts thereof including intron/exon boundaries and splicing regions downstream of intron 2 of FMR1 or elsewhere in the FMR genetic locus are responsible for the regulation of transcription of FMR4 and ASFMR1 and FMR1 and expression of FMRP. Another region is an ASFMR1 promoter having an initiation site in FREE3 of intron 2 (see FIG. 6A).

In an embodiment, the present disclosure teaches that the extent of methylation in CpG and/or CpNpG sites located within the region downstream of intron 1 or part thereof such as FREE3 closely corresponds to a healthy condition or a level or severity of disease within the spectrum of PM to FM including GZ subjects such a correspondence may be in a further association with other epigenetic modifications within the FMR genetic locus and/or CGG expansion. Furthermore, using the methylation assay, methylation levels of the FREE3 region provide fully quantitative results, which also reflect the degree of X-chromosome modification in females. This can be more informative than methylation patterns of FMR1 CpG islands only which may be biased due to its proximity to a nucleotide expansion, and hence can only provide a qualitative assessment of methylation. Other regions of interest include FREE2 (A), (B), (C) and (D) and the FREE2 (D)/FREE2 (E) boundary defined herein.

Hence, in an embodiment, the present disclosure contemplates a change in extent of methylation which includes an increase or decrease in extent of methylation. There may also be no change in the extent of methylation within an intron of a genetic locus. However, the present disclosure extends to the detection of the change in extent of any epigenetic modification. Such a change or level of methylation in an intron is proposed to be associated with a pathological condition or its severity. In this context, an "intron" includes an intron/exon boundary and/or a splicing region.

A "normal" or "control" in the assay of the present disclosure may be a control genome from a healthy individual performed at the same time or the epigenetic pattern may be compared to a statistically validated standard. In relation to a nucleotide expansion disease condition, a healthy individual includes a subject with a nucleotide repeat within the normal range with no clinically apparent pathological phenotype. For example, in relation to $(CGG)_n$ expansion conditions within the FMR genetic locus, this includes when n is <40.

The present disclosure also explores the relationship between transcription and epigenetic profile of introns or parts thereof and pathological conditions. A "part" includes an intron/exon boundary and splicing region. In an embodiment, methylated CpG sites are identified within FREE3 or intron 2 of the FMR1 gene in subjects with Fragile X mental retardation conditions. In another embodiment, the methylated CpG sites are identified in (i) two or more of (a) an intron; (b) an intron/exon boundary; and/or (c) a splicing region; and/or (ii) approximately one seventh or greater of an intron including an intron/exon boundary and/or a splicing region of the FMR genetic locus. Fragile X mental retardation conditions include FXS as well as FXTAS, FXPOI, autism, mental retardation, a modified X-chromosome and cognitive impairment.

As used herein, the terms "subject", "patient", "individual", "target" and the like refer to any organism or cell of the organism on which an assay of the present disclosure is performed whether for experimental, diagnostic, prophylactic, and/or therapeutic purposes. Typical subjects include both male and female humans but the present disclosure extends to experimental animals such as non-human primates, (e.g., mammals, mice, rats, rabbits, pigs and guinea pigs/hamsters). The "subject" may also be referred to as a population since the present disclosure teaches an assay useful in populations studies including epidemiological studies or assays of ethnic population. In a particular embodiment, the subject is a human. The test may be tailored to human females or human males or pre-natal humans. A control subject has epigenetic (e.g. methylation) profile of a healthy subject.

The terms "Fragile X mental retardation-like condition" and FMR condition" refer to a neurological disease, disorder and/or condition characterized by one or more of the following symptoms: (1) behavioral symptoms, including but not limited to hyperactivity, stereotypy, anxiety, seizure, impaired social behavior, and/or cognitive delay; (2) defective synaptic morphology, such as an abnormal number, length, and/or width of dendritic spines; and/or (3) defective synaptic function, such as enhanced long-term depression (LTD); and/or reduced long-term potentiation (LTP); and/or impaired cognitive ability. The pathological condition is a disease, disorder, and/or condition caused by and/or associated with epigenetic changes within an intron or part thereof within the FMR genetic locus such as downstream of intron 1 of the FMR1 gene. Such epigenetic changes may be alone or in combination with one or more of the following: (1) a mutation in FMR1 or FMR4 or ASFMR1; (2) defective FMR1/FMR4/ASFMR1 expression; (3) increased and/or decreased levels of FMRP; (4) defective FMRP function; (5) increased and/or decreased expression of genes or genetic functions regulated by FMR1, FMRP, FMR4 transcript or ASFMR1 transcript; (6) the increased methylation of FMR locus at CpG or CpNpG sites in the region upstream of FMR1 promoter and/or the region downstream of the $(CGG)_n$ portion of the FMR1 promoter but not including the $(CGG)_n$ portion; (7) an increased and/or decreased function of the FMR locus via miRNAs and/or members of the miRNA pathway; (8) an increased and/or decreased ability of FMRP to interact with its known target RNAs, such as RNAs encoding Racl, microtubule-associated protein IB, activity-regulated cytoskeleton-associated protein, and/or alpha-calcium/calmodulin-dependent protein kinase II; (9) symptoms of FXS, FXTAS, FXPOI, mental retardation, a modified X-chromosome, autism and/or autism spectrum disorders; and/or (10) cognitive impairment. Generally, the FMR condition is a trinucleotide expansion disorder, particularly associated with a changed epigenetic profile from that of a healthy subject.

Those of ordinary skill in the art will appreciate that the teachings of the present disclosure are applicable to any neurodevelopmental or neurodegenerative disorders linked, associated or otherwise influenced by the function of the FMR genetic locus or genes therein such as FMR1, FMR4 and ASFMR1 as well as their promoters or other regulatory regions. Non-neurological disorders are also contemplated herein including FXPOI and other tri-nucleotide expansion disorders.

Furthermore, the present disclosure teaches a range of nucleotide expansion disorders. Conditions and disorders contemplated herein include diseases such as Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome.

The term "genomic DNA" includes all DNA in a cell, group of cells, or in an organelle of a cell and includes exogenous DNA such a transgenes introduced into a cell. Either strand or both strands of double stranded DNA may be assayed.

In a particular aspect, the present disclosure enables the determination of the presence of an FMR genetic locus-associated pathology based on extent of methylation of CpG/CpNpG sites located within (i) an intron downstream of intron 1 of the FMR1 gene or part of an intron; (ii) two or more or (a) an intron; (b) an intron/exon boundary; (c) a splicing region; and/or (iii) approximately one seventh or greater of an intron including an intron/exon boundary and/or a splicing region within the FMR genetic locus. The downstream FMR1 introns may extend beyond the FMR1 gene. In an embodiment, the extent of methylation in part of intron 2 [FREE3] is identified in the FMR1 gene which includes all or part of an ASFMR1 promoter with a transcription start site in FREE3 of intron 2 (see FIG. 6A).

Hence, the present disclosure teaches a method for identifying a methylation or other epigenetic profile in the genome of a cell indicative of a pathological condition associated with the FMR genetic locus, the method comprising screening for a change relative to the control in the extent of epigenetic modification of CpG and/or CpNpG sites located within:

(i) (a) FREE3; (b) intron 2; and (c) an intron downstream of intron 2 or a homolog thereof or a portion or fragment thereof within the FMR1 gene;

(ii) two or more of (a) an intron; (b) an intron/exon boundary; (c) a splicing region within the FMR genetic locus; and/or (iii) approximately one seventh or greater of an intron including an intron/exon boundary and/or a splicing region within the FMR genetic locus;

wherein a change in the extent of epigenetic modification is indicative of the presence of the pathological condition or a propensity to develop same. The nucleotide sequences of FREE3 and intron 2 are set forth in SEQ ID NOs: 1 and 2, respectively and the present disclosure extends to their homologs and portions and parts thereof having at least 80% identity thereto or a nucleotide sequence capable of hybridizing to these sequences or their complementary forms under medium stringency conditions. Reference to FREE3 and an intron such as intron 2 includes portions, fragments, parts, regions and domains thereof. The nucleotide genomic sequences of genome FREE2 (D), FREE2 (E) and FREE3 are set forth in SEQ ID NOs:48, 49 and 47, respectively and the present disclosure extends to their homologs and portions and parts thereof having at least 80% identity thereto or a nucleotide sequence capable of hybridizing to these sequences or their complementary forms under medium stringency conditions. Reference to FREE3 and an intron such as intron 2 includes portions, fragments, parts, regions and domains thereof as well as one or both strands of double stranded genomic DNA.

In a particular embodiment, the epigenetic modification is methylation and RNA/DNA interactions.

The present disclosure further contemplates a method for identifying a pathological condition in a subject associated with methylation within the FMR locus, the method comprising extracting genomic DNA from a cell of the subject and subjecting the DNA to an amplification reaction using primers selective of a region of the FMR genetic locus comprising CpG and/or CpNpG sites, the CpG and CpNpG sites located in the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

and subjecting the DNA to a methylation assay to determine the extent of methylation of the DNA wherein a change in extent of methylation relative to a control is indicative of the presence or severity of the pathological condition or propensity to develop same.

In an embodiment, the present disclosure teaches a method for identifying FXS or a related condition associated with methylation of the FMR genetic locus, the method comprising extracting genomic DNA from a cell of the subject and subjecting the DNA to an amplification reaction using primers selective of a region of the FMR genetic locus comprising CpG and/or CpNpG sites, the CpG and CpNpG sites located in the FMR genetic locus within a region selected from:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene including the FREE2 (D) region or FREE2 (D)/(E) boundary.

and subjecting the DNA to a methylation assay to determine the extent of methylation of the DNA wherein a change in extent of methylation relative to a control is indicative of the presence or severity of the pathological condition or propensity to develop same.

Any methylation assay may be employed such as methylation sensitive PCR, methylation specific melting curve analysis (MS-MCA) or high resolution melting (MS-HRM) [Dahl et al., *Clin Chem* 53(4):790-793, 2007; Wojdacz et al., *Nucleic Acids Res.* 35(6):e41, 2007]; quantification of CpG methylation by MALDI-TOF MS (Tost et al., *Nucleic Acids Res* 31(9):e50, 2003); methylation specific MLPA (Nygren et al., *Nucleic Acids Res.* 33(14):e128, 2005); methylated-DNA precipitation and methylation-sensitive restriction enzymes (COMPARE-MS) [Yegnasubramanian et al., *Nucleic Acids Res.* 34(3):e19, 2006] or methylation sensitive oligonucleotide microarray (Gitan et al., *Genome Res.* 12(1): 158-164, 2002), as well as via antibodies. Other assays include NEXT generation (GEN) and DEEP sequencing or pyrosequencing. Another assay is single molecule (SMRT) sequencing.

Insofar as the methylation assay may involve an amplification, an amplification methodology may be employed. Amplification methodologies contemplated herein include the polymerase chain reaction (PCR) such as disclosed in U.S. Pat. Nos. 4,683,202 and 4,683,195; the ligase chain reaction (LCR) such as disclosed in European Patent Application No. EP-A-320 308 and gap filling LCR (GLCR) or variations thereof such as disclosed in International Patent Publication No. WO 90/01069, European Patent Application EP-A-439 182, British Patent No. GB 2,225,112A and International Patent Publication No. WO 93/00447. Other amplification techniques include Qβ replicase such as described in the literature; Stand Displacement Amplification (SDA) such as described in European Patent Application Nos. EP-A-497 272 and EP-A-500 224; Self-Sustained Sequence Replication (3SR) such as described in Fahy et al., *PCR Methods Appl.* 1(1):25-33, 1991) and Nucleic Acid Sequence-Based Amplification (NASBA) such as described in the literature.

A PCR amplification process is particularly useful in the practice of the present disclosure.

In an embodiment, prior to the PCR, either essentially all cytosines in the DNA sample are selectively delaminated, but 5-methylcytosines remain essentially unchanged or essentially all 5-methylcytosines in the DNA sample are selectively delaminated, but cytosines remain essentially unchanged. Cytosine-guanine (CpG) dinucleotides and CpNpG trinucleotides are detected, allowing conclusions about the methylation state of cytosines in the CpG dinucleotides and CpNpG trinucleotide in the DNA sample. This delamination is generally performed using a bisulfite reagent. After bisulfite treatment, the 5-methylcytosines residues are converted to thymine (T).

The sample DNA is only amplified by chosen PCR primers if a certain methylation state is present at a specific site in the sample DNA the sequence context of which is essentially complementary to one or more of the chosen PCR primers. This can be done using primers annealing selectively to bisulfite treated DNA which contains in a certain position either a TG or a CG or CNG, depending on the methylation status in the genomic DNA. Primers are designed based on particular regions around CpG and/or CpNpG sites or other FMR1 intronic regions. Introns or parts thereof including intron/exon boundaries and splicing regions downstream of intron 2 of FMR1 or downstream of the FMR1 gene itself are also contemplated herein as are (i) two or more of (a) an intron; (b) an intron/exon boundary; and/or (c) a splicing region; and/or (ii) approximately one seventh or greater of an intron including an intron/exon boundary and/or a splicing region, of the FMR genetic locus.

A technology which can alternatively be employed for methylation analysis utilizes base-specific cleavage followed by MALDI-TOF mass spectrometry on DNA after bisulfite treatment, where all the 5-methylcytosines residues are converted to thymine (T) or where all unmethylated cytosines residues are not converted to thymine (T). Primers are designed based on particular regions around CpG and/or CpNpG sites or other FMR1 intronic regions or downstream thereof. Primer sequences are designed to amplify without bias both converted and unconverted sequences using the PCR amplification process under the medium to high stringency conditions. The PCR products are in vitro transcribed and subjected to base specific cleavage and fragmentation analysis using MALDI-TOF MS. The size ratio of the cleaved products provides quantitative methylation estimates for CpG sites within a target region. The shift in mass for non-methylated (NM) from methylated (M) fragments for a single CpG site is −16 daltons due to the presence of an adenosine residue in the place of a guanosine. A software is then used to calculate methylation for each fragment based on this difference in mass, where the output methylation ratios are the intensities of methylated signal/[methylated+unmethylated signal]. If the fragment size overlaps for different CpGs, their methylation output ratio is calculated based on the sum of intensities for methylated/[methylated+unmethylated signal]. To distinguish how well the methylation output ratio for multiple fragments of a similar size represented methylation of separate CpG sites, for some amplicons both cytosine and thymidine cleave reactions can be performed (that produced fragments of different size) prior to fragment analysis. Silent peaks (S)—fragments of unknown origin, should not be taken into consideration if their size does not overlap with the fragments of interest. Methylation of CpG sites that have silent peaks (S) that overlap with the fragments of interest should be included in the analysis.

Hence, a method is provided for determining the methylation profile of one or more CpG or CpNpG sites located within the genome of a eukaryotic cell or group of cells, the method comprising obtaining a sample of genomic DNA from the cell or group of cells and subjecting the genomic DNA to primer-specific amplification within an intron of a genetic locus and assaying for extent of methylation relative to a control, including a change in the extent of methylation and associating this change with a pathological condition.

A "nucleic acid" as used herein, is a covalently linked sequence of nucleotides in which the 3' position of the phosphorylated pentose of one nucleotide is joined by a phosphodiester group to the 5' position of the pentose of the next nucleotide and in which the nucleotide residues are linked in specific sequence; i.e. a linear order of nucleotides. A "polynucleotide" as used herein, is a nucleic acid containing a sequence that is greater than about 100 nucleotides in length. An "oligonucleotide" as used herein, is a short polynucleotide or a portion of a polynucleotide. An oligonucleotide typically contains a sequence of about two to about one hundred bases. The word "oligo" may be used in place of the word "oligonucleotide". The term "oligo" also includes a particularly useful primer length in the practice of the present disclosure of up to about 10 nucleotides.

As used herein, the term "primer" refers to an oligonucleotide or polynucleotide that is capable of hybridizing to another nucleic acid of interest under particular stringency conditions. A primer may occur naturally as in a purified restriction digest or be produced synthetically, by recombinant means or by PCR amplification. The primer may be selected to amplify either or both stands of double stranded genomic DNA. This includes a promoter or other regulatory region. The terms "probe" and "primers" may be used interchangeably, although to the extent that an oligonucleotide is used in a PCR or other amplification reaction, the term is generally "primer". The ability to hybridize is dependent in part on the degree of complementarity between the nucleotide sequence of the primer and complementary sequence on the target DNA.

The terms "complementary" or "complementarity" are used in reference to nucleic acids (i.e. a sequence of nucleotides) related by the well-known base-pairing rules that A pairs with T or U and C pairs with G. For example, the sequence 5'-A-G-T-3' is complementary to the sequence 3'-T-C-A-5' in DNA and 3'-U-C-A-5' in RNA. Complementarity can be "partial" in which only some of the nucleotide bases are matched according to the base pairing rules. On the other hand, there may be "complete" or "total" complementarity between the nucleic acid strands when all of the bases are matched according to base-pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the present disclosure. The term "substantially complementary" is used to describe any primer that can hybridize to either or both strands of the target nucleic acid sequence under conditions of low stringency as described below or, preferably, in polymerase reaction buffer heated to 95° C. and then cooled to room temperature. As used herein, when the primer is referred to as partially or totally complementary to the target nucleic acid, that refers to the 3'-terminal region of the probe (i.e. within about 10 nucleotides of the 3'-terminal nucleotide position).

As discussed above, when reference is made to a genomic nucleotide sequence, the present disclosure extends to its complementary strand sequence. Either or both strands may be assayed from epigenetic change.

Reference herein to a stringency in relation to hybridization includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C. Reference to at least "80% identity" includes 80, 81, 82, 83, 84, 85, 86, 87, 88, 89, 90, 91, 92, 93, 94, 95, 96, 97, 98, 99 and 100%.

The present disclosure enables the determination of a methylation or other epigenetic profile of sites within an intron, intron/exon boundary and/or splicing region of a genetic locus in a genome of a eukaryotic cell or group of cells, the method comprising obtaining a sample of genomic DNA from the cell or group of cells, subjecting the digested DNA to an amplification reaction using primers selected to amplify a region of the genetic locus selected from:

(i) two or more of (a) an intron; (b) an intron/exon boundary; and/or (c) a splicing region; and/or (ii) approximately one seventh or greater of an intron including an intron/exon boundary and/or a splicing region of the genetic locus;

and then subjecting the amplified DNA to methylation or other epigenetic detection means to determine relative to control the extent of methylation or other epigenetic modification wherein a change in epigenetic modification or other epigenetic modification relative to the control is indicative of a pathological condition associated with the genetic locus.

Examples of pathological conditions include Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubropallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome.

In an embodiment, the present disclosure enables determination of a methylation profile of the sites within the FMR locus in a genome of a eukaryotic cell or group of cells, the methylation profile comprising the extent or level of methylation within the FMR locus, the method comprising obtaining a sample of genomic DNA from the cell or group of cells, subjecting the digested DNA to an amplification reaction using primers selected to amplify a region of the FMR genetic locus selected from:

(i) (a) FREE3; (b) intron 2; and (c) an intron, intron/exon boundary and/or splicing region downstream of intron 2 or part thereof;

(ii) two or more of (a) an intron; (b) an intron/exon boundary; (c) a splicing region; and (iii) approximately one seventh or greater of an intron including an intron/exon boundary and/or a splicing region within the FMR genetic locus;

and then subjecting the amplified DNA to methylation detection means to determine relative to control the extent of methylation wherein a change in methylation relative to the control is indicative of a pathological condition associated with the FMR genetic locus.

In an embodiment, the region amplified within the FMR genetic locus is selected from:

(i) the 3' boundary of the FREE2 region and the FMR1 promoter located between CpG unit 1 of the FREE2 (E) amplicon and CpG unit 2/3 of the FREE2 (E) amplicon;

(ii) the FREE2 region alone or in combination with the FREE1 region;

(iii) the FREE3 region; and (iv) an intron including an intron/exon boundary and/or splicing region downstream of intron 1 within the FMR1 gene including the FREE2 (D) region or FREE2 (D)/(E) boundary.

The present disclosure further provides a methylation profile of the sites within the FMR locus in a genome of a eukaryotic cell or group of cells, the methylation profile comprising the extent or level of methylation within the FMR locus, the method comprising obtaining a sample of genomic DNA from the cell or group of cells, subjecting the digested DNA to an amplification reaction using primers selected to amplify FREE3 within the FMR1 gene and then subjecting the amplified DNA to methylation detection means to determine relative to control the extent of methylation wherein a change in methylation relative to the control is indicative of a pathological condition associated with the FMR genetic locus.

In an embodiment, the present disclosure enables determination of a methylation profile of the sites within the FMR locus in a genome of a eukaryotic cell or group of cells, the methylation profile comprising the extent or level of methylation within the FMR locus, the method comprising obtaining a sample of genomic DNA from the cell or group of cells, subjecting the digested DNA to an amplification reaction using primers selected to amplify all or part of FREE3 and then subjecting the amplified DNA to methylation detection means to determine relative to control the extent of methylation wherein a change in methylation relative to the control is indicative of a pathological condition associated with the FMR genetic locus. An adverse change in methylation or other epigenetic profile is associated with FXS or related condition such as FXTAS, FXPOI, autism, mental retardation and cognitive impairment.

As indicated above, the cells may be a lymphoblast, a CVS cell, a blood cell, a buccal cell, epthelial cell, fibroblast cell, an amniocyte or an EBV transformed lymphoblast cell line. In addition, the methylation profile may be determined or one or both alleles a genetic locus and in selected cells where mosaicism has occurred. In particular, the extent of methylation can determine homozygosity or heterozygosity or mosaicism. Reference to "mosaicism" includes the situation wherein two or more populations of cells have different genotypes or epigenetic profiles at the genetic locus.

The diagnostic assay herein can also detect heterozygosity or mosaicism where the methylation pattern is indicative of, for example, in relation to an FMR genetic locus-associated pathology, an FM. The latter may also be conducted in combination with an assay to detect $(CGG)_n$ expansion.

The present disclosure also teaches kits for determining the methylation or other epigenetic profile of one or more nucleotides at one or more sites within the genome of a eukaryotic cell or group of cells. The kits may comprise many different forms but in one embodiment, the kits comprise reagents for the bisulfite methylation assay.

A further embodiment of the present disclosure is a kit for the use in the above methods comprising primers to amplify an intron within a genetic locus.

In an embodiment, the present disclosure provides a use of primers which amplify regions of the FMR genetic locus, comprising CpG and/or CpNpG sites located within:

(i) two or more of (a) an intron; (b) an intron/exon boundary; and/or (c) a splicing region;

(ii) approximately one seventh or greater of an intron including an intron/exon boundary and/or a splicing region;

(iii) the 3' boundary of the FREE2 region and the FMR1 promoter located between CpG unit 1 of the FREE2 (E) amplicon and CpG unit 2/3 of the FREE2 (E) amplicon;

(iv) the FREE2 region alone or in combination with the FREE1 region;

(v) the FREE3 region; and (vi) an intron including an intron/exon boundary and/or splicing region downstream of intron 1 within the FMR1 gene.

in the manufacture of a diagnostic kit or device to detect methylation of the FMR locus-associated with a pathological condition.

In relation to one embodiment, a kit is provided for the use in the above methods comprising primers identified by SEQ ID NOs:6 through 11 to amplify an intronic site within the FMR1 genetic locus. The nucleotide sequences in SEQ ID NOs:6 through 11 comprise primer and tag sequences. The present disclosure extends to SEQ ID NO:6 through 11 as well as primer only portions therein. The primers may also include primers disclosed in PCT/AU2010/000169.

The kit may also comprise instructions for use.

Conveniently, the kits are adapted to contain compartments for two or more of the above-listed components. Furthermore, buffers, nucleotides and/or enzymes may be combined into a single compartment.

As stated above, instructions optionally present in such kits instruct the user on how to use the components of the kit to perform the various methods of the present disclosure. It is contemplated that these instructions include a description of the detection methods of the subject disclosure, including detection by gel electrophoresis.

The present disclosure further enables kits which contain a primer for a nucleic acid target of interest with the primer being complementary to a predetermined nucleic acid target. In another embodiment, the kit contains multiple primers or probes, each of which contains a different base at an interrogation position or which is designed to interrogate different target DNA sequences. In a contemplated embodiment, multiple probes are provided for a set of nucleic acid target sequences that give rise to analytical results which are distinguishable for the various probes. The multiple probes may be in microarray format for ease of use.

The kit may comprise a vessel containing a purified and isolated enzyme whose activity is to release one or more nucleotides from the 3' terminus of a hybridized nucleic acid probe and a vessel containing pyrophosphate. In one embodiment, these items are combined in a single vessel. It is contemplated that the enzyme is either in solution or provided as a solid (e.g. as a lyophilized powder); the same is true for the pyrophosphate. Preferably, the enzyme is provided in solution. Some contemplated kits contain labeled nucleic acid probes. Other contemplated kits further comprise vessels containing labels and vessels containing reagents for attaching the labels. Microtiter trays are particularly useful and these may comprise from two to 100,000 wells or from about six to about 10,000 wells or from about six to about 1,000 wells.

Another important application is in the high throughput screening of agents which are capable of demethylation genomes and in particular intronic regions within genomes. This may be important, for example, in de-differentiating cells and/or treating pathological conditions.

The present disclosure further enables a method for screening for an agent which modulates methylation or other epigenetic modification of a genetic locus, the method comprising screening for a change relative to a control in the extent of methylation or other epigenetic modification in an intron, intron/exon boundary and/or splicing region within the genetic locus which is associated with a pathological condition in the presences or absence of an agent to be tested, wherein an agent is selected if it induces a change in the extent of methylation or other epigenetic change. Agents include de-methylation agents and hyper-methylation agents, global and site specific.

In an embodiment, a method is also provided for screening for an agent which modulates epigenetic modification of an FMR genetic locus in a mammalian cell including a human cell, the method comprising screening for a change relative to a healthy control in the extent of epigenetic change in (i) two or more of (a) an intron; (b) an intron/exon boundary; and/or (c) a splicing region; and/or (ii) approximately one seventh or greater of an intron including an intron/exon boundary and/or a splicing region of the FMR genetic locus; wherein the intron, intron/exon boundary and/or splicing region is selected from the list consisting of:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

in the presence or absence of an agent to be tested wherein the agent is selected if it induces a change in extent of epigenetic modification. Such an agent is useful in the treatment of a trinucleotide expansion disorder such as associated with a change in epigenetic profile from that of a healthy subject.

In an embodiment, a method is provided for screening for an agent which modulates methylation of an FMR genetic locus in a mammalian cell including a human cell, the method comprising screening for a change relative to a control in the extent of methylation in a region selected from:

(i) Fragile X-related Epigenetic Element 3 in FMR1 comprising the nucleotide sequence set forth in SEQ ID NO:1 or a homolog thereof or portion or fragment thereof defined by having at least 80% nucleotide sequence identity to SEQ ID NO:1 or which hybridizes to SEQ ID NO:1 or its complementary form under medium stringency conditions;

(ii) intron 2 of FMR1 comprising the nucleotide sequence set forth in SEQ ID NO:2 or a homolog thereof or a portion or fragment thereof defined by having at least 80% nucleotide sequence identity to SEQ ID NO:2 or which hybridizes to SEQ ID NO:2 or its complementary form under medium stringency conditions;

(iii) genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 of FMR1 or a homolog thereof or a portion or fragment thereof;

(v) two or more of (a) an intron; (b) an intron/exon boundary; and/or (c) a splicing regions within the FMR genetic locus; and (vi) approximately one seventh or greater of an intron including an intron/exon boundary and/or a splicing region within the FMR genetic locus;

in the presence or absence of an agent to be tested wherein the agent is selected if it induces a change in extent of methylation.

The present disclosure further enables a method for monitoring the treatment of a genetic locus-associated disease including a nucleotide expansion disease in which the treatment modulates the methylation of the genetic locus, the method comprising monitoring for a change relative to a control or a pre and post-treatment sample in the extent of methylation within an intron, intron/exon boundary and/or splicing region of the genetic locus.

By "monitoring" includes diagnosis, prognosis, pharmacoresponsiveness, pharmacosensitivity, level of disease progression or remission, improving or declining health of a subject and the like.

As indicated above, conditions and disorders contemplated herein include a range of nucleotide expansion diseases such as but not limited to Fragile X syndrome (FXS), Fragile X-associated tremor or ataxia (FXTAS), Fragile X-associated primary ovarian insufficiency (FXPOI), autism, mental retardation, cognitive impairment, a modified X-chromosome, Huntington's disease (HD), dentatorubro-pallid-oluysiantrophy (DRPLA), spinobulbar muscular atrophy or Kennedy disease (SBMA), spinocerebella ataxia Type 1 (SCA1), spinocerebella ataxia Type 2 (SCA2), spinocerebella ataxia Type 3 or Machado-Joseph disease (SCA3), spinocerebella ataxia Type 6 (SCA6), spinocerebella ataxia Type 7 (SCAT), spinocerebella ataxia Type 17 (SCA17), Fragile XE mental retardation (FRAXE), Friedrich's ataxia (FRDA), Fragile type, folic acid type, rare 12 (FRA12A), myotonic dystrophy (DM), spinocerebella ataxia (SCAB) and spinocerebella ataxias Type 12 (SCA12), Klinefelter's syndrome and Turner's syndrome. Reference to a "modified" X-chromosome includes skewed X-inactivation, inversions, deletions, duplications, hybrids and any modification leading to X-chromosome inactivation. A particular condition associated with epigenetic changes to the FMR genetic locus include FXS and related disorders such as FXTAS, FXPOI, autism, mental retardation, a modified X-chromosome and cognitive impairment.

The present disclosure further teaches the identification of genes having introns with CpG or CpNpG sites or other methylation-sensitive restriction sites. The identification of these sites permits identification of potential regulatory regions which can be targeted by agonists or antagonists of abnormal gene expression.

In cases where the gene is methylated and silenced in affected individuals or tissues, compounds are screened in high throughput fashion in stable cell lines or individuals to identify drugs that result in demethylation and reactivation of the affected gene. Alternatively, a normal active copy of the affected gene is transfected as a transgene into cells to correct the defect. Such transgenes are introduced with modulating sequences that protect the transgene from methylation and keep it unmethylated and transcriptionally active.

In cases where the gene is unmethylated and transcriptionally active or transcriptionally over-active in affected individuals or tissues, compounds are screened in high throughput fashion in stable cell lines to identify drugs that result in methylation and silencing of the affected gene. Alternatively, a transgene encoding a double stranded RNA homologous to the affected sequences or homologs thereof, are transfected as a transgene into cells to methylate the gene, silence it and thereby correct the defect. Such double stranded RNA-encoding transgenes are introduced with modulating sequences which protect it from methylation, keep it transcriptionally active and producing double stranded RNA.

The present disclosure further provides a computer program and hardware which monitors the changing state, if any, of extent of methylation over time or in response to therapeutic and/or behavioral modification. Such a computer program has important utility in monitoring disease progression, response to intervention and may guide modification of therapy or treatment. The computer program is also useful in understanding the association between increasing methylation and disease progression.

The computer program monitors in a quantitative or semi-quantitative manner one or more features including extent of methylation or other epigenetic modification in an intron of a genetic locus. In addition, the length of a nucleotide expansion may be determined or any epigenetic changes therein. In relation to a neuropathological condition, a behavioral assessment may be made using criteria associated with normal subjects or subjects considered to be suffering with a disease condition. For example, cognitive ability can be measured as well as the general phenotype or clinical manifestations in subjects with a neurodevelopmental or neurodegenerative condition or other condition associated with nucleotide expansion.

Thus, in accordance with the present disclosure, values are assigned to the listed features which are stored in a machine-readable storage medium, which is capable of processing the data to provide an extent of disease progression or change in methylation or other epigenetic modification for a subject.

In an aspect, the disclosure teaches a computer program product for assessing progression of a pathological condition associated with the FMR locus in a subject, the product comprising:

(1) assigning a value to one or more of:
(a) change in of methylation or other epigenetic modification relative to a control in FREE3 of FMR1 comprising the nucleotide sequence set forth in SEQ ID NO:1 or a homolog thereof or portion or part thereof defined by having at least 80% nucleotide sequence identity to SEQ ID NO:1 or which hybridizes to SEQ ID NO:1 or its complementary form under medium stringency conditions;
(b) change of methylation or other epigenetic modification relative to a control in intron 2 of FMR1 comprising the nucleotide sequence set forth in SEQ ID NO:2 or a homolog thereof or portion or part thereof defined by having at least 80% nucleotide sequence identity to SEQ ID NO:2 or which hybridizes to SEQ ID NO:2 or its complementary form under medium stringency conditions;
(c) change in methylation or other epigenetic modification relative to a control in genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;
(d) change of methylation in an intron, intron/exon boundary and/or splicing region downstream of intron 2 of FMR1 or a homolog thereof or a portion or fragment thereof;
(e) two or more of (i) an intron; (ii) an intron/exon boundary; (iii) a splicing region within the FMR genetic locus;

(f) approximately one seventh or greater of an intron including an intron/exon boundary and/or a splicing region within the FMR genetic locus;
(g) length of $(CGG)_n$ expansion within the FMR genetic locus when considered in combination with (a) and/or (b);
(h) general phenotype or clinical manifestations in subjects with a neurodevelopmental or neurodegenerative condition;
(i) behavioral assessment criteria associated with normal subjects, PM subjects, GZ subjects and FM subjects;
(j) cognitive ability;
(k) extent of transcription of genes within the FMR locus with the proviso that if any one of (d) through (k) is determined then one or more of (a) through (c) is also determined;
(2) means to converting the value to a code; and
(3) means to store the code in a computer readable medium and compare code to a knowledge database to determine whether the code corresponds to a pathological condition.

In a related aspect, the disclosure teaches a computer for assessing an association between extent of methylation or other epigenetic modification within the FMR locus, the FMR locus and progression of a disease condition wherein the computer comprises:
(1) a machine-readable data storage medium comprising a data storage material encoded with machine-readable data, wherein the machine-readable data comprise values associated with the features of one or more of:
(a) change in of methylation or other epigenetic modification relative to a control in FREE3 of FMR1 comprising the nucleotide sequence set forth in SEQ ID NO:1 or a homolog thereof or portion or part thereof defined by having at least 80% nucleotide sequence identity to SEQ ID NO:1 or which hybridizes to SEQ ID NO:1 or its complementary form under medium stringency conditions upstream;
(b) change of methylation or other epigenetic modification relative to a control in CpG and/or CpNpG islands and island shores in intron 2 of the FMR1 gene comprising the nucleotide sequence set forth in SEQ ID NO:2 or a homolog thereof or portion or part thereof defined by having at least 80% nucleotide sequence identity to SEQ ID NO:2 or which hybridizes to SEQ ID NO:2 or its complementary form under medium stringency conditions;
(c) change in methylation or other epigenetic modification relative to a control in genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;
(d) change in methylation of an intron, intron/exon boundary and/or splicing region downstream of intron 2 of FMR1 or a homolog thereof or a portion or fragment thereof;
(e) two or more of (i) an intron; (ii) an intron/exon boundary; (iii) a splicing region within the FMR genetic locus;
(f) approximately one seventh or greater of an intron including an intron/exon boundary and/or a splicing region within the FMR genetic locus;
(g) length of $(CGG)_n$ expansion within the FMR genetic locus when considered in combination with (a) and/or (b);
(h) general phenotype or clinical manifestations in subjects with a neurodevelopmental or neurodegenerative condition;
(i) behavioral assessment criteria associated with normal subjects, PM subjects, GZ subjects and FM subjects;
(j) cognitive ability;
(k) extent of transcription of genes within the FMR locus with the proviso that if one or more of (d) through (k) is determined, then one or more of (a) through (c) or (k) is also determined;
(2) means to converting the value to a code; and
(3) means to store the code in a computer readable medium and compare code to a knowledge database to determine whether the code corresponds to a pathological condition.

The computer system of the present disclosure may also be linked to detection systems such as MALDI-TOF mass spectrometry machines.

The present disclosure further provides a web-based system where data on extent of methylation within a genetic locus (optionally together with clinical phenotype) are provided by a client server to a central processor which analyzes and compares to a control and optionally considers other information such as patient age, sex, weight and other medical conditions and then provides a report, such as, for example, a risk factor for disease severity or progression or status or response to treatment or an index of probability of a genetic locus-associated pathology in a subject.

Hence, knowledge-based computer software and hardware also form part of the present disclosure.

In an embodiment, the assays herein may be used in existing or newly developed knowledge-based architecture or platforms associated with pathology services. For example, results from the assays are transmitted via a communications network (e.g. the internet) to a processing system in which an algorithm is stored and used to generate a predicted posterior probability value which translates to the index of disease probability which is then forwarded to an end user in the form of a diagnostic or predictive report.

The assay may, therefore, be in the form of a kit or computer-based system which comprises the reagents necessary to detect the extent of methylation or other epigenetic modification within the genetic locus and includes computer hardware and/or software to facilitate determination and transmission of reports to a clinician.

The assay of the present disclosure permits integration into existing or newly developed pathology architecture or platform systems. For example, the present disclosure contemplates a method of allowing a user to determine the status of a subject with respect to an FMR locus-associated pathology, the method including:
(a) receiving data in the form of extent of methylation or other epigenetic modification at a site within:
(A) the FMR1 gene selected from:
(i) Fragile X-related Epigenetic Element 3 [FREE3] comprising the nucleotide sequence set forth in SEQ ID NO:1 or a homolog thereof or portion or part thereof defined by having at least 80% nucleotide sequence identity to SEQ ID NO:1 or which hybridizes to SEQ ID NO:1 or its complementary form under medium stringency conditions;

(ii) intron 2 comprising the nucleotide sequence set forth in SEQ ID NO:2 or a homolog thereof or portion or part thereof defined by having at least 80% nucleotide sequence identity to SEQ ID NO:2 or which hybridizes to SEQ ID NO:2 or its complementary form under medium stringency conditions; and (iii) change in methylation or other epigenetic modification relative to a control in genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 or a homolog thereof or a fragment or portion thereof;

(B) the FMR genetic locus selected from:

(i) two or more of (a) an intron; (b) an intron/exon boundary; and/or (c) a splicing region; or (ii) approximately one seventh or greater of an intron including an intron/exon boundary and/or a splicing region;

wherein the extent of methylation or other epigenetic modification provides a correlation to the presence, state, classification or progression of the pathology; by transferring the data from the user via a communications network;

(c) processing the subject data via multivariate or univariate analysis to provide a disease value;

(d) determining the status of the subject in accordance with the results of the disease value in comparison with predetermined values; and (e) transferring an indication of the status of the subject to the user via the communications network. Reference to the multivariate or univariate analysis includes an algorithm which performs the multivariate or univariate analysis function.

Conveniently, the method generally further includes:

(a) having the user determine the data using a remote end station; and (b) transferring the data from the end station to the base station via the communications network.

The base station can include first and second processing systems, in which case the method can include:

(a) transferring the data to the first processing system;

(b) transferring the data to the second processing system; and (c) causing the first processing system to perform the multivariate analysis function to generate the disease value.

The method may also include:

(a) transferring the results of the multivariate or univariate analysis function to the first processing system; and (b) causing the first processing system to determine the status of the subject.

In this case, the method also includes at least one of:

(a) transferring the data between the communications network and the first processing system through a first firewall; and (b) transferring the data between the first and the second processing systems through a second firewall.

The second processing system may be coupled to a database adapted to store predetermined data and/or the multivariate analysis and/or univariate analysis function, the method including:

(a) querying the database to obtain at least selected predetermined data or access to the multivariate or univariate analysis function from the database; and (b) comparing the selected predetermined data to the subject data or generating a predicted probability.

The second processing system can be coupled to a database, the method including storing the data in the database.

The method can also include having the user determine the data using a secure array, the secure array of elements capable of determining the extent of methylation in an intron with a genetic locus and having a number of features each located at respective position(s) on the respective code. In this case, the method typically includes causing the base station to:

(a) determine the code from the data;

(b) determine a layout indicating the position of each feature on the array; and (c) determine the parameter values in accordance with the determined layout, and the data.

The method can also include causing the base station to:

(a) determine payment information, the payment information representing the provision of payment by the user; and (b) perform the comparison in response to the determination of the payment information.

The present disclosure also teaches a base station for determining the status of a subject with respect to a pathology associated with a genetic locus such as the FMR locus, the base station including:

(a) a store method;

(b) a processing system, the processing system being adapted to;

(c) receive subject data from the user via a communications network, the data; including extent of methylation within the genetic locus wherein the level or methylation or epigenetic modification relative to a control provides a correlation to the presence, state, classification or progression of the pathology;

(d) performing an algorithmic function including comparing the data to predetermined data;

(e) determining the status of the subject in accordance with the results of the algorithmic function including the comparison; and (f) output an indication of the status of the subject to the user via the communications network.

The processing system can be adapted to receive data from a remote end station adapted to determine the data.

The processing system may include:

(a) a first processing system adapted to:
(i) receive the data; and
(ii) determine the status of the subject in accordance with the results of the multivariate or univariate analysis function including comparing the data; and (b) a second processing system adapted to:
(i) receive the data from the processing system;
(ii) perform the multivariate or univariate analysis function including the comparison; and
(iii) transfer the results to the first processing system.

The determination of the extent of methylation or other epigenetic modification within the FMR locus at a site within the FMR1 gene selected from:

(i) Fragile X-related Epigenetic Element 3 [FREE3] comprising the nucleotide sequence set forth in SEQ ID NO:1 or a homolog thereof or portion or part thereof defined by having at least 80% nucleotide sequence identity to SEQ ID NO:1 or which hybridizes to SEQ ID NO:1 or its complementary form under medium stringency conditions;

(ii) intron 2 comprising the nucleotide sequence set forth in SEQ ID NO:2 or a homolog thereof or portion or part thereof defined by having at least 80% nucleotide sequence identity to SEQ ID NO:2 or which hybridizes to SEQ ID NO:2 or its complementary form under medium stringency conditions;

(iii) change in methylation or other epigenetic modification relative to a control in genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;

(iv) an intron, intron/exon boundary and/or splicing region downstream of intron 2 or a homolog thereof or a portion or fragment thereof;

(v) two or more of (a) an intron; (b) an intron/exon boundary; and/or (c) a splicing region; or (vi) approximately one seventh or greater of an intron including an intron/exon boundary and/or a splicing region within the FMR genetic locus;

enables establishment of a diagnostic or prognostic rule based on the extent of methylation relative to controls. Alternatively, the diagnostic or prognostic rule is based on the application of a statistical and machine learning algorithm. Such an algorithm uses relationships between methylation profiles and disease status observed in training data (with known disease status) to infer relationships which are then used to predict the status of patients with unknown status. An algorithm is employed which provides an index of probability that a patient has an FMR locus-associated pathology. The algorithm performs a multivariate or univariate analysis function.

Hence, the present disclosure teaches a diagnostic rule based on the application of statistical and machine learning algorithms. Such an algorithm uses the relationships between epigenetic profile and disease status observed in training data (with known disease status) to infer relationships which are then used to predict the status of patients with unknown status. Practitioners skilled in the art of data analysis recognize that many different forms of inferring relationships in the training data may be used without materially changing the present disclosure.

The present disclosure teaches a knowledge base of training data comprising extent of methylation within a genetic locus such as the FMR genetic locus from a subject with locus-associated pathology to generate an algorithm which, upon input of a second knowledge base of data comprising levels of the same biomarkers from a patient with an unknown pathology, provides a probability that predicts the nature of unknown pathology or response to treatment.

The term "training data" includes knowledge of the extent of methylation relative to a control. A "control" includes a comparison to levels in a healthy subject devoid of a pathology or is cured of the condition or may be a statistically determined level based on trials.

The present disclosure contemplates, therefore, the use of the methylation, including epigenetic profile of intronic sites within the FMR genetic locus and in particular the FMR1 gene to assess or determine the status of a subject with respect to disease, to stratify a subject relative to normal controls or unhealthy subjects, to provide a prognosis of recovery or deterioration and/or to determine the pharmacoresponsiveness or pharmacosensitivity of a subject to treatment or an agent for use in treatment and/or determine applicability for other treatment options including behavioural intervention, and the like. By "intronic sites" includes intron/exon boundaries and splicing regions.

Hence, another aspect enabled herein is a method of allowing a user to determine the status, prognosis and/or treatment response of a subject with respect to an FMR locus-associated pathology, the method including:

(a) receiving data in the form of extent of methylation or other epigenetic modification at a site in:
(i) FMR1 gene selected from:
(ii) Fragile X-related Epigenetic Element 3 [FREE3] comprising the nucleotide sequence set forth in SEQ ID NO:1 or a homolog thereof or portion or part thereof defined by having at least 80% nucleotide sequence identity to SEQ ID NO:1 or which hybridizes to SEQ ID NO:1 or its complementary form under medium stringency conditions;
(iii) intron 2 comprising the nucleotide sequence set forth in SEQ ID NO:2 or a homolog thereof or portion or part thereof defined by having at least 80% nucleotide sequence identity to SEQ ID NO:2 or which hybridizes to SEQ ID NO:2 or its complementary form under medium stringency conditions;
(iv) change in methylation or other epigenetic modification relative to a control in genomic FREE2 region as a whole or specific fragments of FREE2 including FREE2 (D), FREE2 (E) or FREE3 comprising the nucleotide sequence set forth in SEQ ID NO:48 or 49 or 47, respectively or a homolog or portion or fragment thereof defined by having at least 80% nucleotide sequence identity to SEQ ID NO:48 or 49 or 47 or which hybridizes to SEQ ID NO:48 or 49 or 47 or its complementary form under medium stringency conditions;
(v) an intron, intron/exon boundary and/or splicing region downstream of intron 2 or a homolog or a portion or fragment thereof;
(vi) two or more of (a) an intron; (b) an intron/exon boundary; (c) a splicing region within the FMR locus; or
(vii) approximately one seventh or greater of an intron including an intron/exon boundary and/or a splicing region within the FMR genetic locus;
wherein the extent of methylation or epigenetic modification provides a correlation to the presence, state, classification or progression of the pathology;
(b) transferring the data from the user via a communications network;
(c) processing the subject data via multivariate or univariate analysis to provide a disease value;
(d) determining the status of the subject in accordance with the results of the disease value in comparison with predetermined values; and
(e) transferring an indication of the status of the subject to the user via the communications network.

Aspects disclosed herein are further described by the following non-limiting Example. In these Examples, materials and methods as outlined below were employed.

Patient Samples

FXS and premutation carrier EBV transformed lymphoblast cell lines were obtained from the tissue culture storage repository of the Murdoch Childrens Research Institute, Melbourne, Victoria, Australia or purchased from Coriell.

DNA Extraction

DNA for CGG repeat size PCR and methylation analysis was obtained either from 200 µl venous blood samples anti-coagulated with EDTA or from EBV transformed lymphoblasts 1 to 5×10$^6$ cells per sample and extracted using a BIO ROBOT M48 DNA Extractor, as per manufacturer's instructions (Qiagen Inc., Hilden, Germany). DNA for Southern blot or methylation analysis was extracted from 3 ml blood samples anti-coagulated with EDTA or from EBV transformed lymphoblasts 5 to 10×10$^6$ cells per sample.

CGG Repeat Size PCR Amplification

CGG repeat size for all samples was initially assessed using a fully validated PCR assay with precision of +/− one triplet repeat across the normal and GZ ranges, performed using a fragment analyzer (MegaB ace, GE Healthcare), with the higher detection limit of 170 repeats, as previously described (Khaniani et al., *Mol Cytogenet* 1(1):5, 2008). Briefly, PCR amplifications were performed using primers:

```
(i)
                                   [SEQ ID NO: 32])
r (5'-GCTCAGCTCCGTTTCGGTTTCACTTCCGGT-3;
and (ii)
                                   [SEQ ID NO: 33])
f (5'AGCCCCGCACTTCCACCACCAGCTCCTCCA-3',
```

(Fu et al., *Cell* 67(6):1047-1058, 1991) in a total volume of 25 µl containing 50 ng of genomic DNA, 0.75 pmol of each primer, 8 µl of 5× Q-Solution (Qiagen Inc., Hilden, Germany), 2.5 µl of 10×PCR Buffer and 1 unit of HotStarTaq Plus DNA polymerase (Qiagen Inc., Hilden, Germany) in a Gene Amp@ PCR System 9700. The PCR cycling profile was as follows: initial denaturation at 98° C. for 5 minutes; 35 cycles at 98° C. for 45 seconds, 70° C. for 45 seconds, and 72° C. for 2 minutes, and a final extension at 72° C. for 10 minutes. Alleles were sized by capillary electrophoresis using an automatic sequencer (MegaBACE™ 1000—GE HealthCare Amersham) with size standards (HealthCare) and controls of lengths 10, 23, 29, 30, 52 and 74 repeats determined by sequencing in-house or obtained from Coriel Cell Repositories web site (on the World-Wide Web at phppo.cdc.gov/dls/genetics/qcmaterials/).

CGG Repeat Size by Southern Blot

CGG sizes were assessed using a fully validated Southern Blot procedure with appropriate normal and abnormal controls for samples where the products could not be amplified using PCR (Fu et al 1991, supra; Francis et al., *Mol Diagn* 5(3):221-225, 2000). Briefly, 5 mg of DNA was digested with PstI (Boehringer Mannheim, Castle Hill, Australia), separated on 1% w/v agarose gels, and analyzed by Southern blot hybridization. The FMR-1 gene was detected using Southern blot analysis with probe Fxa3 and an X-chromosome control probe, pS8 (Yu et al., *Science* 252(5010):1179-1181, 1991). Probes were labeled using random oligonucleotide priming (Boehringer, Mannheim) with [a32-P]CTP (NEN Dupont, Boston, Mass.). Autoradiography was performed at −80° C., with intensifying screens and Kodak XAR films (Sigma-Aldrich).

Methylation Sensitive Southern Blot Analysis

Methylation of the classical FMR1 CpG island was assessed using a fully validated methyl sensitive Southern Blot procedure with appropriate normal and abnormal controls, as previously described (Tassone et al., *J. Mol. Diagn* 10:43-49, 2008). Briefly, EcoRI and NruI digestion was performed on 7 to 9 µg of DNA, and separated on a 0.8% w/v agarose/Tris acetate EDTA (TAE) gel. The DNA was denatured with HCL and NAOH, transferred to a charged nylon membrane and analyzed by Southern blot hybridization. The FMR1 alleles were detected using Southern blot analysis with probe StB12.3, labeled with Dig-11-dUTP by PCR (PCR Dig Synthesis kit; Roche Diagnostics). Autoradiography was performed with intensifying screens and Fuji Medical X-Ray film (Bedford, UK) and FMR1 methylation values for the expanded alleles were calculated as preciously described (Tassone et al., 2008 supra). The FMR1 activation ratios for female samples were calculated based on the following formula: optically scanned density of the 2.8 kb band/combined densities of the 2.8 kb and 5.2 kb bands (where the 2.8 kb band represents the proportion of normal active X and the 5.2 kb band represents the proportion of normal inactive X), as previously described (de Vries et al., *Am J Hum Genet*. 58:1025-1032, 1996).

MALDI-TOF Methylation Analysis

Bisulfite Treatment

Bisulfite treatment of genomic DNA at 0.5 µg per sample was performed using XCEED kit from MethylEasy (Human Genetic Signatures, Sydney, Australia) for sample sets of n<40. For sample sets n>40 96 well Methylamp kit from Epigentek (Brookly, N.Y., USA) was used. Duplicate bisulfite reactions were made from each sample, and six of the same control DNA samples spiked with DNA from an FXS patient cell line at 0, 33.3, 50, 66.6 or 100% were included as standards within each run, as an indicator of the inter-run variation in the degree of bisulfite related bias. Protocols were performed according to the manufacturer's instructions. Briefly, for the MethylEasy conversion, 20 µl of genomic DNA (0.5 µg total) was mixed with 2.2 µl of 3 µl NaOH, and incubated at 37° C. for 15 minutes, then denatured by 45 minute incubation at 80° C. 240 µl of the reagent #3 (XCEED kit, Human Genetic Signatures, Sydney, Australia) were then added to the mixture, which was transferred into the purification column and spun down at 10,000 g for 1 minute. The captured DNA was then washed in Reagent #4 (XCEED kit, Human Genetic Signatures, Sydney, Australia), and DNA eluted twice by placing 50 µl of the pre-warmed solution #5 (XCEED kit, Human Genetic Signatures, Sydney, Australia) onto column membrane, which was incubated for 1 minute at room temperature, and spun down at 10,000 g for 1 minute. The eluted DNA was then incubated at 95° C. for 20 minutes, with resulting final concentration at ~20 ng/µl per sample.

For the Methylamp conversion, 7 µl of genomic DNA (0.5 µg total) was mixed with 5 µl of the CF3 (Methylamp kit, Epigentek, Brookly, N.Y., USA) solution diluted 1:10 in distilled water, in each well of the 96 well plate. The DNA was denatured by placing the plate at 65° C. for 90 minutes. It was then captured in the filter plate and washed in 150 µl of the CF5 solution (Methylamp kit, Epigentek, Brookly, N.Y., USA), then twice in 250 µl of 80% v/v ethanol. The filter plate was then incubated in the CF3/90% ethanol solution, and washed twice in 90% v/v ethanol, as per manufacturer's instructions. The modified and cleaned DNA was then eluted with 40 µl of the CF6 solution (Methylamp kit, Epigentek, Brookly, N.Y., USA), with resulting converted DNA final concentration at ~20 ng/µl per sample. For the short term storage the converted DNA was kept at −20° C., and for storage of more than 3 months it was kept at −80° C.

PCR and In Vitro Transcription

The primers used to amplify the target regions and the annealing temperatures are listed in Tables 3 and 4. Each bisulfite converted sample was analyzed in duplicate PCR reactions, carried out in a total volume of 5 µl using 1 pmol of each primer, 40 µM dNTP, 0.2 U Hot Star Taq DNA polymerase (Qiagen Inc., Hilden, Germany), 1.5 mM MgCl$_2$ and buffer supplied with the enzyme (final concentration 1λ). The reaction mix was pre-activated for 15 min at 95° C., followed by 45 cycles of amplification at 94° C. for 20 s, primer specific annealing for 30 s and 72° C. for 1 min followed by 72° C. for 3 min. The PCR products were run on 1.5% w/v agarose gel to confirm successful PCR amplification and efficiency. The DNA was then cleaned up and the T or C-cleavage reactions were carried out (T-cleave for Amplicons 1 to 5, C-cleave for Amplicon 5 only) as per manufacturer's instructions (SEQUENOM, San Diego, Calif.). Briefly, unincorporated dNTPs were dephosphorylated by adding 1.7 µl H$_2$O and 0.3 U Shrimp Alkaline Phosphatase (SAP) [SEQUENOM, San Diego] to PCR products, which were incubated at 37° C. for 20 min, and 10 min at 85° C. to heat-inactivate the SAP. The transcription was performed on 2 µl of template DNA in the 6.5 ul reaction consisting of 20 U of the T7 R&DNA polymerase (Epicentre, Madison, Wis.) to incorporate either dCTP or dTTP; Ribonucleotides at 1 nM and the dNTP substrate at 2.5 mM, with other components used as recommended (SEQUENOM, San Diego). RNase A (SEQUENOM, San Diego) was then added to the mix to cleave the in vitro transcript. The mix was diluted to 27 µl in H$_2$O, and 6 mg CLEAN Resin (SEQUENOM, San Diego, Calif.) was added for conditioning of the phosphate backbone prior to MALDI-TOF MS. The SEQUENOM Nanodispenser was then used to spot the samples onto a SpectroCHIP for subsequent analysis. MassARRAY mass spectrometer (Bruker-SEQUENOM) was then used to collect mass spectra, which were analysed using the EpiTYPER software (Bruker-SEQUENOM). The calculation of the output methylation ratios for each CpG unit were based on the ratio of the signal intensities for the fragment from a methylated CpG unit/[methylated+unmethylated CpG units]. Further details are described in (Godler et al., 2010 supra).

RNA Extractions and Quality Assessments

Total RNA was extracted and purified using the Rneasy extraction kit, as per manufacturer's instructions (Qiagen Inc., Hilden, Germany). RNA concentrations were measured in triplicate using a NanoDrop ND-1000 Spectrophotometer, with purity being determined by the A260/A280 ratio using the expected values between 1.8 and 2. Total RNA quality and the degree of DNA contamination was also assessed using capillary electrophoresis Standard Sens Kit (Bio-rad), which involved descriptive comparison of chromatographic features based on previous publications using this system (Fleige and Pfaffl, *Mol Aspects Med* 27(2-3):126-139, 2006). Each RNA sample was then diluted to 30 ng/ul, to be used in for reverse transcription real-time PCR analysis, where mRNA quality at the Xq27.3 region was initially assessed by examining the relationship between 5' and 3' levels of FMR1 mRNA.

Standard Reverse Transcription Real-Time PCR

Reverse transcription was performed one reaction per sample using the Multiscribe Reverse Transcription System, 50 units/µl (Applied Biosystems). The 7900HT Fast Real Time PCR (Applied Biosystems) was used to quantify FMR1-5', FMR1-3', ASFMR1 (−1), (−2), (−3), GAPDH, B2M, and GUS, using the relative standard curve method. The target gene and the internal control gene dynamic linear ranges were performed on a series of doubling dilutions of an RNA standard (160-4 ng/µl). Since, both ASFMR1 assays do not target an exon/exon boundary, to minimize the impact of potential DNA contamination on the expression results, a no reverse transcription enzyme control was included for every sample. The difference between the plus and minus no reverse transcriptase control was considered as the ASFMR1 expression value for each sample. Previously published sequences were be used for primers and probe for: FMR1-5' and GUS (32); FMR1-3' (41). The following ASFMR1 primers and probes were designed using Primer Express 3.0 (Applied Biosystems):

```
ASFMR1 (-1) - Fw Primer
                                        [SEQ ID NO: 34]
(CCGCGGAATCCCAGAGA);

Rv Primer:
                                        [SEQ ID NO: 35]
(CAGTGGCGTGGGAAATCAA);

Probe:
                                        [SEQ ID NO: 36]
(FAM-TGGGATAACCGGATGCA-MGB).

ASFMR1 (-2) - Fw Primer:
                                        [SEQ ID NO: 37]
(ACACCCTGTGCCCTTTAAGG);

Rv Primer:
                                        [SEQ ID NO: 38]
(TCAAAGCTGGGTCTGAGGAAAG);

Probe:
                                        [SEQ ID NO: 39]
(VIC-TCGGGATCTCAAAATGT-TAMRA).

ASFMR1 (-3) - Fw Primer:
                                        [SEQ ID NO: 40]
(CCCCAGAATGAGAGGATGTTG);

Rv Primer:
                                        [SEQ ID NO: 41]
(GCCCTAGATCCACCGCTTTAA);

Probe:
                                        [SEQ ID NO: 42]
(FAM-TGCTGGTGGAACTC-MGB).
```

FMR1-5', FMR1-3', ASFMR1 primers and probes were be used at concentrations of 18 µM and 2 µM, respectively. GAPDH and B$_2$M primer/probe mixes will be obtained from PrimerDesign (PerfectProbe ge-PP-12-hu kit) and used at concentration of 2 µM. All of the above assays were single-plexed, with each sample assayed in duplicate 10 µl PCR reactions. The reactions consisted of 5.8 mM MgCl2, 1 µl Buffer A (Applied Biosystems), 3.35 µl Rnase-free water, 1.2 mM dNTPs, 0.01 units/µl of AmpliTaq Gold, 0.5 µl of TaqMan probe and 0.5 µl forward and 0.5 µl reverse primers, and 1 µl of the reverse transcription (cDNA) reaction. The annealing temperature for thermal cycling protocol was 60° C. for 40 cycles. The samples were quantified in arbitrary units (au) in relation to the standard curves performed on each plate, standardized to the mean of the 3 internal control genes (GUS, GAPDH and B$_2$M).

Amplicons

Amplicons were amplified using the primers and conditions shown in Tables 3 and 4. Table 5 shows prominent regulatory motif locations inclusive and proximal to FREE2 in FREE3. Amplicon 5 is as described by Godler et al., *Hum Mol Genet* 10(8):1618-1632. [Epub 2010]; Godler et al., *J. Mol Diagn.* 2011 [Epub ahead of print] doi: 10.1093/hmg/ddq1037, the contents of which are incorporated by reference.

TABLE 3

Amplicon details used for MALDI-TOF methylation analysis of the regions greater than 0.2 kb 3' of the CGG expansion at the Xq27.3 locus

| Amplicon No. | Annealing Temperature | Size (kb) | Distance 3' of CGG (kb): | Primer sequence (in capitals) and tag (in lower case) |
| --- | --- | --- | --- | --- |
| FREE2(B) | (I) 94° C. 4 min; 25 cycles of: touchdown PCR -0.5° C. per cycle -94° C. 20 s; 64° C. 30 s; 72° C. 1 min. (II) 20 cycles of: 94° C. for 20 s, 59° C. for 30 s, 72° C. for 1 min. (III) 72° C. for 3 min; 4° C. forever | 500 | 0.207 | Fw: 5'-aggaagagagGGTTTTTTTGAAATTTTTGG ATTTA-3' (SEQ ID NO: 6) Rv: 5'-cagtaatacgactcactatagggagaaggctTAAAAC CTATTAAAAACCCCTCTCC-3' (SEQ ID NO: 7) |
| FREE2(C) | (I) 94° C. 4 min; 25 cycles of: touchdown PCR -0.5° C. per cycle -94° C. 20 s; 64° C. 30 s; 72° C. 1 min. (II) 20 cycles of: 94° C. for 20 s, 59° C. for 30 s, 72° C. for 1 min. (III) 72° C. for 3 min; 4° C. forever | 302 | 0.504 | Fw: 5'-aggaagagagTAAGAGGGTTTTAGGTTTTTTTTGG-3' (SEQ ID NO: 8) Rv: 5'-cagtaatacgactcactatagggagaaggctAAAACATA TACATTCCTAAATTTACCCC-3' (SEQ ID NO: 9) |
| FREE3 (ASFMR1) | (I) 94° C. 4 min; 25 cycles of: touchdown PCR -0.5° C. per cycle -94° C. 20 s; 64° C. 30 s; 72° C. 1 min. (II) 20 cycles of: 94° C. for 20 s, 59° C. for 30 s, 72° C. for 1 min. (III) 72° C. for 3 min; 4° C. forever | 327 | 9.739 | Fw: 5'-aggaagagagTTTTTTTTATATAGGTATTTGTAAAGG ATG-3' (SEQ ID NO: 10) Rv: 5'-cagtaatacgactcactatagggagaaggctTCTCTAAT TTCTTTCTTCACATTCAAAA-3' (SEQ ID NO: 11) |

TABLE 4

Amplicon details used to define FREE2 3' Border region using MALDI-TOF methylation analysis within the FMR1 intron 1 sequence at the Xq27.3 locus

| Amplicon No. | Annealing Temperature | Size (kb) | Distance 3' of CGG 3' end (kb): | Primer sequence (in capitals) and tag (in lower case) |
| --- | --- | --- | --- | --- |
| FREE2(D) (pp4) | (I) 95° C. 15 min (II) 10 cycles of: 94° C. 20 s; 56° C. 30 s; 72° C. 1 min. 35 cycles of: 94° C. for 20 s, 62° C. for 30 s, 72° C. for 1 min. (III) 72° C. for 3 min; 4° C. forever | 374 | 0.790 | Fw: 5'-aggaagagagAAAAGTTTTAGGA AGATTTTAATATGG-3' (SEQ ID NO: 58) Rv: 5'-cagtaatacgactcactatagggagaaggc tAAAAAACACAATAAACCCATAA ATACC-3' (SEQ ID NO: 59) |
| FREE2(E) (pp6) | (I) 95° C. 15 min (II) 10 cycles of: 94° C. 20 s; 56° C. 30 s; 72° C. 1 min. 35 cycles of: 94° C. for 20 s, 62° C. for 30 s, 72° C. for 1 min. (III) 72° C. for 3 min; 4° C. forever | 360 | 1.424 | Fw: 5'-aggaagagagGAATGGTTTGAATGTTTT AGATAGGAT -3' (SEQ ID NO: 60) Rv: 5'-cagtaatacgactcactatagggagaaggctAC CAAAAATCTAATAACCAAAACCAC-3' (SEQ ID NO: 61) |
| FREE3 (ASFMR1) | (I) 95° C. 15 min (II) 10 cycles of: 94° C. 20 s; 56° C. 30 s; | 327 | 9.908 | Fw: 5'-aggaagagagTTTTTTTTATATAGGTATT TGTAAAGGATG -3' (SEQ ID NO: 62) |

TABLE 4-continued

Amplicon details used to define FREE2 3' Border region using MALDI-TOF methylation analysis within the FMR1 intron 1 sequence at the Xq27.3 locus

| Amplicon No. | Annealing Temperature | Size (kb) | Distance 3' of CGG 3' end (kb): | Primer sequence (in capitals) and tag (in lower case) |
|---|---|---|---|---|
| | 72° C. 1 min. 35 cycles of: 94° C. for 20 s, 62° C. for 30 s, 72° C. for 1 min. (III) 72° C. for 3 min; 4° C. forever | | | Rv: 5'-cagtaatacgactcactatagggagaaggctTCTCTAATTTCTTTCTTCACATTCAAAA-3' (SEQ ID NO: 63) |

TABLE 5

Prominent regulatory motif locations inclusive and proximal to FREE2 and FREE3 regions

| TRANSCRIPTION FACTOR SITES/POTENTIAL REGULATORY MOTIFS: | SEQUENCE ON THE SENSE STRAND: | SEQ ID NO | STRAND | SEQUENCE HOMOLOGY (%) | AMPLICON | CPG UNIT LOCATION: |
|---|---|---|---|---|---|---|
| GATA-1 | GGCGATGGCT | 12 | LEADING | 95 | FREE2(A) | CpG15 and CpG16 |
| HSF2 | TGAATATTCG | 13 | LEADING | 96 | FREE2(B) | CpG7 and CpG8/9 |
| C/EBP | AAGTTTCCAAAGA | 14 | LAGGING | 95 | FREE2(D) | CpG6 and CpG7 |
| CdxA | TATTATTATT | 15 | LAGGING | 99 | FREE2(D) | CpG6 and CpG7 |
| AML-1a | ACCACA | 16 | LAGGING | 100 | FREE2(D) | 3' of CpG7 |
| AML-1a | TGTGGTG | 17 | LEADING | 100 | FREE2(D) | 3' of CpG7 |
| CdxA | TATAAAT | 18 | LAGGING | 100 | N/A | Between FREE2(D) and FREE2(E) |
| CdxA | TATAAAT | 19 | LAGGING | 100 | N/A | Between FREE2(D) and FREE2(E) |
| CdxA | AATAATAT | 20 | LEADING | 99 | N/A | Between FREE2(D) and FREE2(E) |
| HFH-1/HFH-2 | AAATAAACAAT | 21 | LAGGING | 97 | FREE2(E) | CpG1 and CpG2/3 |
| CdxA | CATAAAT | 22 | LAGGING | 100 | FREE2(E) | CpG1 and CpG2/3 |
| SRY | TTTGTTT | 23 | LAGGING | 100 | N/A | 3' of FREE2(E) CpG6 |
| SRY | TTTGTTT | 24 | LAGGING | 100 | N/A | 3' of FREE2(E) CpG6 |
| SRY | TTGTTTA | 25 | LAGGING | 99 | N/A | 3' of FREE2(E) CpG6 |
| S8 | TTTATTTAATTAAGTT | 26 | LEADING | 96 | N/A | 3' of FREE2(E) CpG6 |
| SRY | AAACAAA | 27 | LEADING | 100 | 5' of FREE3 | 5' of FREE3 CpG1 |
| CdxA | TATAATT | 28 | LEADING | 99 | FREE3 | CpG1 |
| Oct-1 | TTTATGCTAATT | 29 | LEADING | 99 | FREE3 | Between CpG1 and CpG2 |

EXAMPLE 1

Mapping Methylation of the FMR Genetic Locus Using High Throughput Mass Spectrometry The structure of the FMR genetic locus is shown in FIG. 1A and FIG. 6A and comprises the FMR1 promoter, and FMR1 and ASFMR1 genes. A CGG repeat is located within the 5' (UTR) of the FMR1 gene. ASFMR1 spans the CGG expansion in the antisense direction and is also regulated by another promoter located in the exon 2 of FMR1. The FREE2 located downstream of the CGG expansion. The FREE3 region is located within intron 2 of FMR1 downstream of the second ASFMR1 promoter.

The primers utilized for MALDI-TOF methylation analysis targeted 4 regions at the Xq27.3 locus designated as FREE2(A) [described as amplicon 5 in Godler et al., 2010 supra]; FREE2(B); FREE2(C) and FREE3 (color coded). Individual CPG sites within each region are numbered accordingly. Prominent transcription factor binding sites and methylation sensitive restriction enzyme recognition sites are indicated in capital font, and are listed/identified in Tables 3 and 4. Numerous HpaII/MspI sites (CCGG) are located throughout the FREE2 A, B and C region.

Figure 2:
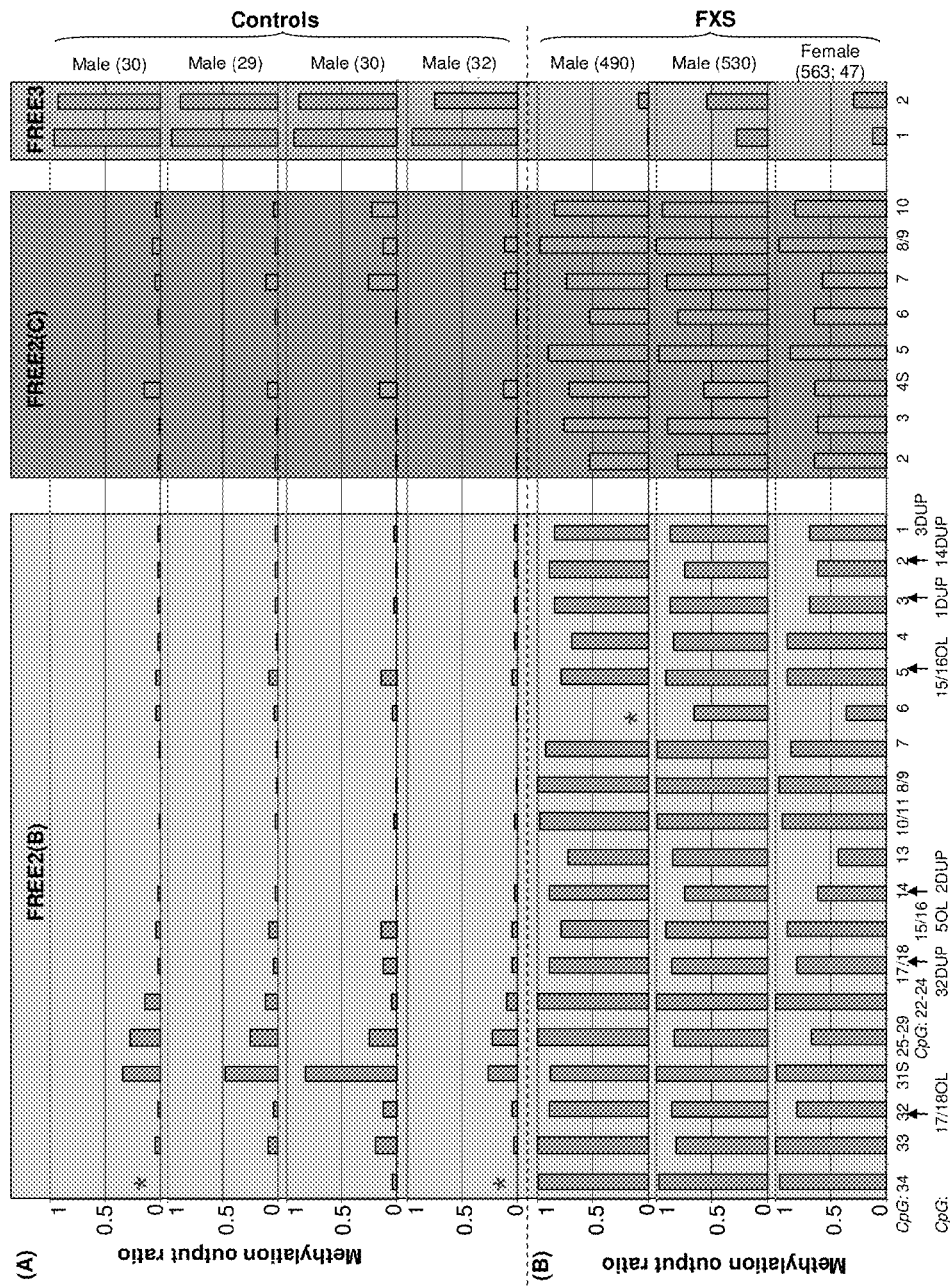
FIG. 2 is a graphical representation of the methylation pattern variation between healthy controls and FXS individuals within the body of the FMR1 gene, 5' of the CGG expansion. DNA from lymphoblasts of (A) healthy controls (n=4) and (B) Fragile X syndrome affected patients (n=3). Methylation of individual CpGs, were analyzed within the 9.762 kb region 5' CGG expansion, inclusive of intron 1, exon 2 and intron 2 (sequence numbering from GenBank L29074 L38501) using 3 SEQUENOM mass spectrometry assays (see Table 2). *—represent missing values. OL—represent CpG unit/s with overlaying fragment peak; DUP—represent CpG units with peak/s of the same size.

Regions identified as biologically significant showed consistent differences in methylation between healthy controls and FxS samples (FIG. 1B and FIGS. 2A and B). These include HpaII/MspI sites throughout FREE2 A, B and C regions including but not restricted to the FREE2B CCGG sites located at CpGs 6, 9, 13 and between CpGs 25 and 26; as well as FREE2 (C) CCGG site located at CpG1. These would be sensitive to HpaII methylation specific digestion, which can be followed by PCR or other restriction enzyme based methods to assay differential methylation between healthy controls and FxS samples, and potentially carriers of smaller expansion alleles.

Figure 5:
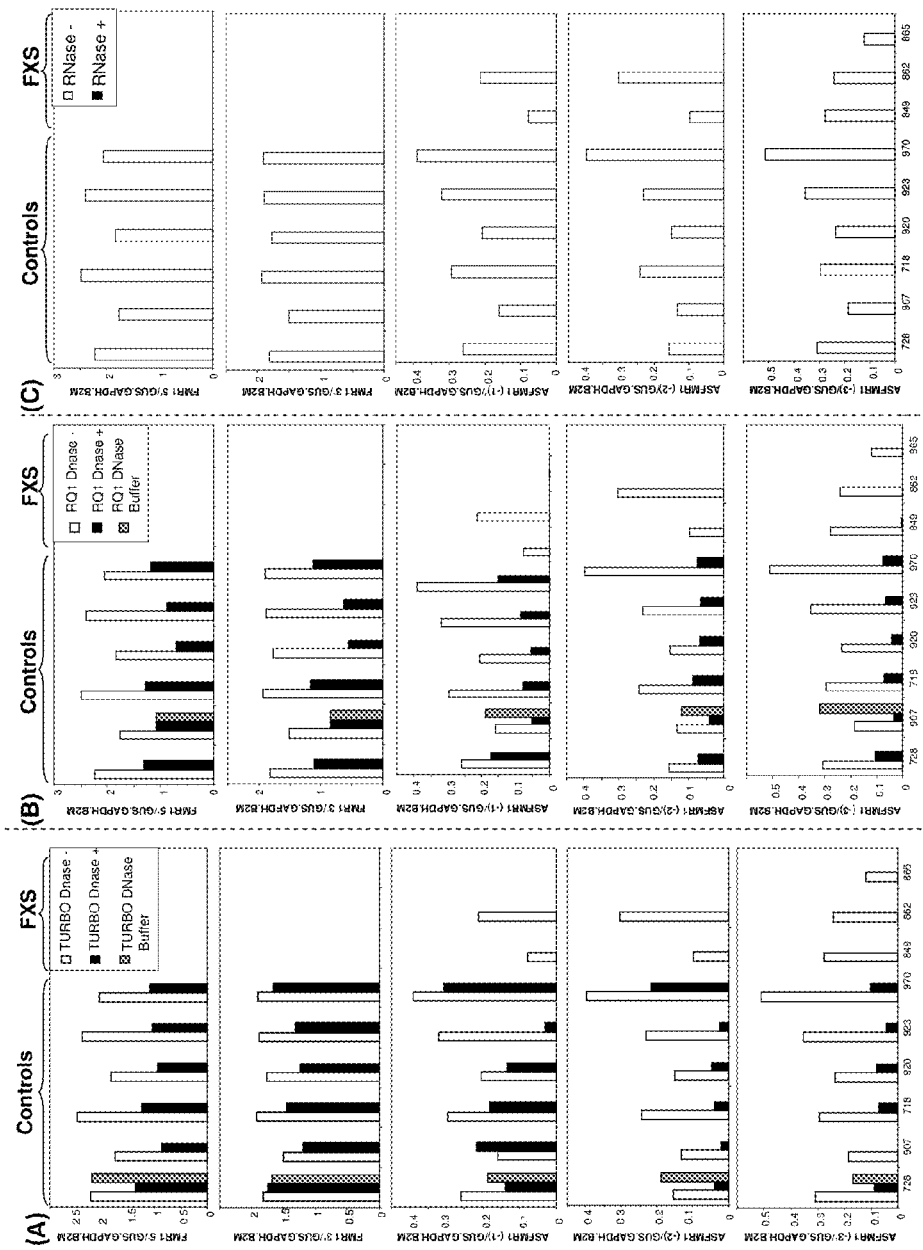
FIG. 5. Graphical representations of different FMR1 and ASFMR1 transcripts in RNA samples from lymphoblast lines of 6 male controls, two FXS males (samples 849 and 862) and one FXS female (865). The control and FXS RNA samples were either treated with TURBO DNase (A), RQ1 DNase (B), RNase A (C), or were untreated. Addition of TURBO DNase or RQ1 DNAse buffers to RNA samples without DNase were included as additional controls in A and B. The FMR1 and ASFMR1 transcripts were quantified using real-time RT-PCR relative standard curve method, normalized to mRNA levels of three internal control genes, GUS, GAPDH and B2M. FMR15' and 3' assays showed no signal for the FXS RNA samples, while similar levels were detected in all control samples (upper two panels in A, B and C). TURBO and RQ1 DNAse treatment caused ~50% decrease in the FMR1 levels in most of the control samples; while RNase A treatment caused complete loss of FMR1 and ASFMR1 signals. While decrease of ASMFR1 (−1)(−2) and (−3) levels was also observed in all control samples caused by TURBO and RQ1 DNAse treatment, in FxS samples (with analogous to control ASFMR1 levels in the untreated samples) TURBO and RQ1 DNAse treatment resulted in complete loss of signal for all three ASFMR1 assays. Because DNase can only degrade RNA molecules if they form complexes with DNA, this suggests that ASFMR1 RNA forms RNA:DNA complexes more readily in FxS samples than in controls. Increase in RNA:DNA interaction of ASFMR1 in FXS may lead to methylated FMR1 promoter and adjacent regions (FIG. 1) and silencing FMR1 expression leading to loss of FMRP and the resulting FXS clinical phenotype.

Other regions identified as biologically significant that showed consistent differences in methylation between healthy controls and FxS samples (FIG. 1B and FIGS. 2A and B and Table 5) included: (I) GATA-1 site (FREE2B between CpG 15 and 16); (II) HSF2 site (FREE2C between CpG 7, 8 and 9); (III) an SRY site located upstream of FREE3; (IV) a CdxA/TATA box site located at CpG1 of FREE3; (V) an Oct-1 site located between CpG sites 1 and 2 within FREE3. Differential methylation of any of these sites in diseased individuals compared to controls may have an affect of relevant transcription factor binding and/or further epigenetic modification; which would inturn affect transcription of FMR1, ASFMR1 and/or FMR4. Or may result or reflect aberrant non coding RNA expression and/or RNA:DNA interactions or stability of RNA:DNA hybrids (FIGS. 4B and C and FIG. 5).

EXAMPLE 2

Determining the Impact of Technical Variation on Quantitative Analysis of Methylation and Evidence for Disease Specific Methylation within Intron 1 and Intron 2 of FMR1

Figure 3:
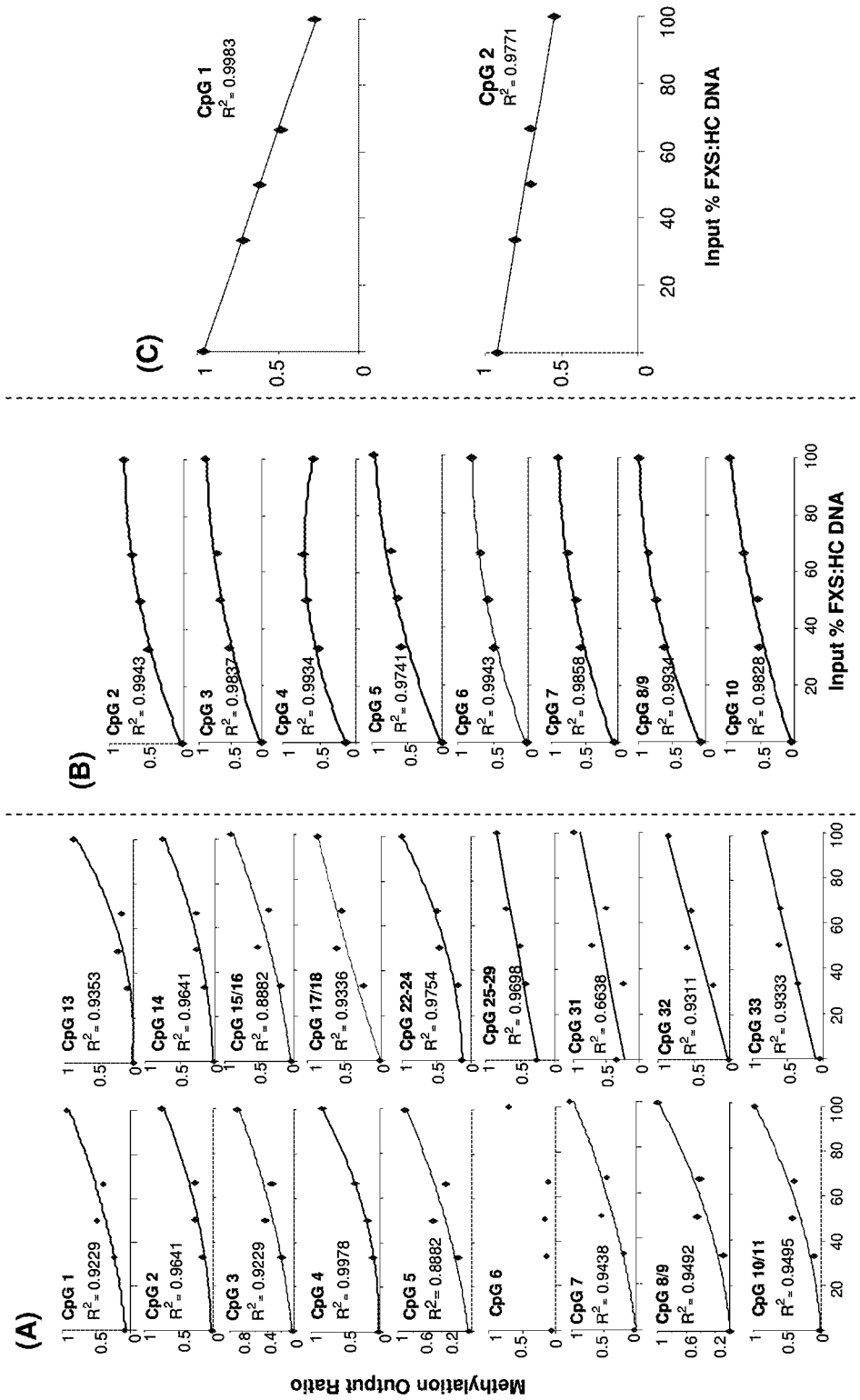
FIG. 3. Graphical representations of a spiking experiment indicating the quantification limits of the MALDI-TOF methylation analysis of the Fragile X Syndrome (FXS) DNA within the 9.762 kb region 5' CGG expansion, inclusive of intron 1, exon 2 and intron 2 (sequence numbering from GenBank L29074 L38501) using 3 SEQUENOM mass spectrometry assays (A) FREE2(B); (B) FREE2(C); (C) FREE3). Healthy control DNA was spiked with FXS DNA at 1:0; 2:1; 1:1; 1:2; 0:1 ratios corresponding to 0, 33.3, 50, 66.6, 100% FXS DNA in the sample. The spiked DNA samples were analyzed using MALDI-TOF methylation analysis at three sequential regions at the Xq27.3 locus (see FIG. 1 for locations). The methylated vs unmethylated ratios at each analysable CpG unit were expressed as output methylation ratios on Y axis, with FXS DNA input % expressed on the X axis (each point represents mean of duplicate PCRs from a single bisulfite converted DNA mixture). Methylation output ratios for CpG sites within FREE2B and FREE2C amplicons (A and B) were positively correlated with increasing FXS DNA input %; while FREE3 Methylation output ratios were negatively correlated with increasing FXS DNA input %.

DNA from lymphoblasts of healthy controls with 30 CGG repeats, normal levels of FMR1 mRNA and FMRP, and DNA from lymphoblasts of FXS patient with 530 CGG, silenced FMR1 transcription and absence of FMRP were mixed at ratios of 1:0; 2:1; 1:1; 1:2; 0:1 corresponding to 0, 33.3, 50, 66.6, 100% FXS DNA in the sample (FIG. 3). The spiked DNA samples were bisulfite converted in duplicate reactions. Each reaction was amplified with primer sets (forward and reverse primers) as listed by SEQ ID NOs: which corresponded to 3 SEQUENOM mass spectrometry assays (A: FREE2(B); B: FREE2(C); C: FREE3). The spiked DNA samples were analysed using MALDI-TOF methylation analysis at three sequential regions at the Xq27.3 locus (see FIG. 1 for locations). The methylated vs unmethylated ratios at each analysable CpG unit were expressed as output methylation ratios on Y axis, with FXS DNA input % expressed on the X axis (each point represents mean of duplicate PCRs from a single bisulfite converted DNA mixture). Methylation output ratios for CpG sites within FREE2B and FREE2C amplicons (A and B) were positively correlated with increasing FXS DNA input %; while FREE3 Methylation output ratios were negatively correlated with increasing FXS DNA input % with high Pierson's correlation. This clearly demonstrates that the FREE2 region comprising a large portion of FMR1 intron 1 is hypermethylated in FXS sample while FREE3 region within intron 2 of FMR1 is hypomethylated in the FXS sample. This methylation pattern is reversed in the healthy control sample, and supports the differential methylation patterns within FREE2 and FREE3 related to the disease state as shown in FIGS. 2A and B.

EXAMPLE 3

Evidence for Expression of ASFMR1 in FXS and Disease Specific RNA:DNA Interactions Standard curve and amplification real-time PCR plots (of assays described in FIG. 4A) show that in the FXS cell lines, ASFMR1 RNA with fully methylated FMR1 promoter and silenced FMR1 and FMRP, ASFMR1 is expressed (FIG. 4B). RNA was extracted from 3 FXS cell lines whose methylation profiles are presented in FIG. 2; Sample 849 was taken from the male 490 CGG repeat line; Sample 862 was taken from the male 530 CGG repeat line; Sample 865 was taken from the female 563 and 47 CGG repeat line. Each RNA sample was split in two, with one half subjected to RNase A treatment prior to ASFMR1 (−3) relative standard curve analysis. The ASFMR1 (−3) real-time PCR analysis was performed in quadruplicate reactions. The difference in Ct values between RNase A treated and untreated samples represents the level of ASFMR1 expression.

Standard curve and amplification real-time PCR plots (FIGS. 4C and D) also indicate that in the FXS cell lines, ASFMR1RNA forms RNA:DNA complexes. FXS RNA samples were treated with TURBO DNase (C) and RQ1 DNase (D) respectively. These DNase treatments caused complete loss of real-time-PCR signal for the ASFMR1(−3) assay. Because DNase can only degrade RNA molecules if they form complexes with DNA, loss of ASFMR1 after DNase treatment suggests that ASFMR1RNA forms RNA:DNA complexes in FxS samples with fully methylated FMR1 promoter and silenced FMR1 expression.

Expression of different FMR1 and ASFMR1 transcripts (detailed in FIG. 4A) was detected in RNA samples from lymphoblast lines of 6 male controls, two FXS males (samples 849 and 862) and one FXS female (865) [FIGS. 5A and B]. The control and FXS RNA samples were either treated with TURBO DNase (A), RQ1 DNase (B), RNase A (C), or were untreated. Addition of TURBO DNase or RQ1 DNAse buffers to RNA samples without DNase were included as additional controls in (FIGS. 5A and B). The FMR1 and ASFMR1 transcripts were quantified using real-time RT-PCR relative standard curve method, normalized to mRNA levels of three internal control genes, GUS, GAPDH and B2M. FMR1 5' and 3' assays showed no signal for the FXS RNA samples, while similar levels were detected in all control samples (upper two panels in FIGS. 5A, B and C). TURBO and RQ1 DNAse treatment caused ~50% decrease in the FMR1 levels in most of the control samples; while RNase A treatment caused complete loss of FMR1 and ASFMR1 signals. While decrease of ASMFR1 (−1), (−2) and (−3) levels was also observed in all control samples caused by TURBO and RQ1 DNAse treatment, in F×S samples (with analogous to control ASFMR1 levels in the untreated samples) TURBO and RQ1 DNAse treatment resulted in complete loss of signal for all three ASFMR1 assays. Because DNase can only degrade RNA molecules if they form complexes with DNA, this suggests that ASFMR1 RNA forms RNA:DNA complexes more readily in F×S samples than in controls. Increase in RNA:DNA interaction of ASFMR1 in FXS may lead to methylated FMR1 promoter and adjacent regions (FIG. 1) and silencing FMR1 expression leading to loss of FMRP and the resulting FXS clinical phenotype.

EXAMPLE 4

Figure 7:
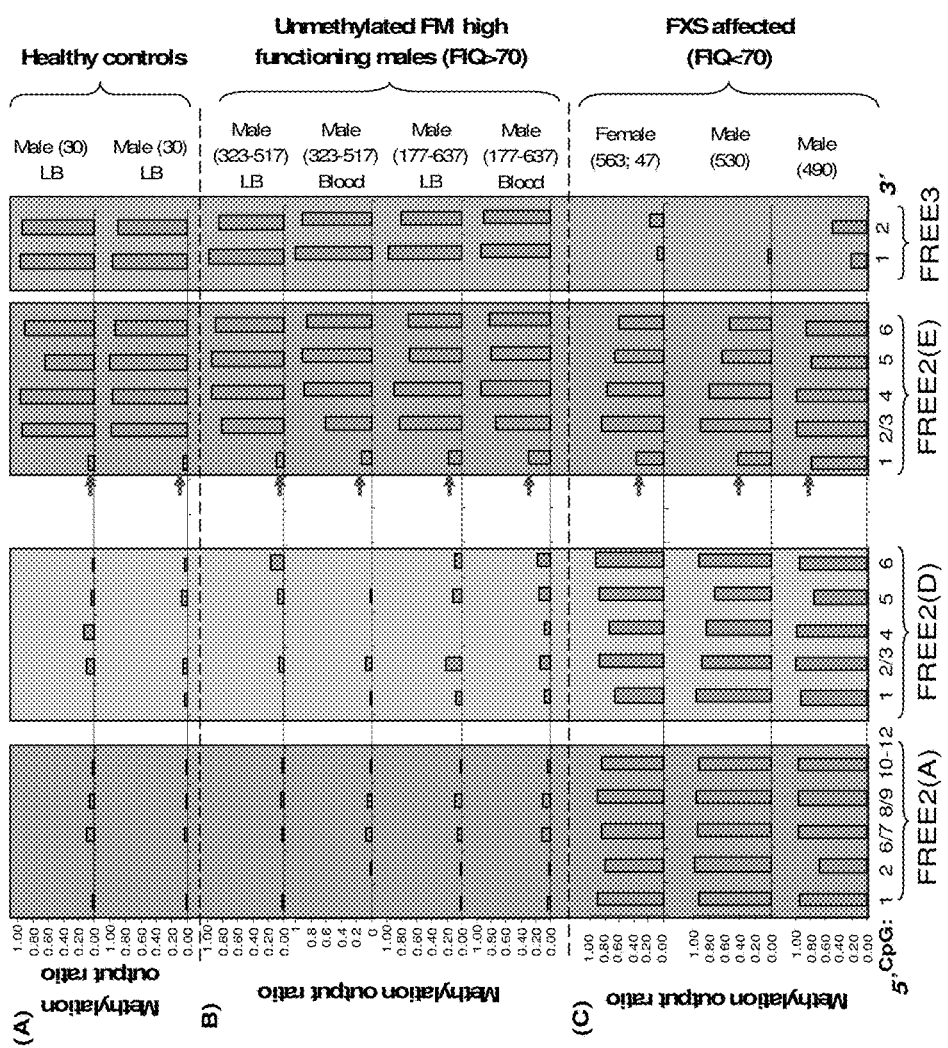
FIG. 7 is a graphical representation of the methylation pattern variation in lymphoblasts and blood between (A) healthy controls, (B) unmethylated FM 'high functioning' males with full scale IQ (FIQ) greater than 70, (C) FXS affected individuals full scale IQ (FIQ) less than 70. Methylation output ratio (Y axis) of individual CpG units (X axis), were analyzed within the 27 kb region 3' CGG expansion, inclusive of intron 1, exon 2 and intron 2 (sequence numbering from GenBank L29074 L38501). The SEQUENOM mass spectrometry assays FREE2(D) and FREE2(E) (see Tables 3 and 4) were the most proximal to the FREE2 3' Boundary highlighted with the RED arrow as the CpG 1 of the FREE2(E) assay. It is evident from the representation that this CpG unit is the last one within the FREE2 region which is unmethylated in healthy controls and high functioning FM individuals while being hyper methylated in FXS affected individuals. It is evident from the representation that the FREE3 region methylation status is an important biomarker of the FXS phenotype as it is hypermethylated in high functioning FM individuals as well as in healthy controls, while being hypomethylated in FXS affected individuals. It is also evident from the representation that the methylation patterns are consistent between lymphoblasts and blood. LB-represents lymphoblasts.

Characterizing the 3' Boundary of the FMR1 Promoter Located within the FREE2 Region—1.3 Kb from the 5' End of the FMR1 Intron 1—Relative to Transcription There is significant inhibition of transcription of the FMR4, ASFMR1 and FMR1 genes in FXS patients which is likely caused by the methylation of the CpG units in Amplicon 1 (FREE 1 region), and/or Amplicon 5 (FREE 2 region) in association with the FMR1 promoter. It is demonstrated here that the FREE2 region and FMR1 promoter expands 1302 base pair into the FMR1 intron 1 from 5' end of the intron (FIG. 6A through C). In subjects with FM affected with FXS with cognitive impairment (IQ<70) with no FMR1 mRNA or FMRP and significantly decreased from normal ASFMR1/FMR4 mRNA levels, FREE2 CpG units from FREE2(A) amplicon expanding to CpG unit 1 on the FREE2(E) amplicon have methylation status approaching 100% (FIG. 7C) In these same cell lines the FREE1 and FREE2 regions and the FMR1 promoter were fully methylated. In healthy controls and the 'high functioning' FM males with IQ>70 the same region (FREE2 CpG units from FREE2(A) amplicon expanding to CpG unit 1 on the FREE2 (E)) have methylation status approaching 0% (FIGS. 7A and B). The DNA regions 5' of the CpG unit 1 (eg CpG2/3 of FREE2E on the FREE2(E) do not show any difference in methylation between affected FM, healthy controls and 'high functioning full mutation males, as these regions have methylation status approaching 100% in all groups examined (FIG. 7). Therefore, the assay enabled herein clearly identifies the 3' boundary of the FREE2 region and the FMR1 promoter, which is located between CpG unit 1 of the FREE2(E) amplicon and CpG unit 2/3 of the FREE2(E) amplicon.

These data also indicate that methylation of the FREE1 region is closely related to inhibition of bi-directional transcription and translation of the FMR locus required for normal neuronal development. As a consequence, this can lead to pathological conditions such as FXS, mental retardation and autism. Hence, the assay examining one or more biomarker sites herein can be used to diagnose, make a prognosis and detect the presence or predisposition to FXS, and potentially any other neuropathological condition's associated with elevated methylation and/or altered distribution of methylated sites in the FMR locus described herein.

EXAMPLE 5

Methylation Status of FREE3 in "High Functioning" Males and FM Carrier Females

To determine if FREE3 region is informative in biological settings, methylation of FREE3 was examined in blood and lymphoblast DNA samples of 'high functioning' FM males with IQ>70, FMR1 mRNA expression in blood which was 2.6 fold elevated above the normal levels and FMRP expression which was moderately reduced. The methylation results were compared to healthy control males and FXS affected FM males with no FMR1 expression and no FMRP expression and hypermethylated FMR1 promoter encompassing the FMR1 CpG island, FREE1 and FREE2 regions. It is evident from the representations in FIG. 6 that the FREE3 region methylation status is an important biomarker of the FXS phenotype as it is hypermethylated in high functioning FM individuals as well as in healthy controls, while being hypomethylated in FXS affected individuals. It is also evident from the representation that the methylation patterns are consistent between lymphoblasts and blood.

These data indicate that decreased methylation of the FREE3 region is closely related to inhibition of bi-directional transcription and translation of the FMR locus required from normal neuronal development as ASFMR1 transcription start site is located between CpG units 1 and 2 of the FREE3 region. As a consequence, this can lead to pathological conditions such as FXS, mental retardation and autism. Hence, the assay examining one or more biomarker sites herein can be used to diagnose, make a prognosis and detect the presence or predisposition to FXS, and potentially any other neuropathological condition/s associated with elevated methylation and/or altered distribution of methylated sites in the FMR locus described herein.

Those skilled in the art will appreciate that aspects of the disclosure described herein are susceptible to variations and modifications other than those specifically described. It is to be understood that these aspects include all such variations and modifications. These aspects also include all of the steps, features, compositions and compounds referred to or indicated in this specification, individually or collectively, and any and all combinations of any two or more of the steps or features.

BIBLIOGRAPHY

Allingham-Hawkins et al., *Am J Med Genet* 83(4):322-325, 1999
Bodega et al., *Hum Reprod* 21(4):952-957, 2006
Bonner and Laskey, *Eur. J. Biochem.* 46: 83, 1974
Chiurazzi et al., *Hum Mol Genet* 7(1):109113, 1998
Coulam, *Fertil Steril* 38(6):645-655, 1982
Dahl et al., *Clin Chem* 53(4):790-793, 2007
de Vries et al., *Am J Hum Genet.* 58:1025-1032, 1996
Fahy et al., *PCR Methods Appl.* 1(1):25-33, 1991
Fleige and Pfaffl, *Mol Aspects Med* 27(2-3):126-139, 2006
Francis et al., *Mol Diagn* 5(3):221-225, 2000
Fu et al., *Cell* 67(6):1047-1058, 1991
Gitan et al., *Genome Res.* 12(1):158-164, 2002
Godler et al., *Hum Mol Genet* 10(8):1618-1632. [Epub 2010]

Godler et al., *J. Mol Diagn.* 2011 [Epub ahead of print]
Hagerman et al., *Neurology* 57(1):127-130, 2001
Irizarry et al., *Nature Genetics* 41(2):178-186, 2009
Irwin et al., *Cereb Cortex* 10(10):1038-1044, 2000
Jacquemont et al., *Am J Ment Retard* 109(2):154-164, 2004
Jacquemont et al., *J Med Genet* 42(2):e14, 2005
Jin and Warren, *Hum. Mol. Genet* 9(6):901-908, 2000
Jin et al., *Neuron* 39(5):739-747, 2003
Kenneson et al., *Hum Mol Genet* 10(14):14491454, 2001
Khalil et al., *PLoS ONE* 3(1):e1486, 2008
Khaniani et al., *Mol Cytogenet* 1(1):5, 2008
Ladd et al., *Hum Mol Genet* 16(24):3174-3187, 2007
Loesch et al., *Clin Genet* 67(5):412-417, 2005
Loesch et al., *J Med Genet* 44(3):200-204, 2007
Marmur and Doty, *J. Mol. Biol.* 5: 109, 1962
Mitchell et al., *Clin Genet* 67(1):38-46, 2005
Nolin et al., *Am J Hum Genet* 72(2):454-464, 2003
Nygren et al., *Nucleic Acids Res.* 33(14):e128, 2005
On and Zoghbi, *Ann Rev Neurosci* 30:575-621, 2007
Pieretti et al., *Cell* 66(4):817-822, 1991
Pietrobono et al., *Nucleic Acids Res* 30(14):3278-3285, 2002
Rein et al., *Nucleic Acids Res.* 26:2255, 1998
Sullivan et al., *Hum Reprod* 20(2):402-412, 2005
Tassone et al., *J. Mol. Diagn* 10:43-49, 2008
Terracciano et al., *Am J Med Genet C Semin Med Genet* 137C(1):32-37, 2005
Tost et al., *Nucleic Acids Res* 31(9):e50, 2003
Verkerk et al., *Cell* 65(5):905-914, 1991
Wojdacz et al., *Nucleic Acids Res.* 35(6):e41, 2007
Yegnasubramanian et al., *Nucleic Acids Res.* 34(3):e19, 2006
Yu et al., *Science* 252(5010):1179-1181, 1991

What is claimed is:

1. A method of detecting methylation in Fragile X-related Epigenetic Element 2(E) (FREE2(E)) in genomic DNA of a human subject, the method comprising:
   (a) obtaining isolated genomic DNA from the human subject,
   (b) amplifying wholly or partially FREE2(E) consisting of the nucleotide sequence of SEQ ID NO:49 or a modified SEQ ID NO:49 in which methylated cytosine(s) in SEQ ID NO:49 are converted to uracil(s) using a first primer complementary to a first region of SEQ ID NO:49 or to the modified SEQ ID NO:49 sequence in which methylated cytosine(s) have been converted to uracil(s) and a second primer complementary to a second region of SEQ ID NO:49 or to the modified SEQ ID NO:49 sequence in which methylated cytosine(s) have been converted to uracil(s), wherein the second primer is non-overlapping with the first primer; and
   (c) detecting methylation in the wholly or partially amplified FREE2(E).

2. The method of claim 1 wherein the genomic DNA is isolated from a cell from the human subject selected from the group consisting of a cultured or uncultured Chorionic Villi Sample (CVS) cell, a lymphoblast cell, a blood cell, buccal cell, epithelial cell, fibroblast cell, an amniocyte or an EBV transformed lymphoblast cell line.

3. The method of claim 1, wherein FREE2(E), consisting of the nucleotide sequence of SEQ ID NO: 49, is amplified using primers having the nucleotide sequences of SEQ ID NO: 45 and SEQ ID NO: 46.

4. The method of claim 1, wherein the method further comprises determining the length of $(CGG)_n$ expansion.

5. The method of claim 1, wherein step (b) comprises amplifying at least a part of a modified SEQ ID NO:49 in which methylated cytosine(s) in SEQ ID NO:49 is/are converted to uracil(s), and wherein prior to step (b) the method comprises:
   deaminating cytosines in the isolated genomic DNA by treating the isolated genomic DNA with bisulfite for a time and under conditions sufficient to convert non-methylated cytosines to uracils,
   wherein at least one of the first or second primers complementary to modified SEQ ID NO:49 in which methylated cytosine(s) in SEQ ID NO:49 are converted to uracil(s) comprises a dinucleotide or a trinucleotide selected from the group consisting of a TG, a CG and a CNG, wherein amplification using a primer comprising a TG indicates the presence of a non-methylated cytosine at the corresponding position in SEQ ID NO:49, and amplification using a primer comprising CG or CNG, where N indicates any nucleotide, indicates presence of a methylated cytosine at the corresponding position in SEQ ID NO:49.

6. The method of claim 1, wherein prior to step (b), the method comprises digesting the genomic DNA with a methylation-sensitive restriction endonuclease, and the digested genomic DNA is amplified in step (b).

* * * * *